US007271149B2

(12) United States Patent
Glaesner et al.

(10) Patent No.: US 7,271,149 B2
(45) Date of Patent: Sep. 18, 2007

(54) GLP-1 FUSION PROTEINS

(75) Inventors: Wolfgang Glaesner, Indianapolis, IN (US); Radmila Micanovic, Indianapolis, IN (US); Sheng-Hung Rainbow Tschang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 365 days.

(21) Appl. No.: 10/433,108

(22) PCT Filed: Nov. 29, 2001

(86) PCT No.: PCT/US01/43165

§ 371 (c)(1), (2), (4) Date: May 29, 2003

(87) PCT Pub. No.: WO02/46227

PCT Pub. Date: Jun. 13, 2002

(65) Prior Publication Data

US 2004/0053370 A1 Mar. 18, 2004

Related U.S. Application Data

(60) Provisional application No. 60/251,954, filed on Dec. 7, 2000.

(51) Int. Cl.
*A61K 38/26* (2006.01)
*C07K 14/605* (2006.01)
*C07K 14/76* (2006.01)

(52) U.S. Cl. ........................ 514/12; 530/308; 530/362

(58) Field of Classification Search .................... None
See application file for complete search history.

(56) References Cited

U.S. PATENT DOCUMENTS 5,665,863 A 9/1997 Yeh
5,766,883 A 6/1998 Balance et al.
5,876,966 A * 3/1999 Reed ........................ 435/69.3
5,876,969 A 3/1999 Fleer et al.
6,190,909 B1 * 2/2001 Levinson et al. ........... 435/325
6,191,102 B1 * 2/2001 DiMarchi et al. .............. 514/2
6,514,500 B1 * 2/2003 Bridon et al. ............ 424/193.1
7,141,547 B2 11/2006 Rosen et al.
7,189,690 B2 3/2007 Rosen et al.

FOREIGN PATENT DOCUMENTS

| | | |
|---|---|---|
| EP | 0 413 622 | * 2/1991 |
| WO | WO97/24445 | 7/1997 |
| WO | WO98/04718 | 2/1998 |
| WO | WO 00 69911 | 11/2000 |
| WO | WO 01/79258 | 10/2001 |
| WO | WO 01/79271 | 10/2001 |
| WO | WO 03 059934 | 7/2003 |
| WO | WO 03 060071 | 7/2003 |

OTHER PUBLICATIONS

Baggio et al., "A Recombinant Human Glucagon-Like Peptide (GLP)-1-Albumin Protein (Albugon) . . . ," Diabetes, vol. 53, Sep. 2004, pp. 2492-2500.*

Knudsen, Lotte B, et al: "Potent Derivatives of Glucagon-Like Peptide-1 with Pharmacokinetic Properties Suitable for once Daily Administration." Journal of Medicinal Chemistry, vol. 43, No. 9, May 4, 2000, pp. 1664-1669, XP002222050, ISSN: 0022-2623.

Paige, et al. "Prolonged Circulation of Recombinant Human Granulocyte-Colony Stimulating Factor by Covalent Linkage to Albumin Through a Heterobifunctional Polyethylene Glycol." Pharmaceutical Research, vol. 12, No. 12, 1995, pp. 1883-1885.

Sytkowski, A., et al. "An Erythropoietin Fusion Protein Comprised of Identical Repeating Domains Exhibits Enhanced Biological Properties." The Journal of Biological Chemistry, vol. 274, No. 35, Aug. 1999, pp. 24773-24778.

* cited by examiner

*Primary Examiner*—Robert A Wax
(74) *Attorney, Agent, or Firm*—Gregory A. Cox

(57) ABSTRACT

The present invention relates to glucagon-like-1 compounds fused to proteins that have the effect of extending the in vivo half-life of the peptides. These fusion proteins can be used to treat non-insulin dependent diabetes mellitus as well as a variety of other conditions.

13 Claims, 17 Drawing Sheets

Fig. 1

Figure 4:
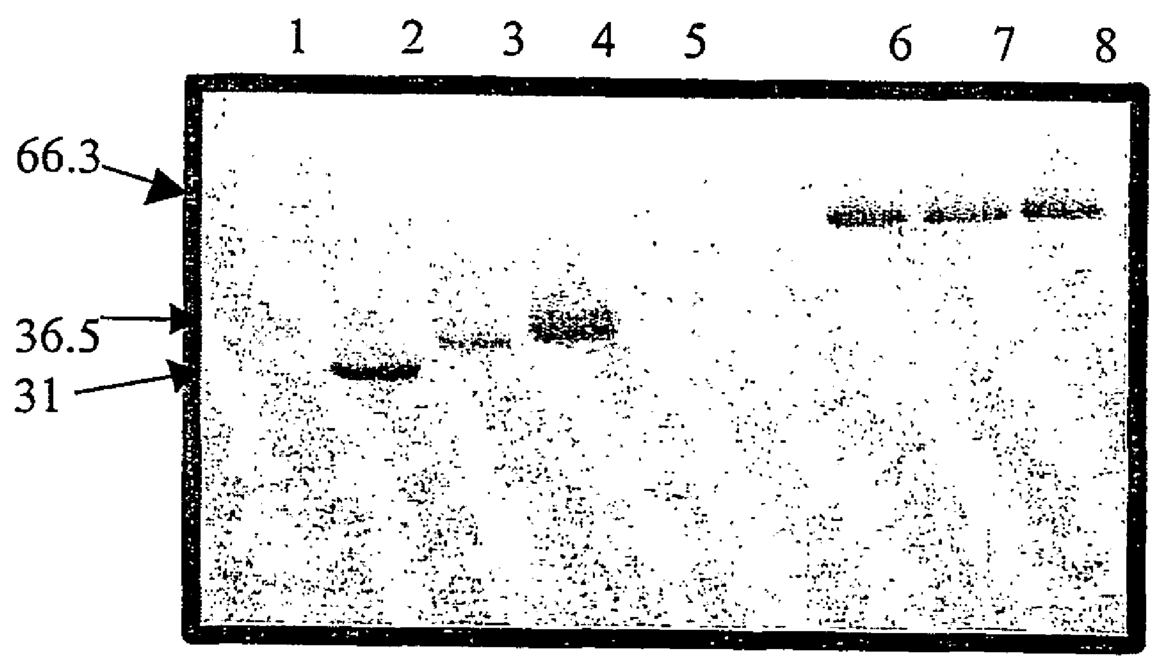

```
                    5                   10                  15
Ala Glu Pro Lys Ser Cys Asp Lys Thr His Thr Cys Pro Pro Cys
                    20                  25                  30
Pro Ala Pro Glu Lys Gly Gly Pro Ser Val Phe Leu Phe Pro Pro
                    35                  40                  45
Lys Pro Lys Asp Thr Lys Met Ile Ser Arg Thr Pro Glu Val Thr
                    50                  55                  60
Cys Val Val Val Asp Val Ser His Glu Asp Pro Glu Val Lys Phe
                    65                  70                  75
Asn Trp Tyr Val Asp Gly Val Glu Val His Asn Ala Lys Thr Lys
                    80                  85                  90
Pro Arg Glu Glu Gln Tyr Asn Ser Thr Tyr Arg Val Val Ser Val
                    95                  100                 105
Leu Thr Val Leu His Gln Asp Trp Leu Asn Gly Lys Glu Tyr Lys
                    110                 115                 120
Cys Lys Val Ser Asn Lys Ala Leu Pro Ala Pro Ile Glu Lys Thr
                    125                 130                 135
Ile Ser Lys Ala Lys Gly Gln Pro Arg Glu Pro Gln Val Tyr Thr
                    140                 145                 150
Leu Pro Pro Ser Arg Glu Glu Met Thr Lys Asn Gln Val Ser Leu
                    155                 160                 165
Thr Cys Leu Val Lys Gly Phe Tyr Pro Ser Asp Ile Ala Val Glu
                    170                 175                 180
Trp Glu Ser Asn Gly Gln Pro Glu Asn Asn Tyr Lys Thr Thr Pro
                    185                 190                 195
Pro Val Leu Asp Ser Asp Gly Ser Phe Phe Leu Tyr Ser Lys Leu
                    200                 205                 210
Thr Val Asp Lys Ser Arg Trp Gln Gln Gly Asn Val Phe Ser Cys
                    215                 220                 225
Ser Val Met His Glu Ala Leu His Asn His Tyr Thr Gln Lys Ser
                    230
Leu Ser Leu Ser Pro Gly Lys        [SEQ ID NO: 32]
```

Fig. 2

```
                5                   10                  15
Asp Ala His Lys Ser Glu Val Ala His Arg Phe Lys Asp Leu Gly Glu Glu Asn
    20                  25                  30                  35
Phe Lys Ala Leu Val Leu Ile Ala Phe Ala Gln Tyr Leu Gln Gln Cys Pro Phe
            40                  45                  50
Glu Asp His Val Lys Leu Val Asn Glu Val Thr Glu Phe Ala Lys Thr Cys Val
55                  60                  65                  70
Ala Asp Glu Ser Ala Glu Asn Cys Asp Lys Ser Leu His Thr Leu Phe Gly Asp
        75                  80                  85                  90
Lys Leu Cys Thr Val Ala Thr Leu Arg Glu Thr Tyr Gly Glu Met Ala Asp Cys
                95                  100                 105
Cys Ala Lys Gln Glu Pro Glu Arg Asn Glu Cys Phe Leu Gln His Lys Asp Asp
    110                 115                 120                 125
Asn Pro Asn Leu Pro Arg Leu Val Arg Pro Glu Val Asp Val Met Cys Thr Ala
            130                 135                 140
Phe His Asp Asn Glu Glu Thr Phe Leu Lys Lys Tyr Leu Tyr Glu Ile Ala Arg
145                 150                 155                 160
Arg His Pro Tyr Phe Tyr Ala Pro Glu Leu Leu Phe Phe Ala Lys Arg Tyr Lys
        165                 170                 175                 180
Ala Ala Phe Thr Glu Cys Cys Gln Ala Ala Asp Lys Ala Ala Cys Leu Leu Pro
                185                 190                 195
Lys Leu Asp Glu Leu Arg Asp Glu Gly Lys Ala Ser Ser Ala Lys Gln Arg Leu
    200                 205                 210                 215
Lys Cys Ala Ser Leu Gln Lys Phe Gly Glu Arg Ala Phe Lys Ala Trp Ala Val
            220                 225                 230
Ala Arg Leu Ser Gln Arg Phe Pro Lys Ala Glu Phe Ala Glu Val Ser Lys Leu
235                 240                 245                 250
Val Thr Asp Leu Thr Lys Val His Thr Glu Cys Cys His Gly Asp Leu Leu Glu
        255                 260                 265                 270
Cys Ala Asp Asp Arg Ala Asp Leu Ala Lys Tyr Ile Cys Glu Asn Gln Asp Ser
                275                 280                 285
Ile Ser Ser Lys Leu Lys Glu Cys Cys Glu Lys Pro Leu Leu Glu Lys Ser His
    290                 295                 300                 305
Cys Ile Ala Glu Val Glu Asn Asp Glu Met Pro Ala Asp Leu Pro Ser Leu Ala
            310                 315                 320
Ala Asp Phe Val Glu Ser Lys Asp Val Cys Lys Asn Tyr Ala Glu Ala Lys Asp
325                 330                 335                 340
Val Phe Leu Gly Met Phe Leu Tyr Glu Tyr Ala Arg Arg His Pro Asp Tyr Ser
        345                 350                 355                 360
Val Val Leu Leu Leu Arg Leu Ala Lys Thr Tyr Glu Thr Thr Leu Glu Lys Cys
                365                 370                 375
Cys Ala Ala Ala Asp Pro His Glu Cys Tyr Ala Lys Val Phe Asp Glu Phe Lys
    380                 385                 390                 395
Pro Leu Val Glu Glu Pro Gln Asn Leu Ile Lys Gln Asn Cys Glu Leu Phe Glu
            400                 405                 410
Asn Leu Gly Glu Tyr Lys Phe Gln Asn Ala Leu Leu Val Arg Tyr Thr Lys Lys
415                 420                 425                 430
Val Pro Gln Val Ser Thr Pro Thr Leu Val Glu Val Ser Arg Asn Leu Gly Lys
        435                 440                 445                 450
Val Gly Ser Lys Cys Cys Lys His Pro Glu Ala Lys Arg Met Pro Cys Ala Glu
                455                 460                 465
Asp Tyr Leu Ser Val Val Leu Asn Gln Leu Cys Val Leu His Glu Lys Thr Pro
    470                 475                 480                 485
Val Ser Asp Arg Val Thr Lys Cys Cys Thr Glu Ser Leu Val Asn Arg Arg Pro
```

Fig. 2 Continued

```
            490                     495                     500
Cys Phe Ser Ala Leu Glu Val Asp Glu Thr Tyr Val Pro Lys Glu Phe Asn Ala
505                 510                     515                 520
Glu Thr Phe Thr Phe His Ala Asp Ile Cys Thr Leu Ser Glu Lys Glu Arg Gln
        525                     530                     535                 540
Ile Lys Lys Gln Thr Ala Leu Val Glu Leu Val Lys His Lys Pro Lys Ala Thr
                545                     550                     555
Lys Glu Gln Leu Lys Ala Val Met Asp Asp Phe Ala Ala Phe Val Glu Lys Cys
    560                     565                     570                     575
Cys Lys Ala Asp Asp Lys Glu Thr Cys Phe Ala Glu Glu Gly Lys Lys Leu Val
            580                     585
Ala Ala Ser Gln Ala Ala Leu Gly Leu
```

[SEQ ID NO: 34]

Fig. 3
A.
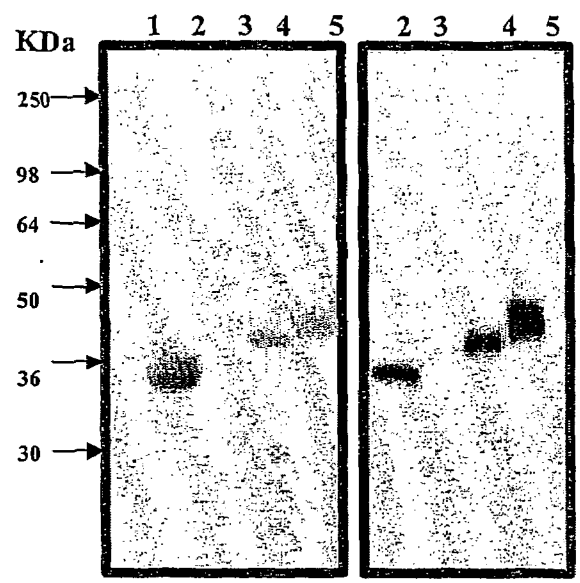
B.
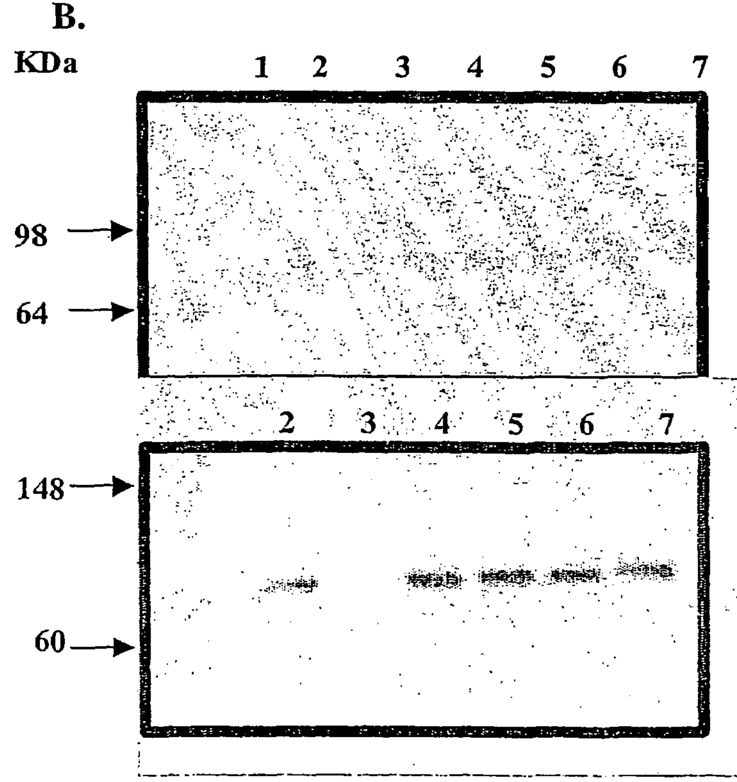

A.

B.

A.

B.

Fig. 12

1
GAGCCCAAATCTTGTGACAAAACTCACACATGCCCACCGTGCCCAGCACC
50
TGAACTCCTGGGGGGACCGTCAGTCTTCCTCTTCCCCCCAAAACCCAAGG
100
ACACCCTCATGATCTCCCGGACCCCTGAGGTCACATGCGTGGTGGTGGAC
150
GTGAGCCACGAAGACCCTGAGGTCAAGTTCAACTGGTACGTGGACGGCGT
200
GGAGGTGCATAATGCCAAGACAAAGCCGCGGGAGGAGCAGTACAACAGCA
250
CGTACCGTGTGGTCAGCGTCCTCACCGTCCTGCACCAGGACTGGCTGAAT
300
GGCAAGGAGTACAAGTGCAAGGTCTCCAACAAAGCCCTCCCAGCCCCCAT
350
CGAGAAAACCATCTCCAAAGCCAAAGGGCAGCCCCGAGAACCACAGGTGT
400
ACACCCTGCCCCCATCCCGGGAGGAGATGACCAAGAACCAGGTCAGCCTG
450
ACCTGCCTGGTCAAAGGCTTCTATCCCAGCGACATCGCCGTGGAGTGGGA
500
GAGCAATGGGCAGCCGGAGAACAACTACAAGACCACGCCTCCCGTGCTGG
550
ACTCCGACGGCTCCTTCTTCCTCTATAGCAAGCTCACCGTGGACAAGAGC
600
AGGTGGCAGCAGGGGAACGTCTTCTCATGCTCCGTGATGCATGAGGCTCT
650
GCACAACCACTACACGCAGAAGAGCCTCTCCCTGTCTCCGGGTAAATGAT
700
AGT [SEQ ID NO: 33]

Fig. 13

1
GATGCGCACAAGAGTGAGGTTGCTCATCGGTTTAAAGATTTGGGAGAAGA
50
AAATTTCAAAGCCTTGGTGTTGATTGCCTTTGCTCAGTATCTTCAGCAGT
100
GTCCATTTGAAGATCATGTAAAATTAGTGAATGAAGTAACTGAATTTGCA
150
AAAACATGTGTTGCTGATGAGTCAGCTGAAAATTGTGACAAATCACTTCA
200
TACCCTTTTTGGAGACAAATTATGCACAGTTGCAACTCTTCGTGAAACCT
250
ATGGTGAAATGGCTGACTGCTGTGCAAAACAAGAACCTGAGAGAAATGAA
300
TGCTTCTTGCAACACAAAGATGACAACCCAAACCTCCCCCGATTGGTGAG
350
ACCAGAGGTTGATGTGATGTGCACTGCTTTTCATGACAATGAAGAGACAT
400
TTTTGAAAAAATACTTATATGAAATTGCCAGAAGACATCCTTACTTTTAT
450
GCCCCGGAACTCCTTTTCTTTGCTAAAAGGTATAAAGCTGCTTTTACAGA
500
ATGTTGCCAAGCTGCTGATAAAGCTGCCTGCCTGTTGCCAAAGCTCGATG
550
AACTTCGGGATGAAGGGAAGGCTTCGTCTGCCAAACAGAGACTCAAGTGT
600
GCCAGTCTCCAAAAATTTGGAGAAAGAGCTTTCAAAGCATGGGCAGTAGC
650
TCGCCTGAGCCAGAGATTTCCCAAAGCTGAGTTTGCAGAAGTTTCCAAGT
700
TAGTGACAGATCTTACCAAAGTCCACACGGAATGCTGCCATGGAGATCTG
750
CTTGAATGTGCTGATGACAGGGCGGACCTTGCCAAGTATATCTGTGAAAA
800
TCAAGATTCGATCTCCAGTAAACTGAAGGAATGCTGTGAAAAACCTCTGT
850
TGGAAAAATCCCACTGCATTGCCGAAGTGGAAAATGATGAGATGCCTGCT
900
GACTTGCCTTCATTAGCTGCTGATTTTGTTGAAAGTAAGGATGTTTGCAA
950
AAACTATGCTGAGGCAAAGGATGTCTTCCTGGGCATGTTTTTGTATGAAT
1000
ATGCAAGAAGGCATCCTGATTACTCTGTCGTGCTGCTGCTGAGACTTGCC

Fig. 13 Continued

1050
AAGACATATGAAACCACTCTAGAGAAGTGCTGTGCCGCTGCAGATCCTCA
1100
TGAATGCTATGCCAAAGTGTTCGATGAATTTAAACCTCTTGTGGAAGAGC
1150
CTCAGAATTTAATCAAACAAAATTGTGAGCTTTTTGAGCAGCTTGGAGAG
1200
TACAAATTCCAGAATGCGCTATTAGTTCGTTACACCAAGAAAGTACCCCA
1250
AGTGTCAACTCCAACTCTTGTAGAGGTCTCAAGAAACCTAGGAAAAGTGG
1300
GCAGCAAATGTTGTAAACATCCTGAAGCAAAAAGAATGCCCTGTGCAGAA
1350
GACTATCTATCCGTGGTCCTGAACCAGTTATGTGTGTTGCATGAGAAAAC
1400
GCCAGTAAGTGACAGAGTCACCAAATGCTGCACAGAATCCTTGGTGAACA
1450
GGCGACCATGCTTTTCAGCTCTGGAAGTCGATGAAACATACGTTCCCAAA
1500
GAGTTTAATGCTGAAACATTCACCTTCCATGCAGATATATGCACACTTTC
1550
TGAGAAGGAGAGACAAATCAAGAAACAAACTGCACTTGTTGAGCTCGTGA
1600
AACACAAGCCCAAGGCAACAAAAGAGCAACTGAAAGCTGTTATGGATGAT
1650
TTCGCAGCTTTTGTAGAGAAGTGCTGCAAGGCTGACGATAAGGAGACCTG
1700
CTTTGCCGAGGAGGGTAAAAAACTTGTTGCTGCAAGTCAAGCTGCCTTAG
1750
GCTTATAATGAC [SEQ ID NO: 35]

SEQUENCE LISTING

```
<160> NUMBER OF SEQ ID NOS: 35

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Ala, Gly, Ser, Thr, Leu,
      Ile, Val, Glu, Asp, or Lys;
<220> FEATURE:
<221> NAME/KEY: MISC_FEATURE
<222> LOCATION: (3)..(3)
<223> OTHER INFORMATION: Xaa at position 3 is Glu, Asp, or Lys;
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, or Lys;
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys;
<220> FEATURE:
<221> NAME/KEY: MISC_FEATURE
```

-continued

```
<222> LOCATION: (10)..(10)
<223> OTHER INFORMATION: Xaa at position 10 is Val, Ala, Gly, Ser, Thr,
      Leu, Ile, Tyr, Glu, Asp, or Lys;
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys;
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, Lys, Trp or Tyr;
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gln, or Lys;
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, Lys, Trp or Tyr;
<220> FEATURE:
<221> NAME/KEY: MISC_FEATURE
<222> LOCATION: (15)..(15)
<223> OTHER INFORMATION: Xaa at position 15 is Glu, Asp, or Lys;
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, Trp or Lys;
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      or Lys;
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, or Lys;
<220> FEATURE:
<221> NAME/KEY: MISC_FEATURE
<222> LOCATION: (20)..(20)
<223> OTHER INFORMATION: Xaa at position 20 is Lys, Arg, Gln, Glu, Asp,
      or His;
<220> FEATURE:
<221> NAME/KEY: MISC_FEATURE
<222> LOCATION: (21)..(21)
<223> OTHER INFORMATION: Xaa at position 21 is Leu, Glu, Asp, or Lys;
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, or Lys;
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      or Lys;
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys;
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, or Lys;
<220> FEATURE:
<221> NAME/KEY: MISC_FEATURE
<222> LOCATION: (28)..(28)
```

```
<223> OTHER INFORMATION: Xaa at position 28 is Asn, Lys, Arg, Glu, Asp,
      or His;
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, or Lys;
<220> FEATURE:
<221> NAME/KEY: MISC_FEATURE
<222> LOCATION: (30)..(30)
<223> OTHER INFORMATION: Xaa at position 30 is Gly, Arg, Lys, Glu, Asp,
      or His;
<220> FEATURE:
<221> NAME/KEY: MISC_FEATURE
<222> LOCATION: (31)..(31)
<223> OTHER INFORMATION: Xaa at position 31 is Pro, Gly, Ala, Ser, Thr,
      Leu, Ile, Val, Glu, Asp, or Lys, or is deleted;
<220> FEATURE:
<221> NAME/KEY: MISC_FEATURE
<222> LOCATION: (32)..(32)
<223> OTHER INFORMATION: Xaa at position 32 is Ser, Arg, Lys, Glu, Asp,
      or His, or is deleted;
<220> FEATURE:
<221> NAME/KEY: MISC_FEATURE
<222> LOCATION: (33)..(33)
<223> OTHER INFORMATION: Xaa at position 33 is Ser, Arg, Lys, Glu, Asp,
      or His, or is deleted;
<220> FEATURE:
<221> NAME/KEY: MISC_FEATURE
<222> LOCATION: (34)..(34)
<223> OTHER INFORMATION: Xaa at position 34 is Gly, Asp, Glu, or Lys, or
      is deleted;
<220> FEATURE:
<221> NAME/KEY: MISC_FEATURE
<222> LOCATION: (35)..(35)
<223> OTHER INFORMATION: Xaa at position 35 is Ala, Phe, Trp, Tyr, Glu,
      Asp, or Lys, or is deleted;
<220> FEATURE:
<221> NAME/KEY: MISC_FEATURE
<222> LOCATION: (36)..(36)
<223> OTHER INFORMATION: Xaa at position 36 is Ser, Pro, Lys, Glu, or
      Asp, or is deleted;
<220> FEATURE:
<221> NAME/KEY: MISC_FEATURE
<222> LOCATION: (37)..(37)
<223> OTHER INFORMATION: Xaa at position 37 is Ser, Pro, Glu, Asp, or
      Lys, or is deleted;
<220> FEATURE:
<221> NAME/KEY: MISC_FEATURE
<222> LOCATION: (38)..(38)
<223> OTHER INFORMATION: Xaa at position 38 is Gly, Pro, Glu, Asp, or
      Lys, or is deleted;
<220> FEATURE:
<221> NAME/KEY: MISC_FEATURE
<222> LOCATION: (39)..(39)
<223> OTHER INFORMATION: Xaa at position 39 is Ala, Ser, Val, Glu, Asp,
      or Lys, or is deleted;

<400> SEQUENCE: 2

His Xaa Xaa Gly Xaa Phe Thr Xaa Asp Xaa Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa Xaa
            20                  25                  30

Xaa Xaa Xaa Xaa Xaa Xaa Xaa
        35


<210> SEQ ID NO 3
<211> LENGTH: 32
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
```

```
<223> OTHER INFORMATION: Xaa at position 1 is L-histidine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (3)..(3)
<223> OTHER INFORMATION: Xaa at position 3 is Thr, Ser, Arg, Lys, Trp,
      Phe, Tyr, Glu, or His;
<220> FEATURE:
<221> NAME/KEY: MISC_FEATURE
<222> LOCATION: (5)..(5)
<223> OTHER INFORMATION: Xaa at position 5 is Asp, Glu, Arg, Thr, Ala,
      Lys, or His;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Tyr, Glu, or Ala;
<220> FEATURE:
<221> NAME/KEY: MISC_FEATURE
<222> LOCATION: (12)..(12)
<223> OTHER INFORMATION: Xaa at position 12 is His, Pro, Asp, Glu, Arg,
      Ser, Ala, or Lys;
<220> FEATURE:
<221> NAME/KEY: MISC_FEATURE
<222> LOCATION: (16)..(16)
<223> OTHER INFORMATION: Xaa at position 13 is Gly, Asp, Glu, Gln, Asn,
      Lys, Arg, or Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, Gln,
      or Arg;
<220> FEATURE:
<221> NAME/KEY: MISC_FEATURE
<222> LOCATION: (18)..(18)
<223> OTHER INFORMATION: Xaa at position 18 is Glu, Arg, Ala, or Lys;
<220> FEATURE:
<221> NAME/KEY: MISC_FEATURE
<222> LOCATION: (20)..(20)
<223> OTHER INFORMATION: Xaa at position 20 is Trp, Tyr, Phe, Asp, Lys,
      Glu, or His;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (25)..(25)
<223> OTHER INFORMATION: Xaa at position 25 is Asp, Glu, Ser, Thr, Arg,
      Trp, or Lys;
<220> FEATURE:
<221> NAME/KEY: MISC_FEATURE
<222> LOCATION: (27)..(27)
<223> OTHER INFORMATION: Xaa at position 27 is Asp, Arg, Val, Lys, Ala,
      Gly, or Glu;
<220> FEATURE:
<221> NAME/KEY: MISC_FEATURE
<222> LOCATION: (28)..(28)
<223> OTHER INFORMATION: Xaa at position 28 is Glu, Lys, or Asp;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
```

<220> FEATURE:
<221> NAME/KEY: MISC_FEATURE
<222> LOCATION: (30)..(30)
<223> OTHER INFORMATION: Xaa at position 30 is Thr, Ser, Asp, Trp, Tyr, Phe, Arg, Glu, or His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu, Asp, Trp, Tyr, Phe, His, Gly, or is deleted.
<220> FEATURE:
<221> NAME/KEY: MISC_FEATURE
<222> LOCATION: (32)..(32)
<223> OTHER INFORMATION: Xaa at position 31 is Pro or is deleted.

<400> SEQUENCE: 3

Xaa Xaa Xaa Gly Xaa Xaa Thr Ser Asp Xaa Ser Xaa Tyr Leu Glu Xaa
1 5 10 15

Xaa Xaa Ala Xaa Xaa Phe Ile Xaa Xaa Leu Xaa Xaa Xaa Xaa Xaa Xaa
20 25 30

<210> SEQ ID NO 4
<211> LENGTH: 32
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine, or is deleted.
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile, Ser, or Thr;
<220> FEATURE:
<221> NAME/KEY: MISC_FEATURE
<222> LOCATION: (5)..(5)
<223> OTHER INFORMATION: Xaa at position 5 is Asp, Glu, Arg, Thr, Ala, Lys, or His;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His, Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn, Lys, Arg, or Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, or Gln;
<220> FEATURE:
<221> NAME/KEY: MISC_FEATURE
<222> LOCATION: (18)..(18)
<223> OTHER INFORMATION: Xaa at position 18 is Glu, His, Ala, or Lys;
<220> FEATURE:
<221> NAME/KEY: MISC_FEATURE
<222> LOCATION: (19)..(19)
<223> OTHER INFORMATION: Xaa at position 19 is Asp, Lys, Glu, or His;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr, Trp, Arg, or Lys;
<220> FEATURE:
<221> NAME/KEY: MISC_FEATURE

```
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (27)..(27)
<223> OTHER INFORMATION: Xaa at position 27 is Asp, Arg, Val, Lys, Ala,
      Gly, or Glu;
<220> FEATURE:
<221> NAME/KEY: MISC_FEATURE
<222> LOCATION: (28)..(28)
<223> OTHER INFORMATION: Xaa at position 28 is Glu, Lys, or Asp;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (30)..(30)
<223> OTHER INFORMATION: Xaa at position 30 is Arg, Glu, or His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, Gly, or is deleted.
<220> FEATURE:
<221> NAME/KEY: MISC_FEATURE
<222> LOCATION: (32)..(32)
<223> OTHER INFORMATION: Xaa at position 32 is Pro, or is deleted.

<400> SEQUENCE: 4

Xaa Xaa Glu Gly Xaa Xaa Thr Ser Asp Xaa Ser Ser Tyr Leu Glu Xaa
1               5                   10                  15

Xaa Xaa Xaa Lys Xaa Phe Ile Xaa Trp Leu Xaa Xaa Xaa Xaa Xaa Xaa
            20                  25                  30


<210> SEQ ID NO 5
<211> LENGTH: 32
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, Met, or Thr;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, or Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (20)..(20)
<223> OTHER INFORMATION: Xaa at position 20 is Asp, Lys, Glu, or His;
```

```
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, Gly, or is deleted.
<220> FEATURE:
<221> NAME/KEY: MISC_FEATURE
<222> LOCATION: (32)..(32)
<223> OTHER INFORMATION: Xaa at position 32 is Pro or is deleted.

<400> SEQUENCE: 5

Xaa Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa Xaa
            20                  25                  30


<210> SEQ ID NO 6
<211> LENGTH: 32
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, or Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (18)..(18)
<223> OTHER INFORMATION: Xaa at position 18 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, Gly, Gly-Pro, or is deleted.
<220> FEATURE:
<221> NAME/KEY: MISC_FEATURE
<222> LOCATION: (32)..(32)
<223> OTHER INFORMATION: Xaa at position 32 is Pro or is deleted.

<400> SEQUENCE: 6

Xaa Xaa Glu Gly Thr Phe Thr Ser Asp Val Ser Ser Tyr Leu Glu Xaa
1               5                   10                  15
```

-continued

```
Xaa Xaa Ala Lys Glu Phe Ile Xaa Trp Leu Val Lys Gly Arg Xaa Xaa
            20                  25                  30


<210> SEQ ID NO 7
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Ala, Gly, Val, Thr, Ile,
      and alpha-methyl-Ala;
<220> FEATURE:
<221> NAME/KEY: MISC_FEATURE
<222> LOCATION: (15)..(15)
<223> OTHER INFORMATION: Xaa at position 15 is Glu, Gln, Ala, Thr, Ser,
      and Gly;
<220> FEATURE:
<221> NAME/KEY: MISC_FEATURE
<222> LOCATION: (21)..(21)
<223> OTHER INFORMATION: Xaa at position 21 is Glu, Gln, Ala, Thr, Ser,
      and Gly;

<400> SEQUENCE: 7

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Gly
            20                  25                  30


<210> SEQ ID NO 8
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (19)..(19)
<223> OTHER INFORMATION: Xaa at position 19 is Lys or Arg;
<220> FEATURE:
<221> NAME/KEY: MOD_RES
<222> LOCATION: (27)..(27)
<223> OTHER INFORMATION: ACETYLATION
<220> FEATURE:
<221> NAME/KEY: MISC_FEATURE
<222> LOCATION: (30)..(30)
<223> OTHER INFORMATION: Xaa at position 30 is Gly;
<220> FEATURE:
<221> NAME/KEY: MOD_RES
<222> LOCATION: (30)..(30)
<223> OTHER INFORMATION: AMIDATION

<400> SEQUENCE: 8

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
            20                  25                  30


<210> SEQ ID NO 9
<211> LENGTH: 39
<212> TYPE: PRT
<213> ORGANISM: Artificial Sequence
<220> FEATURE:
<223> OTHER INFORMATION: synthetic construct
```

-continued

<400> SEQUENCE: 9

```
His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 10
<211> LENGTH: 39
<212> TYPE: PRT
<213> ORGANISM: Artificial Sequence
<220> FEATURE:
<223> OTHER INFORMATION: synthetic construct

<400> SEQUENCE: 10

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 11
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine, or is deleted.
<220> FEATURE:
<221> NAME/KEY: MISC_FEATURE
<222> LOCATION: (2)..(2)
<223> OTHER INFORMATION: Xaa at position 2 is Gly, Ala, or Val;
<220> FEATURE:
<221> NAME/KEY: MISC_FEATURE
<222> LOCATION: (10)..(10)
<223> OTHER INFORMATION: Xaa at position 10 is Leu or Val;
<220> FEATURE:
<221> NAME/KEY: MISC_FEATURE
<222> LOCATION: (12)..(12)
<223> OTHER INFORMATION: Xaa at position 12 is Lys or Ser;
<220> FEATURE:
<221> NAME/KEY: MISC_FEATURE
<222> LOCATION: (13)..(13)
<223> OTHER INFORMATION: Xaa at position 13 is Gln or Tyr;
<220> FEATURE:
<221> NAME/KEY: MISC_FEATURE
<222> LOCATION: (14)..(14)
<223> OTHER INFORMATION: Xaa at position 14 is Met or Leu;
<220> FEATURE:
<221> NAME/KEY: MISC_FEATURE
<222> LOCATION: (16)..(16)
<223> OTHER INFORMATION: Xaa at position 16 is Glu or Gln;
<220> FEATURE:
<221> NAME/KEY: MISC_FEATURE
<222> LOCATION: (17)..(17)
<223> OTHER INFORMATION: Xaa at position 17 is Glu or Gln;
<220> FEATURE:
<221> NAME/KEY: MISC_FEATURE
<222> LOCATION: (19)..(19)
<223> OTHER INFORMATION: Xaa at position 19 is Val or Ala;
<220> FEATURE:
<221> NAME/KEY: MISC_FEATURE
<222> LOCATION: (20)..(20)
<223> OTHER INFORMATION: Xaa at position 20 is Arg or Lys;

<220> FEATURE:
<221> NAME/KEY: MISC_FEATURE
<222> LOCATION: (21)..(21)
<223> OTHER INFORMATION: Xaa at position 21 is Leu or Glu;
<220> FEATURE:
<221> NAME/KEY: MISC_FEATURE
<222> LOCATION: (24)..(24)
<223> OTHER INFORMATION: Xaa at position 24 is Glu or Ala;
<220> FEATURE:
<221> NAME/KEY: MISC_FEATURE
<222> LOCATION: (27)..(27)
<223> OTHER INFORMATION: Xaa at position 27 is Val or Lys;
<220> FEATURE:
<221> NAME/KEY: MISC_FEATURE
<222> LOCATION: (28)..(28)
<223> OTHER INFORMATION: Xaa at position 28 is Asn or Lys;
<220> FEATURE:
<221> NAME/KEY: MISC_FEATURE
<222> LOCATION: (30)..(30)
<223> OTHER INFORMATION: Xaa at position 30 is Gly or Arg; and
<220> FEATURE:
<221> NAME/KEY: MISC_FEATURE
<222> LOCATION: (31)..(31)
<223> OTHER INFORMATION: Xaa at position 31 is Gly, or Pro;
<220> FEATURE:
<221> NAME/KEY: MISC_FEATURE
<222> LOCATION: (32)..(32)
<223> OTHER INFORMATION: Xaa at position 32 is Ser, or is absent.
<220> FEATURE:
<221> NAME/KEY: MISC_FEATURE
<222> LOCATION: (33)..(33)
<223> OTHER INFORMATION: Xaa at position 33 is Ser, or is absent.
<220> FEATURE:
<221> NAME/KEY: MISC_FEATURE
<222> LOCATION: (34)..(34)
<223> OTHER INFORMATION: Xaa at position 34 is Gly, or is absent.
<220> FEATURE:
<221> NAME/KEY: MISC_FEATURE
<222> LOCATION: (35)..(35)
<223> OTHER INFORMATION: Xaa at position 35 is Ala, or is absent.
<220> FEATURE:
<221> NAME/KEY: MISC_FEATURE
<222> LOCATION: (36)..(36)
<223> OTHER INFORMATION: Xaa at position 36 is Pro, or is absent.
<220> FEATURE:
<221> NAME/KEY: MISC_FEATURE
<222> LOCATION: (37)..(37)
<223> OTHER INFORMATION: Xaa at position 37 is Pro, or is absent.
<220> FEATURE:
<221> NAME/KEY: MISC_FEATURE
<222> LOCATION: (38)..(38)
<223> OTHER INFORMATION: Xaa at position 38 is Pro, or is absent.
<220> FEATURE:
<221> NAME/KEY: MISC_FEATURE
<222> LOCATION: (39)..(39)
<223> OTHER INFORMATION: Xaa at position 39 is Pro, or is absent.
<220> FEATURE:
<221> NAME/KEY: MISC_FEATURE
<222> LOCATION: (39)..(39)
<223> OTHER INFORMATION: Xaa at position 39 is Ser, or is absent.

<400> SEQUENCE: 11

```
Xaa Xaa Glu Glu Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Gly Xaa Xaa Xaa
            20                  25                  30

Xaa Xaa Xaa Xaa Xaa Xaa Xaa
        35
```

<210> SEQ ID NO 12
<211> LENGTH: 31
<212> TYPE: PRT
<213> ORGANISM: Artificial Sequence
<220> FEATURE:
<223> OTHER INFORMATION: synthetic construct

```
<220> FEATURE:
<221> NAME/KEY: MISC_FEATURE
<222> LOCATION: (1)..(1)
<223> OTHER INFORMATION: Xaa at position 1 is L-histidine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr;
<220> FEATURE:
<221> NAME/KEY: MISC_FEATURE
<222> LOCATION: (6)..(6)
<223> OTHER INFORMATION: Xaa at position 6 is Phe, Trp, or Tyr;
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      or Tyr;
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, Val;
<220> FEATURE:
<221> NAME/KEY: MISC_FEATURE
<222> LOCATION: (13)..(13)
<223> OTHER INFORMATION: Xaa at position 13 is Tyr, Trp, or Phe;
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp;
<220> FEATURE:
<221> NAME/KEY: MISC_FEATURE
<222> LOCATION: (16)..(16)
<223> OTHER INFORMATION: Xaa at position 16 is Gly, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Val, Ile, or Leu;
<220> FEATURE:
<221> NAME/KEY: MISC_FEATURE
<222> LOCATION: (21)..(21)
<223> OTHER INFORMATION: Xaa at position 21 is Glu, Ile, or Ala;
<220> FEATURE:
<221> NAME/KEY: MISC_FEATURE
<222> LOCATION: (24)..(24)
<223> OTHER INFORMATION: Xaa at position 24 is Ala or Glu;
<220> FEATURE:
<221> NAME/KEY: MISC_FEATURE
<222> LOCATION: (27)..(27)
<223> OTHER INFORMATION: Xaa at position 27 is Val or Ile; and
<220> FEATURE:
<221> NAME/KEY: MOD_RES
<222> LOCATION: (30)..(30)
<223> OTHER INFORMATION: AMIDATION
<220> FEATURE:
<221> NAME/KEY: MISC_FEATURE
<222> LOCATION: (31)..(31)
<223> OTHER INFORMATION: Xaa at position 31 is Gly, His or is absent.

<400> SEQUENCE: 12

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Lys Gly Arg Xaa
            20                  25                  30


<210> SEQ ID NO 13
<211> LENGTH: 616
<212> TYPE: PRT
<213> ORGANISM: Artificial Sequence
<220> FEATURE:
<223> OTHER INFORMATION: synthetic construct

<400> SEQUENCE: 13
```

-continued

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Asp
            20                  25                  30

Ala His Lys Ser Glu Val Ala His Arg Phe Lys Asp Leu Gly Glu Glu
        35                  40                  45

Asn Phe Lys Ala Leu Val Leu Ile Ala Phe Ala Gln Tyr Leu Gln Gln
    50                  55                  60

Cys Pro Phe Glu Asp His Val Lys Leu Val Asn Glu Val Thr Glu Phe
65                  70                  75                  80

Ala Lys Thr Cys Val Ala Asp Glu Ser Ala Glu Asn Cys Asp Lys Ser
                85                  90                  95

Leu His Thr Leu Phe Gly Asp Lys Leu Cys Thr Val Ala Thr Leu Arg
            100                 105                 110

Glu Thr Tyr Gly Glu Met Ala Asp Cys Cys Ala Lys Gln Glu Pro Glu
        115                 120                 125

Arg Asn Glu Cys Phe Leu Gln His Lys Asp Asp Asn Pro Asn Leu Pro
    130                 135                 140

Arg Leu Val Arg Pro Glu Val Asp Val Met Cys Thr Ala Phe His Asp
145                 150                 155                 160

Asn Glu Glu Thr Phe Leu Lys Lys Tyr Leu Tyr Glu Ile Ala Arg Arg
                165                 170                 175

His Pro Tyr Phe Tyr Ala Pro Glu Leu Leu Phe Phe Ala Lys Arg Tyr
            180                 185                 190

Lys Ala Ala Phe Thr Glu Cys Cys Gln Ala Ala Asp Lys Ala Ala Cys
        195                 200                 205

Leu Leu Pro Lys Leu Asp Glu Leu Arg Asp Glu Gly Lys Ala Ser Ser
    210                 215                 220

Ala Lys Gln Arg Leu Lys Cys Ala Ser Leu Gln Lys Phe Gly Glu Arg
225                 230                 235                 240

Ala Phe Lys Ala Trp Ala Val Ala Arg Leu Ser Gln Arg Phe Pro Lys
                245                 250                 255

Ala Glu Phe Ala Glu Val Ser Lys Leu Val Thr Asp Leu Thr Lys Val
            260                 265                 270

His Thr Glu Cys Cys His Gly Asp Leu Leu Glu Cys Ala Asp Asp Arg
        275                 280                 285

Ala Asp Leu Ala Lys Tyr Ile Cys Glu Asn Gln Asp Ser Ile Ser Ser
    290                 295                 300

Lys Leu Lys Glu Cys Cys Glu Lys Pro Leu Leu Glu Lys Ser His Cys
305                 310                 315                 320

Ile Ala Glu Val Glu Asn Asp Glu Met Pro Ala Asp Leu Pro Ser Leu
                325                 330                 335

Ala Ala Asp Phe Val Glu Ser Lys Asp Val Cys Lys Asn Tyr Ala Glu
            340                 345                 350

Ala Lys Asp Val Phe Leu Gly Met Phe Leu Tyr Glu Tyr Ala Arg Arg
        355                 360                 365

His Pro Asp Tyr Ser Val Val Leu Leu Leu Arg Leu Ala Lys Thr Tyr
    370                 375                 380

Glu Thr Thr Leu Glu Lys Cys Cys Ala Ala Ala Asp Pro His Glu Cys
385                 390                 395                 400

Tyr Ala Lys Val Phe Asp Glu Phe Lys Pro Leu Val Glu Glu Pro Gln
                405                 410                 415

Asn Leu Ile Lys Gln Asn Cys Glu Leu Phe Glu Gln Leu Gly Glu Tyr
```

-continued

```
        420                 425                 430

Lys Phe Gln Asn Ala Leu Leu Val Arg Tyr Thr Lys Lys Val Pro Gln
        435                 440                 445

Val Ser Thr Pro Thr Leu Val Glu Val Ser Arg Asn Leu Gly Lys Val
    450                 455                 460

Gly Ser Lys Cys Cys Lys His Pro Glu Ala Lys Arg Met Pro Cys Ala
465                 470                 475                 480

Glu Asp Tyr Leu Ser Val Val Leu Asn Gln Leu Cys Val Leu His Glu
                485                 490                 495

Lys Thr Pro Val Ser Asp Arg Val Thr Lys Cys Cys Thr Glu Ser Leu
            500                 505                 510

Val Asn Arg Arg Pro Cys Phe Ser Ala Leu Glu Val Asp Glu Thr Tyr
        515                 520                 525

Val Pro Lys Glu Phe Asn Ala Glu Thr Phe Thr Phe His Ala Asp Ile
    530                 535                 540

Cys Thr Leu Ser Glu Lys Glu Arg Gln Ile Lys Lys Gln Thr Ala Leu
545                 550                 555                 560

Val Glu Leu Val Lys His Lys Pro Lys Ala Thr Lys Glu Gln Leu Lys
                565                 570                 575

Ala Val Met Asp Asp Phe Ala Ala Phe Val Glu Lys Cys Cys Lys Ala
            580                 585                 590

Asp Asp Lys Glu Thr Cys Phe Ala Glu Glu Gly Lys Lys Leu Val Ala
        595                 600                 605

Ala Ser Gln Ala Ala Leu Gly Leu
    610                 615


<210> SEQ ID NO 14
<211> LENGTH: 631
<212> TYPE: PRT
<213> ORGANISM: Artificial Sequence
<220> FEATURE:
<223> OTHER INFORMATION: synthetic construct

<400> SEQUENCE: 14

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Gly Ser Gly Gly Gly Gly Ser Gly Gly Gly Gly Ser Asp Ala
        35                  40                  45

His Lys Ser Glu Val Ala His Arg Phe Lys Asp Leu Gly Glu Glu Asn
    50                  55                  60

Phe Lys Ala Leu Val Leu Ile Ala Phe Ala Gln Tyr Leu Gln Gln Cys
65                  70                  75                  80

Pro Phe Glu Asp His Val Lys Leu Val Asn Glu Val Thr Glu Phe Ala
                85                  90                  95

Lys Thr Cys Val Ala Asp Glu Ser Ala Glu Asn Cys Asp Lys Ser Leu
            100                 105                 110

His Thr Leu Phe Gly Asp Lys Leu Cys Thr Val Ala Thr Leu Arg Glu
        115                 120                 125

Thr Tyr Gly Glu Met Ala Asp Cys Cys Ala Lys Gln Glu Pro Glu Arg
    130                 135                 140

Asn Glu Cys Phe Leu Gln His Lys Asp Asp Asn Pro Asn Leu Pro Arg
145                 150                 155                 160

Leu Val Arg Pro Glu Val Asp Val Met Cys Thr Ala Phe His Asp Asn
```

-continued

```
                165                 170                 175

Glu Glu Thr Phe Leu Lys Lys Tyr Leu Tyr Glu Ile Ala Arg Arg His
            180                 185                 190

Pro Tyr Phe Tyr Ala Pro Glu Leu Leu Phe Phe Ala Lys Arg Tyr Lys
        195                 200                 205

Ala Ala Phe Thr Glu Cys Cys Gln Ala Ala Asp Lys Ala Ala Cys Leu
    210                 215                 220

Leu Pro Lys Leu Asp Glu Leu Arg Asp Glu Gly Lys Ala Ser Ser Ala
225                 230                 235                 240

Lys Gln Arg Leu Lys Cys Ala Ser Leu Gln Lys Phe Gly Glu Arg Ala
                245                 250                 255

Phe Lys Ala Trp Ala Val Ala Arg Leu Ser Gln Arg Phe Pro Lys Ala
            260                 265                 270

Glu Phe Ala Glu Val Ser Lys Leu Val Thr Asp Leu Thr Lys Val His
        275                 280                 285

Thr Glu Cys Cys His Gly Asp Leu Leu Glu Cys Ala Asp Asp Arg Ala
    290                 295                 300

Asp Leu Ala Lys Tyr Ile Cys Glu Asn Gln Asp Ser Ile Ser Ser Lys
305                 310                 315                 320

Leu Lys Glu Cys Cys Glu Lys Pro Leu Leu Glu Lys Ser His Cys Ile
                325                 330                 335

Ala Glu Val Glu Asn Asp Glu Met Pro Ala Asp Leu Pro Ser Leu Ala
            340                 345                 350

Ala Asp Phe Val Glu Ser Lys Asp Val Cys Lys Asn Tyr Ala Glu Ala
        355                 360                 365

Lys Asp Val Phe Leu Gly Met Phe Leu Tyr Glu Tyr Ala Arg Arg His
    370                 375                 380

Pro Asp Tyr Ser Val Val Leu Leu Leu Arg Leu Ala Lys Thr Tyr Glu
385                 390                 395                 400

Thr Thr Leu Glu Lys Cys Cys Ala Ala Ala Asp Pro His Glu Cys Tyr
                405                 410                 415

Ala Lys Val Phe Asp Glu Phe Lys Pro Leu Val Glu Glu Pro Gln Asn
            420                 425                 430

Leu Ile Lys Gln Asn Cys Glu Leu Phe Glu Gln Leu Gly Glu Tyr Lys
        435                 440                 445

Phe Gln Asn Ala Leu Leu Val Arg Tyr Thr Lys Lys Val Pro Gln Val
    450                 455                 460

Ser Thr Pro Thr Leu Val Glu Val Ser Arg Asn Leu Gly Lys Val Gly
465                 470                 475                 480

Ser Lys Cys Cys Lys His Pro Glu Ala Lys Arg Met Pro Cys Ala Glu
                485                 490                 495

Asp Tyr Leu Ser Val Val Leu Asn Gln Leu Cys Val Leu His Glu Lys
            500                 505                 510

Thr Pro Val Ser Asp Arg Val Thr Lys Cys Cys Thr Glu Ser Leu Val
        515                 520                 525

Asn Arg Arg Pro Cys Phe Ser Ala Leu Glu Val Asp Glu Thr Tyr Val
    530                 535                 540

Pro Lys Glu Phe Asn Ala Glu Thr Phe Thr Phe His Ala Asp Ile Cys
545                 550                 555                 560

Thr Leu Ser Glu Lys Glu Arg Gln Ile Lys Lys Gln Thr Ala Leu Val
                565                 570                 575

Glu Leu Val Lys His Lys Pro Lys Ala Thr Lys Glu Gln Leu Lys Ala
            580                 585                 590
```

```
Val Met Asp Asp Phe Ala Ala Phe Val Glu Lys Cys Cys Lys Ala Asp
        595                 600                 605

Asp Lys Glu Thr Cys Phe Ala Glu Glu Gly Lys Lys Leu Val Ala Ala
    610                 615                 620

Ser Gln Ala Ala Leu Gly Leu
625                 630


<210> SEQ ID NO 15
<211> LENGTH: 640
<212> TYPE: PRT
<213> ORGANISM: Artificial Sequence
<220> FEATURE:
<223> OTHER INFORMATION: synthetic construct

<400> SEQUENCE: 15

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Gly Gly Gly Gly Gly Ser Gly Gly Gly
        35                  40                  45

Gly Ser Gly Gly Gly Gly Ser Asp Ala His Lys Ser Glu Val Ala His
    50                  55                  60

Arg Phe Lys Asp Leu Gly Glu Glu Asn Phe Lys Ala Leu Val Leu Ile
65                  70                  75                  80

Ala Phe Ala Gln Tyr Leu Gln Gln Cys Pro Phe Glu Asp His Val Lys
                85                  90                  95

Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
        115                 120                 125

Leu Cys Thr Val Ala Thr Leu Arg Glu Thr Tyr Gly Glu Met Ala Asp
    130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
        195                 200                 205

Leu Leu Phe Phe Ala Lys Arg Tyr Lys Ala Ala Phe Thr Glu Cys Cys
    210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
    290                 295                 300

Leu Leu Glu Cys Ala Asp Asp Arg Ala Asp Leu Ala Lys Tyr Ile Cys
305                 310                 315                 320
```

-continued

```
Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
    370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
    450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
                485                 490                 495

Glu Ala Lys Arg Met Pro Cys Ala Glu Asp Tyr Leu Ser Val Val Leu
            500                 505                 510

Asn Gln Leu Cys Val Leu His Glu Lys Thr Pro Val Ser Asp Arg Val
        515                 520                 525

Thr Lys Cys Cys Thr Glu Ser Leu Val Asn Arg Arg Pro Cys Phe Ser
    530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
                565                 570                 575

Gln Ile Lys Lys Gln Thr Ala Leu Val Glu Leu Val Lys His Lys Pro
            580                 585                 590

Lys Ala Thr Lys Glu Gln Leu Lys Ala Val Met Asp Asp Phe Ala Ala
        595                 600                 605

Phe Val Glu Lys Cys Cys Lys Ala Asp Asp Lys Glu Thr Cys Phe Ala
    610                 615                 620

Glu Glu Gly Lys Lys Leu Val Ala Ala Ser Gln Ala Ala Leu Gly Leu
625                 630                 635                 640


<210> SEQ ID NO 16
<211> LENGTH: 624
<212> TYPE: PRT
<213> ORGANISM: Artificial Sequence
<220> FEATURE:
<223> OTHER INFORMATION: synthetic construct

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asp Ala His Lys Ser Glu Val Ala His
        35                  40                  45
```

-continued

```
Arg Phe Lys Asp Leu Gly Glu Glu Asn Phe Lys Ala Leu Val Leu Ile
    50                  55                  60

Ala Phe Ala Gln Tyr Leu Gln Gln Cys Pro Phe Glu Asp His Val Lys
65                  70                  75                  80

Leu Val Asn Glu Val Thr Glu Phe Ala Lys Thr Cys Val Ala Asp Glu
                85                  90                  95

Ser Ala Glu Asn Cys Asp Lys Ser Leu His Thr Leu Phe Gly Asp Lys
            100                 105                 110

Leu Cys Thr Val Ala Thr Leu Arg Glu Thr Tyr Gly Glu Met Ala Asp
        115                 120                 125

Cys Cys Ala Lys Gln Glu Pro Glu Arg Asn Glu Cys Phe Leu Gln His
    130                 135                 140

Lys Asp Asp Asn Pro Asn Leu Pro Arg Leu Val Arg Pro Glu Val Asp
145                 150                 155                 160

Val Met Cys Thr Ala Phe His Asp Asn Glu Glu Thr Phe Leu Lys Lys
                165                 170                 175

Tyr Leu Tyr Glu Ile Ala Arg Arg His Pro Tyr Phe Tyr Ala Pro Glu
            180                 185                 190

Leu Leu Phe Phe Ala Lys Arg Tyr Lys Ala Ala Phe Thr Glu Cys Cys
        195                 200                 205

Gln Ala Ala Asp Lys Ala Ala Cys Leu Leu Pro Lys Leu Asp Glu Leu
    210                 215                 220

Arg Asp Glu Gly Lys Ala Ser Ser Ala Lys Gln Arg Leu Lys Cys Ala
225                 230                 235                 240

Ser Leu Gln Lys Phe Gly Glu Arg Ala Phe Lys Ala Trp Ala Val Ala
                245                 250                 255

Arg Leu Ser Gln Arg Phe Pro Lys Ala Glu Phe Ala Glu Val Ser Lys
            260                 265                 270

Leu Val Thr Asp Leu Thr Lys Val His Thr Glu Cys Cys His Gly Asp
        275                 280                 285

Leu Leu Glu Cys Ala Asp Asp Arg Ala Asp Leu Ala Lys Tyr Ile Cys
    290                 295                 300

Glu Asn Gln Asp Ser Ile Ser Ser Lys Leu Lys Glu Cys Cys Glu Lys
305                 310                 315                 320

Pro Leu Leu Glu Lys Ser His Cys Ile Ala Glu Val Glu Asn Asp Glu
                325                 330                 335

Met Pro Ala Asp Leu Pro Ser Leu Ala Ala Asp Phe Val Glu Ser Lys
            340                 345                 350

Asp Val Cys Lys Asn Tyr Ala Glu Ala Lys Asp Val Phe Leu Gly Met
        355                 360                 365

Phe Leu Tyr Glu Tyr Ala Arg Arg His Pro Asp Tyr Ser Val Val Leu
    370                 375                 380

Leu Leu Arg Leu Ala Lys Thr Tyr Glu Thr Thr Leu Glu Lys Cys Cys
385                 390                 395                 400

Ala Ala Ala Asp Pro His Glu Cys Tyr Ala Lys Val Phe Asp Glu Phe
                405                 410                 415

Lys Pro Leu Val Glu Glu Pro Gln Asn Leu Ile Lys Gln Asn Cys Glu
            420                 425                 430

Leu Phe Glu Gln Leu Gly Glu Tyr Lys Phe Gln Asn Ala Leu Leu Val
        435                 440                 445

Arg Tyr Thr Lys Lys Val Pro Gln Val Ser Thr Pro Thr Leu Val Glu
    450                 455                 460
```

-continued

```
Val Ser Arg Asn Leu Gly Lys Val Gly Ser Lys Cys Cys Lys His Pro
465                 470                 475                 480

Glu Ala Lys Arg Met Pro Cys Ala Glu Asp Tyr Leu Ser Val Val Leu
                485                 490                 495

Asn Gln Leu Cys Val Leu His Glu Lys Thr Pro Val Ser Asp Arg Val
            500                 505                 510

Thr Lys Cys Cys Thr Glu Ser Leu Val Asn Arg Arg Pro Cys Phe Ser
        515                 520                 525

Ala Leu Glu Val Asp Glu Thr Tyr Val Pro Lys Glu Phe Asn Ala Glu
    530                 535                 540

Thr Phe Thr Phe His Ala Asp Ile Cys Thr Leu Ser Glu Lys Glu Arg
545                 550                 555                 560

Gln Ile Lys Lys Gln Thr Ala Leu Val Glu Leu Val Lys His Lys Pro
                565                 570                 575

Lys Ala Thr Lys Glu Gln Leu Lys Ala Val Met Asp Asp Phe Ala Ala
            580                 585                 590

Phe Val Glu Lys Cys Cys Lys Ala Asp Asp Lys Glu Thr Cys Phe Ala
        595                 600                 605

Glu Glu Gly Lys Lys Leu Val Ala Ala Ser Gln Ala Ala Leu Gly Leu
    610                 615                 620


<210> SEQ ID NO 17
<211> LENGTH: 640
<212> TYPE: PRT
<213> ORGANISM: Artificial Sequence
<220> FEATURE:
<223> OTHER INFORMATION: synthetic construct

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Gly Ser Gly Gly Gly
        35                  40                  45

Gly Ser Gly Gly Gly Gly Ser Asp Ala His Lys Ser Glu Val Ala His
    50                  55                  60

Arg Phe Lys Asp Leu Gly Glu Glu Asn Phe Lys Ala Leu Val Leu Ile
65                  70                  75                  80

Ala Phe Ala Gln Tyr Leu Gln Gln Cys Pro Phe Glu Asp His Val Lys
                85                  90                  95

Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
        115                 120                 125

Leu Cys Thr Val Ala Thr Leu Arg Glu Thr Tyr Gly Glu Met Ala Asp
    130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
        195                 200                 205
```

-continued

```
Leu Leu Phe Phe Ala Lys Arg Tyr Lys Ala Ala Phe Thr Glu Cys Cys
    210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
    290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
    370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
    450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
                485                 490                 495

Glu Ala Lys Arg Met Pro Cys Ala Glu Asp Tyr Leu Ser Val Val Leu
            500                 505                 510

Asn Gln Leu Cys Val Leu His Glu Lys Thr Pro Val Ser Asp Arg Val
        515                 520                 525

Thr Lys Cys Cys Thr Glu Ser Leu Val Asn Arg Arg Pro Cys Phe Ser
    530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
                565                 570                 575

Gln Ile Lys Lys Gln Thr Ala Leu Val Glu Leu Val Lys His Lys Pro
            580                 585                 590

Lys Ala Thr Lys Glu Gln Leu Lys Ala Val Met Asp Asp Phe Ala Ala
        595                 600                 605

Phe Val Glu Lys Cys Cys Lys Ala Asp Asp Lys Glu Thr Cys Phe Ala
    610                 615                 620

Glu Glu Gly Lys Lys Leu Val Ala Ala Ser Gln Ala Ala Leu Gly Leu
```

-continued 625 630 635 640

<210> SEQ ID NO 18
<211> LENGTH: 264
<212> TYPE: PRT
<213> ORGANISM: Artificial Sequence
<220> FEATURE:
<223> OTHER INFORMATION: synthetic construct

<400> SEQUENCE: 18

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260
```

<210> SEQ ID NO 19
<211> LENGTH: 272
<212> TYPE: PRT
<213> ORGANISM: Artificial Sequence
<220> FEATURE:
<223> OTHER INFORMATION: synthetic construct

<400> SEQUENCE: 19

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ser
            20                  25                  30
```

-continued

```
Ser Gly Ala Pro Pro Pro Ser Ala Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270


<210> SEQ ID NO 20
<211> LENGTH: 264
<212> TYPE: PRT
<213> ORGANISM: Artificial Sequence
<220> FEATURE:
<223> OTHER INFORMATION: synthetic construct

<400> SEQUENCE: 20

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ala
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125
```

-continued

```
Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260


<210> SEQ ID NO 21
<211> LENGTH: 272
<212> TYPE: PRT
<213> ORGANISM: Artificial Sequence
<220> FEATURE:
<223> OTHER INFORMATION: synthetic construct

<400> SEQUENCE: 21

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Ala Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220
```

-continued

```
Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

<210> SEQ ID NO 22
<211> LENGTH: 272
<212> TYPE: PRT
<213> ORGANISM: Artificial Sequence
<220> FEATURE:
<223> OTHER INFORMATION: synthetic construct

<400> SEQUENCE: 22

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Ser Ser Gly Ala Ala Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

<210> SEQ ID NO 23
<211> LENGTH: 287
<212> TYPE: PRT
<213> ORGANISM: Artificial Sequence
<220> FEATURE:
<223> OTHER INFORMATION: synthetic construct

<400> SEQUENCE: 23

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Ala Glu Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285


<210> SEQ ID NO 24
<211> LENGTH: 284
<212> TYPE: PRT
<213> ORGANISM: Artificial Sequence
<220> FEATURE:
<223> OTHER INFORMATION: synthetic construct

<400> SEQUENCE: 24

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Ala Glu Ser Lys Tyr Gly Pro Pro Cys Pro
    50                  55                  60

Ser Cys Pro Ala Pro Glu Phe Leu Gly Gly Pro Ser Val Phe Leu Phe
65                  70                  75                  80
```

-continued

```
Pro Pro Lys Pro Lys Asp Thr Leu Met Ile Ser Arg Thr Pro Glu Val
                85                  90                  95

Thr Cys Val Val Val Asp Val Ser Gln Glu Asp Pro Glu Val Gln Phe
            100                 105                 110

Asn Trp Tyr Val Asp Gly Val Glu Val His Asn Ala Lys Thr Lys Pro
        115                 120                 125

Arg Glu Glu Gln Phe Asn Ser Thr Tyr Arg Val Val Ser Val Leu Thr
    130                 135                 140

Val Leu His Gln Asp Trp Leu Asn Gly Lys Glu Tyr Lys Cys Lys Val
145                 150                 155                 160

Ser Asn Lys Gly Leu Pro Ser Ser Ile Glu Lys Thr Ile Ser Lys Ala
                165                 170                 175

Lys Gly Gln Pro Arg Glu Pro Gln Val Tyr Thr Leu Pro Pro Ser Gln
            180                 185                 190

Glu Glu Met Thr Lys Asn Gln Val Ser Leu Thr Cys Leu Val Lys Gly
        195                 200                 205

Phe Tyr Pro Ser Asp Ile Ala Val Glu Trp Glu Ser Asn Gly Gln Pro
    210                 215                 220

Glu Asn Asn Tyr Lys Thr Thr Pro Pro Val Leu Asp Ser Asp Gly Ser
225                 230                 235                 240

Phe Phe Leu Tyr Ser Arg Leu Thr Val Asp Lys Ser Arg Trp Gln Glu
                245                 250                 255

Gly Asn Val Phe Ser Cys Ser Val Met His Glu Ala Leu His Asn His
            260                 265                 270

Tyr Thr Gln Lys Ser Leu Ser Leu Ser Leu Gly Lys
        275                 280
```

<210> SEQ ID NO 25
<211> LENGTH: 302
<212> TYPE: PRT
<213> ORGANISM: Artificial Sequence
<220> FEATURE:
<223> OTHER INFORMATION: synthetic construct

<400> SEQUENCE: 25

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Gly Gly Gly Gly Ser Gly Gly Gly Gly Ser
    50                  55                  60

Gly Gly Gly Gly Ser Ala Glu Pro Lys Ser Cys Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
145                 150                 155                 160
```

```
Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
    210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300
```

<210> SEQ ID NO 26
<211> LENGTH: 294
<212> TYPE: PRT
<213> ORGANISM: Artificial Sequence
<220> FEATURE:
<223> OTHER INFORMATION: synthetic construct

<400> SEQUENCE: 26

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Gly
            20                  25                  30

Gly Gly Gly Ser Gly Gly Gly Gly Ser Gly Gly Gly Gly Ser Gly Gly
        35                  40                  45

Gly Gly Ser Gly Gly Gly Gly Ser Gly Gly Gly Gly Ser Ala Glu Pro
    50                  55                  60

Lys Ser Cys Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220
```

```
Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290


<210> SEQ ID NO 27
<211> LENGTH: 280
<212> TYPE: PRT
<213> ORGANISM: Artificial Sequence
<220> FEATURE:
<223> OTHER INFORMATION: synthetic construct

<400> SEQUENCE: 27

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser Ser Ser Gly Ala Pro Pro Pro Ser Ala
        35                  40                  45

Glu Pro Lys Ser Cys Asp Lys Thr His Thr Cys Pro Pro Cys Pro Ala
    50                  55                  60

Pro Glu Leu Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
        115                 120                 125

Tyr Asn Ser Thr Tyr Arg Val Val Ser Val Leu Thr Val Leu His Gln
    130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
                165                 170                 175

Arg Glu Pro Gln Val Tyr Thr Leu Pro Pro Ser Arg Glu Glu Met Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Val Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly Lys
        275                 280
```

```
<210> SEQ ID NO 28
<211> LENGTH: 287
<212> TYPE: PRT
<213> ORGANISM: Artificial Sequence
<220> FEATURE:
<223> OTHER INFORMATION: synthetic construct

<400> SEQUENCE: 28

His Gly Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Arg Gly Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Ala Glu Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285


<210> SEQ ID NO 29
<211> LENGTH: 272
<212> TYPE: PRT
<213> ORGANISM: Artificial Sequence
<220> FEATURE:
<223> OTHER INFORMATION: synthetic construct

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

```
            20                  25                  30

Ser Gly Ala Pro Pro Pro Ser Ala Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270


<210> SEQ ID NO 30
<211> LENGTH: 272
<212> TYPE: PRT
<213> ORGANISM: Artificial Sequence
<220> FEATURE:
<223> OTHER INFORMATION: synthetic construct

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Ser Ser Gly Ala Ala Glu Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
```

-continued

```
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270


<210> SEQ ID NO 31
<211> LENGTH: 287
<212> TYPE: PRT
<213> ORGANISM: Artificial Sequence
<220> FEATURE:
<223> OTHER INFORMATION: synthetic construct

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Ala Glu Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
```

-continued

```
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285


<210> SEQ ID NO 32
<211> LENGTH: 232
<212> TYPE: PRT
<213> ORGANISM: Homo sapiens

<400> SEQUENCE: 32

Ala Glu Pro Lys Ser Cys Asp Lys Thr His Thr Cys Pro Pro Cys Pro
1               5                   10                  15

Ala Pro Glu Lys Gly Gly Pro Ser Val Phe Leu Phe Pro Pro Lys Pro
            20                  25                  30

Lys Asp Thr Lys Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 33
<211> LENGTH: 703
<212> TYPE: DNA
<213> ORGANISM: Homo sapiens

<400> SEQUENCE: 33

gagcccaaat cttgtgacaa aactcacaca tgcccaccgt gcccagcacc tgaactcctg      60

gggggaccgt cagtcttcct cttcccccca aaacccaagg acaccctcat gatctcccgg     120
```

-continued

```
acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc cagcccccat cgagaaaacc    360

atctccaaag ccaaagggca gccccgagaa ccacaggtgt acaccctgcc cccatcccgg    420

gaggagatga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctatagca agctcaccgt ggacaagagc    600

aggtggcagc aggggaacgt cttctcatgc tccgtgatgc atgaggctct gcacaaccac    660

tacacgcaga agagcctctc cctgtctccg ggtaaatgat agt                      703
```

<210> SEQ ID NO 34
<211> LENGTH: 585
<212> TYPE: PRT
<213> ORGANISM: Homo sapiens

<400> SEQUENCE: 34

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

-continued

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Asn Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 35
<211> LENGTH: 1762
<212> TYPE: DNA
<213> ORGANISM: Homo sapiens

<400> SEQUENCE: 35

```
gatgcgcaca agagtgaggt tgctcatcgg tttaaagatt tgggagaaga aaatttcaaa      60

gccttggtgt tgattgcctt tgctcagtat cttcagcagt gtccatttga agatcatgta     120

aaattagtga atgaagtaac tgaatttgca aaaacatgtg ttgctgatga gtcagctgaa     180

aattgtgaca aatcacttca taccctttttt ggagacaaat tatgcacagt tgcaactctt     240

cgtgaaacct atggtgaaat ggctgactgc tgtgcaaaac aagaacctga gagaaatgaa     300

tgcttcttgc aacacaaaga tgacaaccca aacctccccc gattggtgag accagaggtt     360
```

-continued

```
gatgtgatgt gcactgcttt tcatgacaat gaagagacat ttttgaaaaa atacttatat    420

gaaattgcca gaagacatcc ttacttttat gccccggaac tccttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagaag gcatcctgat   1020

tactctgtcg tgctgctgct gagacttgcc aagacatatg aaaccactct agagaagtgc   1080

tgtgccgctg cagatcctca tgaatgctat gccaaagtgt tcgatgaatt taaacctctt   1140

gtggaagagc ctcagaattt aatcaaacaa aattgtgagc tttttgagca gcttggagag   1200

tacaaattcc agaatgcgct attagttcgt tacaccaaga aagtacccca agtgtcaact   1260

ccaactcttg tagaggtctc aagaaaccta ggaaaagtgg gcagcaaatg ttgtaaacat   1320

cctgaagcaa aaagaatgcc ctgtgcagaa gactatctat ccgtggtcct gaaccagtta   1380

tgtgtgttgc atgagaaaac gccagtaagt gacagagtca ccaaatgctg cacagaatcc   1440

ttggtgaaca ggcgaccatg cttttcagct ctggaagtcg atgaaacata cgttcccaaa   1500

gagtttaatg ctgaaacatt caccttccat gcagatatat gcacactttc tgagaaggag   1560

agacaaatca agaaacaaac tgcacttgtt gagctcgtga aacacaagcc caaggcaaca   1620

aaagagcaac tgaaagctgt tatggatgat ttcgcagctt ttgtagagaa gtgctgcaag   1680

gctgacgata aggagacctg ctttgccgag gagggtaaaa aacttgttgc tgcaagtcaa   1740

gctgccttag gcttataatg ac                                            1762
```

GLP-1 FUSION PROTEINS

This is the national phase application, under 35 USC 371, for PCT/US01/43165, filed Nov. 29, 2001, which claims the priority of U.S. provisional application No. 60/251,954, filed Dec. 7, 2000.

The present invention relates to glucagon-like peptides including analogs and derivatives thereof fused to proteins that have the effect of extending the in vivo half-life of the peptides. These fusion proteins can be used to treat non-insulin dependent diabetes mellitus as well as a variety of other conditions.

Glucagon-Like Peptide 1 (GLP-1) is a 37 amino acid peptide that is secreted by the L-cells of the intestine in response to food ingestion. It has been found to stimulate insulin secretion (insulinotropic action), thereby causing glucose uptake by cells and decreased serum glucose levels [see, e.g., Mojsov, S., (1992) *Int. J. Peptide Protein Research*, 40:333-343]. However, GLP-1 is poorly active. A subsequent endogenous cleavage between the $6^{th}$ and $7^{th}$ position produces a more potent biologically active GLP-1 (7-37)OH peptide. Numerous GLP-1 analogs and derivatives are known and are referred to herein as "GLP-1 compounds." These GLP-1 analogs include the Exendins which are peptides found in the venom of the GILA-monster. The Exendins have sequence homology to native GLP-1 and can bind the GLP-1 receptor and initiate the signal transduction cascade responsible for the numerous activities that have been attributed to GLP-1(7-37)OH.

GLP-1 compounds have a variety of physiologically significant activities. For example, GLP-1 has been shown to stimulate insulin release, lower glucagon secretion, inhibit gastric emptying, and enhance glucose utilization. [Nauck, M. A., et al. (1993) *Diabetologia* 36:741-744; Gutniak, M., et al. (1992) *New England J. of Med.* 326:1316-1322; Nauck, M. A., et al., (1993) *J. Clin. Invest.* 91:301-307].

GLP-1 shows the greatest promise as a treatment for non-insulin dependent diabetes mellitus (NIDDM). There are numerous oral drugs on the market to treat the insulin resistance associated with NIDDM. As the disease progresses, however, patients must move to treatments that stimulate the release of insulin and eventually to treatments that involve injections of insulin. Current drugs which stimulate the release of insulin, however, can also cause hypoglycemia as can the actual administration of insulin. GLP-1 activity, however, is controlled by blood glucose levels. When levels drop to a certain threshold level, GLP-1 is not active. Thus, there is no risk of hypoglycemia associated with treatment involving GLP-1.

However, the usefulness of therapy involving GLP-1 peptides has been limited by their fast clearance and short half-lives. For example, GLP-1(7-37) has a serum half-life of only 3 to 5 minutes. GLP-1(7-36) amide has a time action of about 50 minutes when administered subcutaneously. Even analogs and derivatives that are resistant to endogenous protease cleavage, do not have half-lives long enough to avoid repeated administrations over a 24 hour period. Fast clearance of a therapeutic agent is inconvenient in cases where it is desired to maintain a high blood level of the agent over a prolonged period of time since repeated administrations will then be necessary. Furthermore, a long-acting compound is particularly important for diabetic patients whose past treatment regimen has involved taking only oral medication. These patients often have an extremely difficult time transitioning to a regimen that involves multiple injections of medication.

The present invention overcomes the problems associated with delivering a compound that has a short plasma half-life. The compounds of the present invention encompass GLP-1 compounds fused to another protein with a long circulating half-life such as the Fc portion of an immunoglobulin or albumin.

Generally, small therapeutic peptides are difficult to manipulate because even slight changes in their structure can affect stability and/or biological activity. This has been especially true for GLP-1 compounds currently in been especially true for GLP-1 compounds currently in undergo a conformational change from a primarily alpha helix structure to a primarily beta sheet structure. This beta sheet form results in aggregated material that is thought to be inactive. It was, therefore, surprising that biologically active GLP-1 fusion proteins with increased half-lives could be developed. This was especially unexpected given the difficulty of working with GLP-1(7-37)OH alone and the large size of the fusion partner relative to the small GLP-1 peptide attached.

Compounds of the present invention include heterologous fusion proteins comprising a first polypeptide with a N-terminus and a C-terminus fused to a second polypeptide with a N-terminus and a C-terminus wherein the first polypeptide is a GLP-1 compound and the second polypeptide is selected from the group consisting of a) human albumin;

b) human albumin analogs; and c) fragments of human albumin, and wherein the C-terminus of the first polypeptide is fused to the N-terminus of the second polypeptide.

Compounds of the present invention also include a heterologous fusion protein comprising a first polypeptide with a N-terminus and a C-terminus fused to a second polypeptide with a N-terminus and a C-terminus wherein the first polypeptide is a GLP-1 compound and the second polypeptide is selected from the group consisting of a) human albumin;

b) human albumin analogs; and c) fragments of human albumin, and wherein the C-terminus of the first polypeptide is fused to the N-terminus of the second polypeptide via a peptide linker. It is preferred that the peptide linker is selected from the group consisting of:

a) a glycine rich peptide;

b) a peptide having the sequence $[\text{Gly-Gly-Gly-Gly-Ser}]_n$ where n is 1, 2, 3, 4, 5 or 6; and c) a peptide having the sequence $[\text{Gly-Gly-Gly-Gly-Ser}]_3$.

Additional compounds of the present invention include a heterologous fusion protein comprising a first polypeptide with a N-terminus and a C-terminus fused to a second polypeptide with a N-terminus and a C-terminus wherein the first polypeptide is a GLP-1 compound and the second polypeptide is selected from the group consisting of a) the Fc portion of an immunoglobulin;

b) an analog of the Fc portion of an immunoglobulin; and c) fragments of the Fc portion of an immunoglobulin, and wherein the C-terminus of the first polypeptide is fused to the N-terminus of the second polypeptide. The GLP-1 compound may be fused to the second polypeptide via a peptide linker. It is preferable that the peptide linker is selected from the group consisting of:

a) a glycine rich peptide;

b) a peptide having the sequence $[\text{Gly-Gly-Gly-Gly-Ser}]_n$ where n is 1, 2, 3, 4, 5 or 6; and c) a peptide having the sequence $[\text{Gly-Gly-Gly-Gly-Ser}]_3$.

It is generally preferred that the GLP-1 compound that is part of the heterologous fusion protein have no more than 6 amino acids that are different from the corresponding amino acid in GLP-1(7-37)OH, GLP-1(7-36)OH, or Exendin-4. It is even more preferred that the GLP-1 compound have no more than 5 amino acids that differ from the corresponding amino acid in GLP-1(7-37)OH, GLP-1(7-36)OH, or Exendin-4. It is most preferred that the GLP-1 compound have no more than 4, 3, or 2 amino acids that differ from the corresponding amino acid in GLP-1(7-37)OH, GLP-1(7-36) OH, or Exendin-4. Preferably, a GLP-1 compound that is part of the heterologous fusion protein has glycine or valine at position 8.

The present invention also includes polynucleotides encoding the heterologous fusion protein described herein, vectors comprising these polynucleotides and host cells transfected or transformed with the vectors described herein. Also included is a process for producing a heterologous fusion protein comprising the steps of transcribing and translating a polynucleotide described herein under conditions wherein the heterolgous fusion protein is expressed in detectable amounts.

The present invention also encompasses a method for normalizing blood glucose levels in a mammal in need thereof comprising the administration of a therapeutically effective amount of a heterologous fusion protein described herein.

The invention is further illustrated with reference to the following drawings:

FIG. 1: IgG1 Fc amino acid sequence encompassing the hinge region, CH2 and CH3 domains.

FIG. 2: Human serum albumin amino acid sequence.

FIG. 3: A. SDS-PAGE gel and immunoblot of same gel illustrating the molecular weight of IgG1-Fc and GLP-1-Fc fusion proteins (Lane 1, MW standards; Lane 2, Purified Fc; illustrating the molecular weight of IgG1-Fc and GLP-1-Fc 5, Exendin-4-Fc) B. SDS-PAGE gel and immunoblot of same gel illustrating the molecular weight of human HSA and GLP-1-HSA fusion proteins (Lane 1, MW standards; Lane 2, Purified HSA; lane 3, Mock transfected media; Lane 4, Val$^8$-GLP-1-HSA; Lane 5, Val$^8$-GLP-1-[Gly-Gly-Gly-Gly-Ser]$_3$-HSA; Lane 6, Exendin-4-HSA; Lane 7, Exendin-4-[Gly-Gly-Gly-Gly-Ser]$_3$-HSA).

FIG. 4: SDS-PAGE gel of purified Fc, albumin, and GLP-1 fusion proteins (Lane 1, MW standards; Lane 2, puridied Fc; Lane 3, Val8-GLP-1-Fc; Lane 4, Exendin-4-Fc; Lane 5, MW standard; Lane 6, Val8-GLP-1-HSA; Lane 7, Exendin-4-HSA; Lane 8, Exendin-4-[Gly-Gly-Gly-Gly-Ser]$_3$-HSA).

Figure 5:
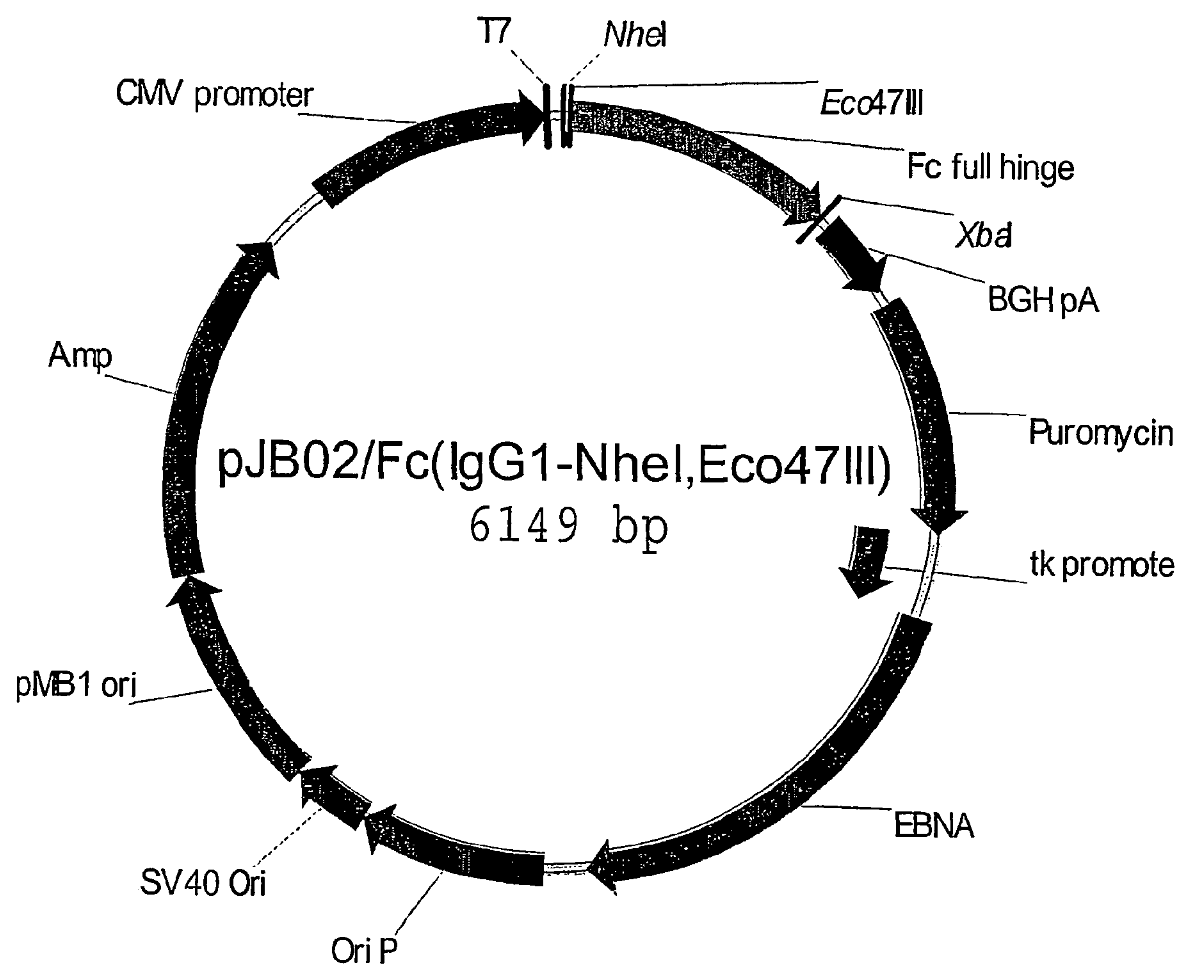

FIG. 5: Expression cloning vector containing the Fc regions illustrated in FIG. 1.

Figure 6:
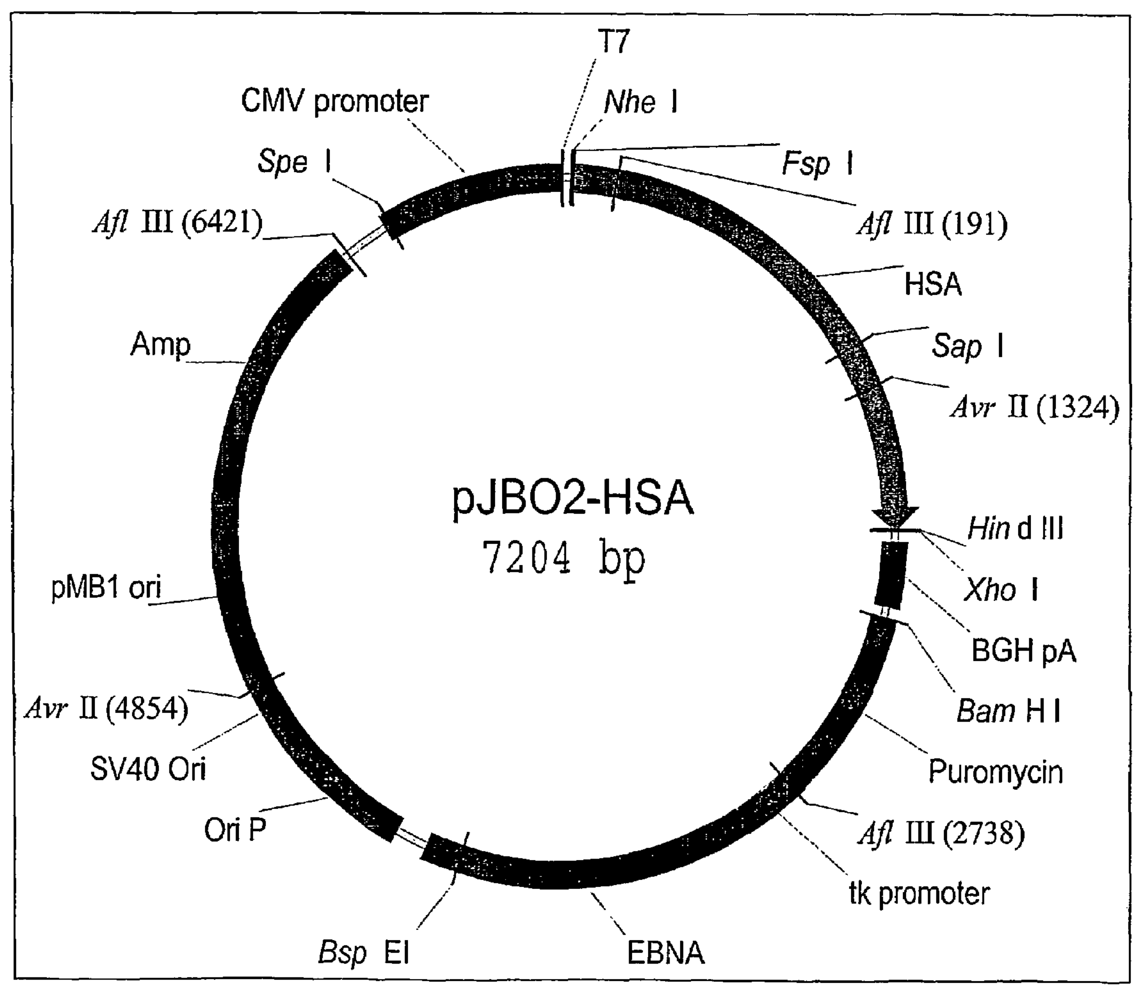

FIG. 6: Expression cloning vector containing the albumin sequence illustrated in FIG. 2.

Figure 7:
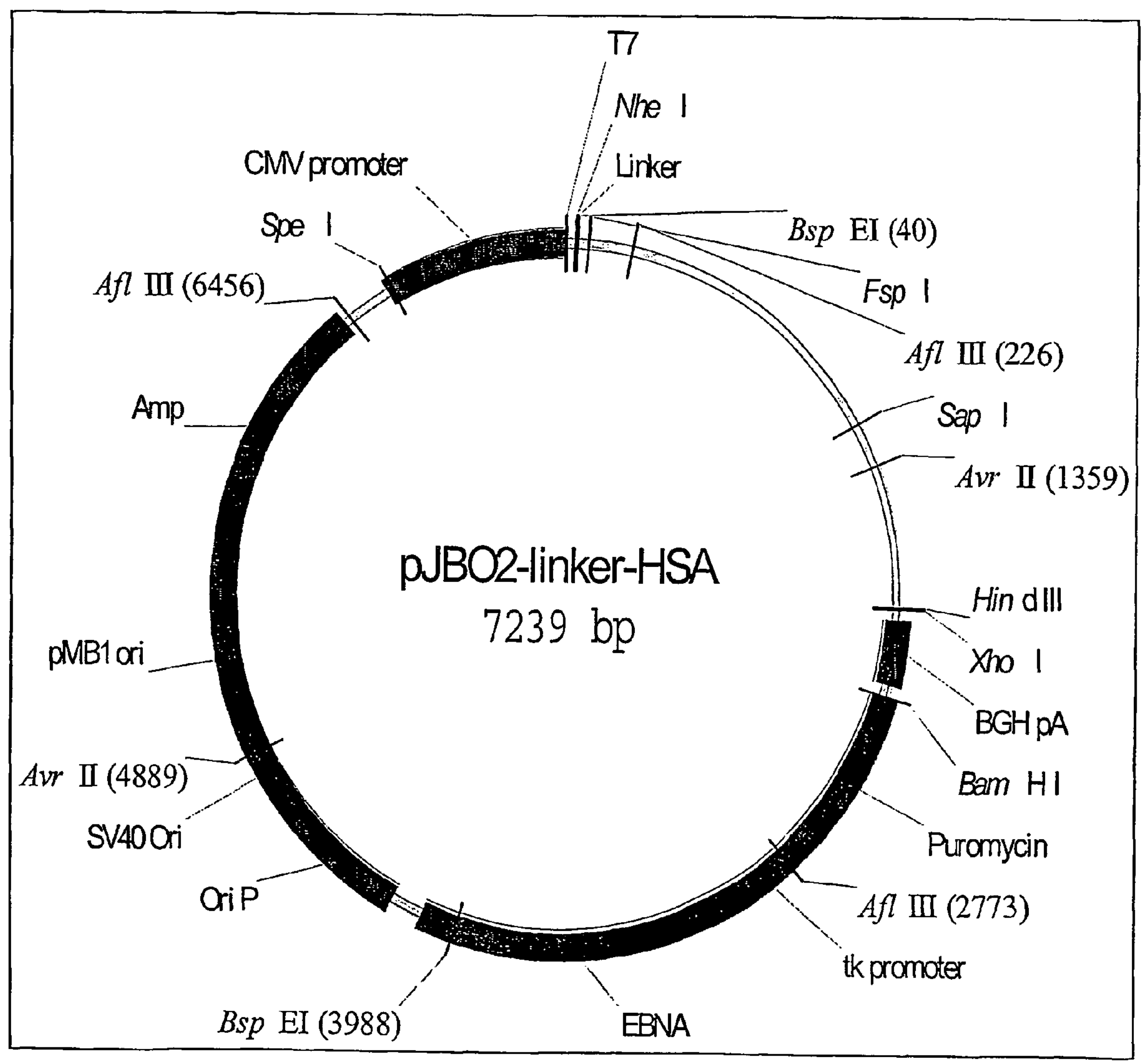

FIG. 7: Expression cloning vector containing DNA encoding a 15 amino acid linker fused in frame and 5' of the albumin sequence-illustrated in FIG. 2.

Figure 8:
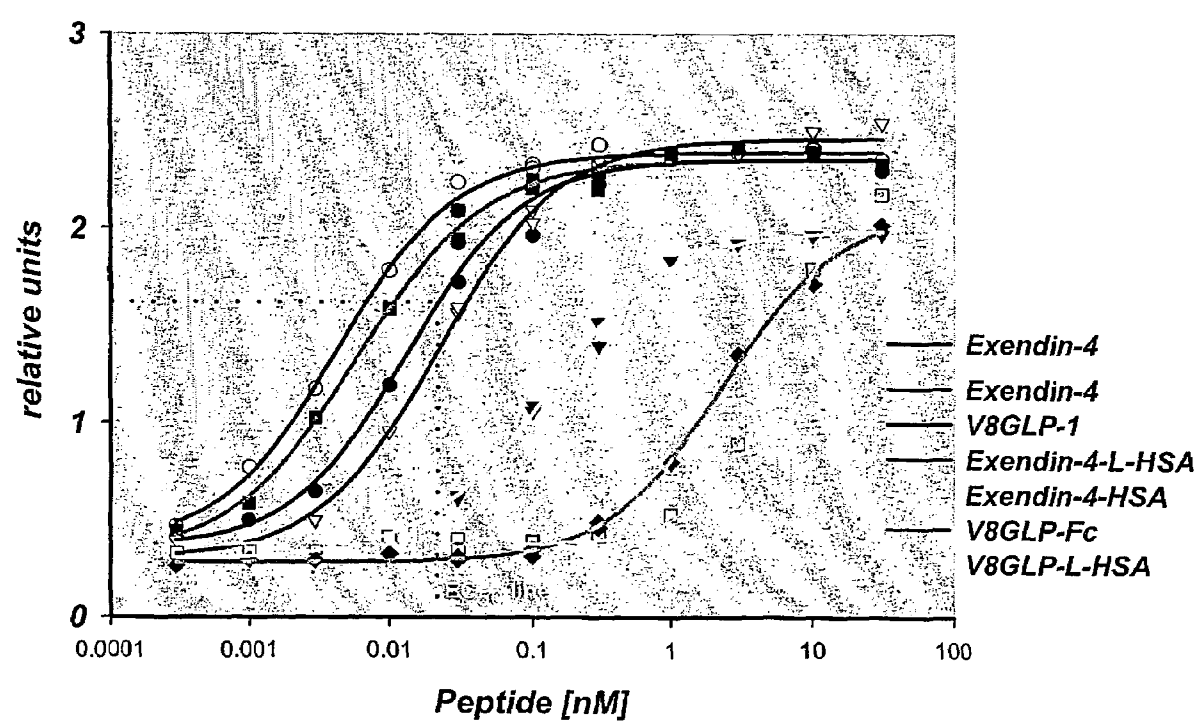

FIG. 8: In vitro dose response activity of GLP-1 fusion proteins.

Figure 9:
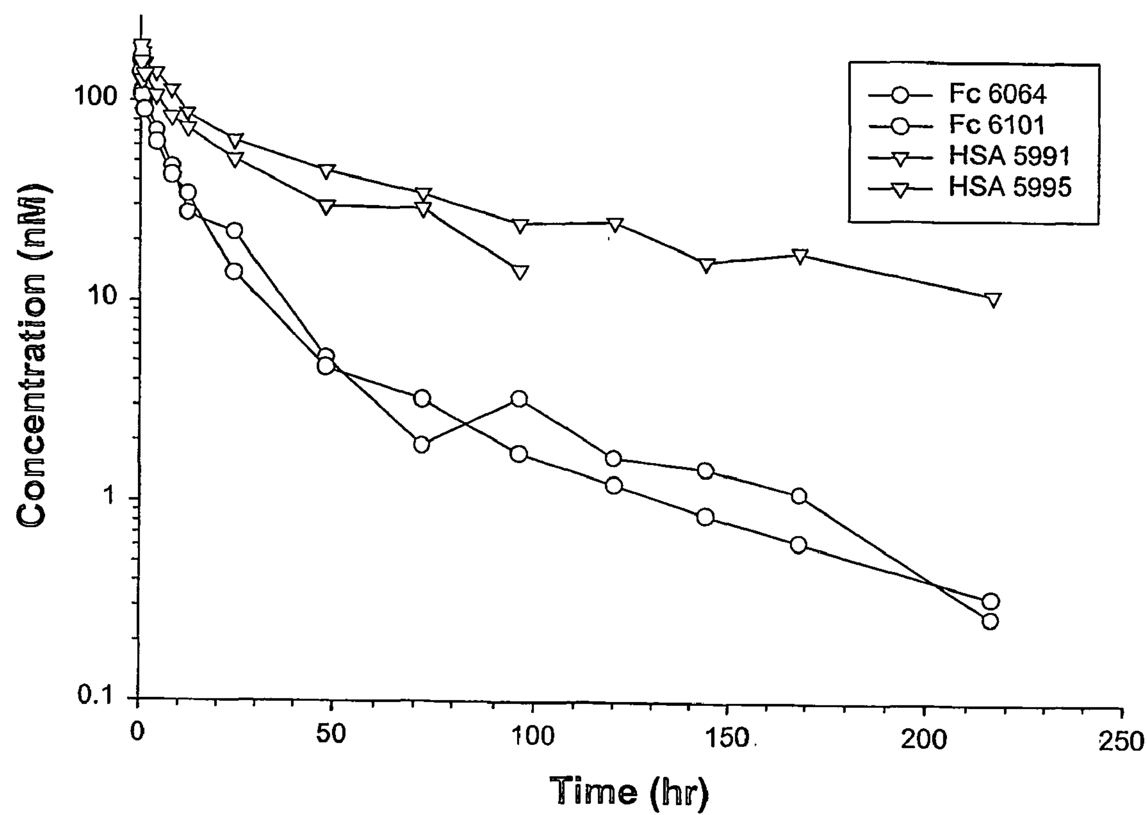

FIG. 9: Pharmacokinetics of GLP-1 Fc and HSA fusion proteins.

Figure 10:
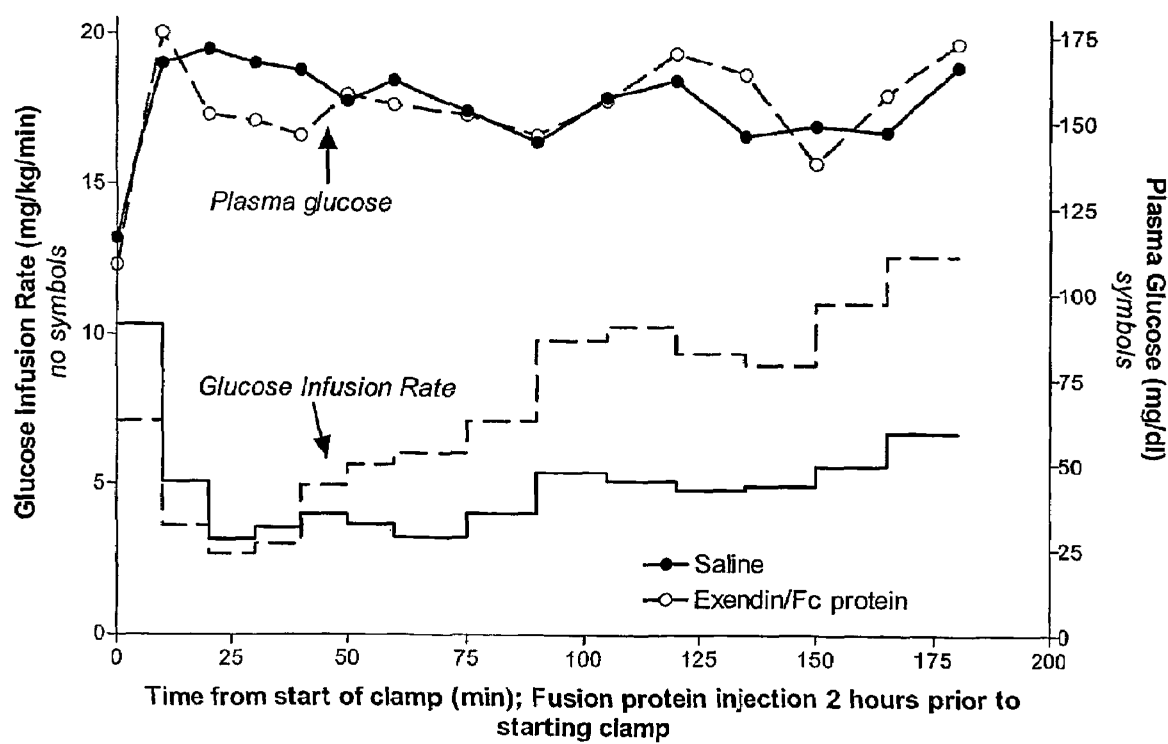
Figure 10:
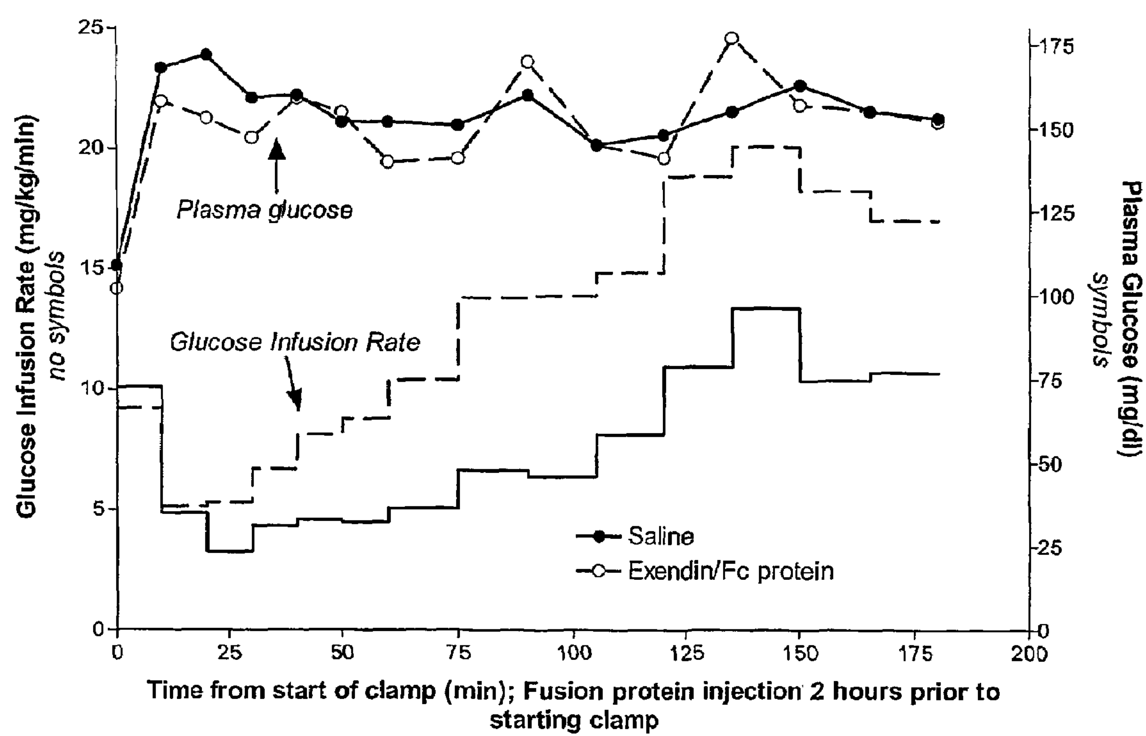

FIG. 10: Glucodynamic response to Exendin-Fc in two normal fasted dogs.

Figure 11:
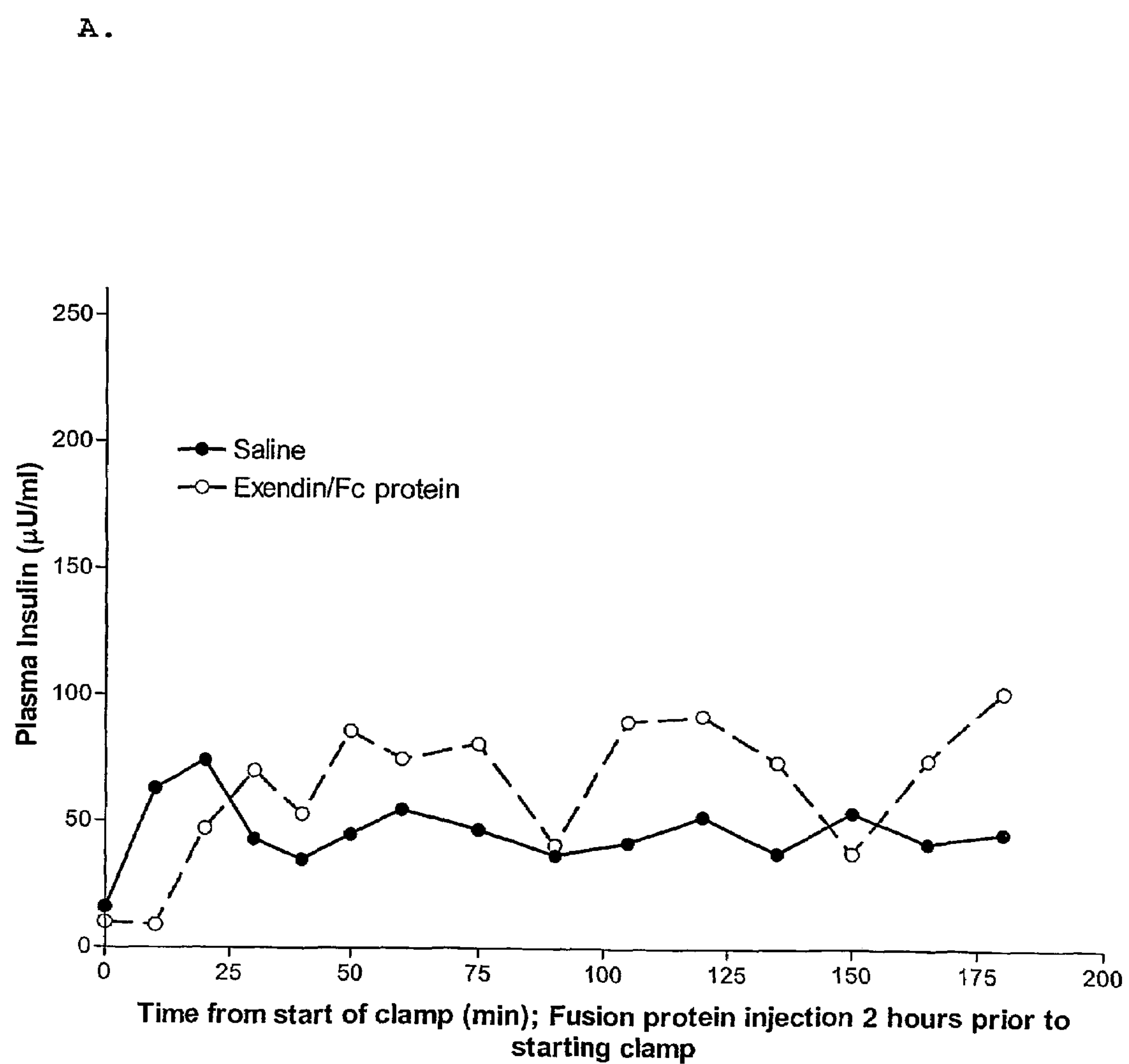
Figure 11:
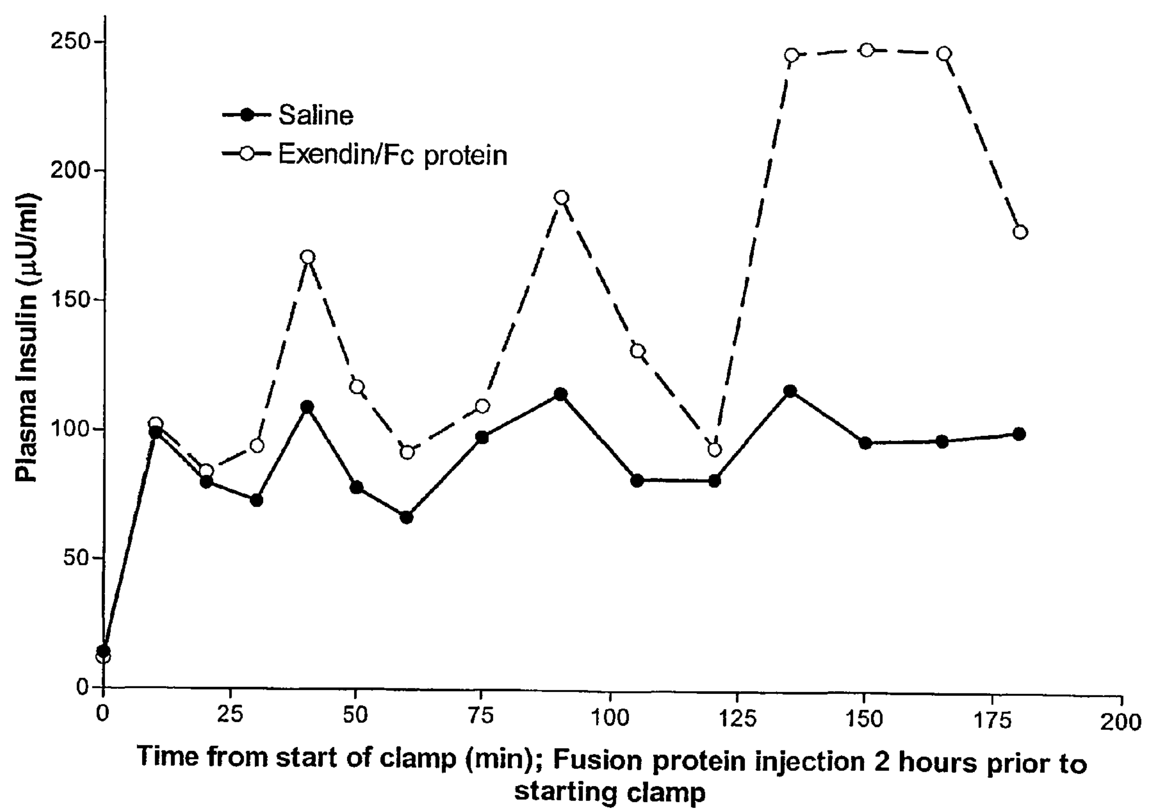

FIG. 11: Insulinotropic response to Exendin-Fc in two normal fasted dogs.

FIG. 12: DNA sequence encoding a human IgG1 Fc region.

FIG. 13: DNA sequence encoding a human albumin protein.

The heterologous fusion proteins of the present invention comprise a GLP-1 compound fused to human albumin, a human albumin analog, a human albumin fragment, the Fc portion of an immunoglobulin, an analog of the Fc portion of an immunoglobulin, or a fragment of the Fc portion of an immunoglobulin. The C-terminus of the GLP-1 compound may be fused directly, or fused via a peptide linker, to the N-terminus of an albumin or Fc protein. These heterologous fusion proteins are biologically active and have an increased half-life compared to native GLP-1.

It is preferred that the GLP-1 compounds that make up part of the heterologous fusion protein encompass polypeptides having from about twenty-five to about thirty-nine naturally occurring or non-naturally occurring amino acids that have sufficient homology to native GLP-1(7-37)OH such that they exhibit insulinotropic activity by binding to the GLP-1 receptor on β-cells in the pancreas. A GLP-1 compound typically comprises a polypeptide having the amino acid sequence of GLP-1(7-37)OH, an analog of GLP-1 (7-37)OH, a fragment of GLP-1(7-37)OH or a fragment of a GLP-1(7-37)OH analog. GLP-1(7-37)OH has the amino acid sequence of SEQ ID NO: 1:

```
                                        (SEQ ID NO: 1)
 7   8   9  10  11  12  13  14  15  16  17
His-Ala-Glu-Gly-Thr-Phe-Thr-Ser-Asp-Val-Ser-

18  19  20  21  22  23  24  25  26  27  28
Ser-Tyr-Leu-Glu-Gly-Gln-Ala-Ala-Lys-Glu-Phe-

29  30  31  32  33  34  35  36  37
Ile-Ala-Trp-Leu-Val-Lys-Gly-Arg-Gly
```

By custom in the art, the amino terminus of GLP-1(7-37) OH has been assigned number residue 7 and the carboxy-terminus, number 37. The other amino acids in the polypeptide are numbered consecutively, as shown in SEQ ID NO: 1. For example, position 12 is phenylalanine and position 22 is glycine.

GLP-1 compounds also encompass "GLP-1 fragments." A GLP-1 fragment is a polypeptide obtained after truncation of one or more amino acids from the N-terminus and/or C-terminus of GLP-1(7-37)OH or an analog or derivative thereof. The nomenclature used to describe GLP-1(7-37)OH is also applicable to GLP-1 fragments. For example, GLP-1(9-36) OH denotes a GLP-1 fragment obtained by truncating two amino acids from the N-terminus and one amino acid from the C-terminus. The amino acids in the fragment are denoted by the same number as the corresponding amino acid in GLP-1(7-37)OH. For example, the N-terminal glutamic acid in GLP-1(9-36)OH is at position 9; position 12 is occupied by phenylalanine; and position 22 is occupied by glycine, as in GLP-1(7-37)OH. For GLP-1(7-36)OH, the glycine at position 37 of GLP-1(7-37)OH is deleted.

GLP-1 compounds also include polypeptides in which one or more amino acids have been added to the N-terminus and/or C-terminus of GLP-1(7-37)OH, or fragments or analogs thereof. It is preferred that GLP-1 compounds of this type have up to about thirty-nine amino acids. The amino acids in the "extended" GLP-1 compound are denoted by the same number as the corresponding amino acid in GLP-1(7-37)OH. For example, the N-terminus amino acid of a GLP-1 compound obtained by adding two amino acids to the N-terminal of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these "extended" GLP-1 compounds, as in GLP-1(7-37)OH. Amino acids 1-6 of an extended GLP-1 compound are preferably the same as or a conservative substitution of the amino acid at the corresponding position of GLP-1(1-37) OH. Amino acids 38-45 of an extended GLP-1 compound are preferably the same as or a conservative substitution of the amino acid at the corresponding position of glucagon or Exendin-4.

GLP-1 compounds of the present invention encompass "GLP-1 analogs." A GLP-1 analog has sufficient homology to GLP-1(7-37)OH or a fragment of GLP-1(7-37)OH such that the analog has insulinotropic activity. Preferably, a GLP-1 analog has the amino acid sequence of GLP-1(7-37) OH or a fragment thereof, modified so that from one, two, three, four or five amino acids differ from the amino acid in the corresponding position of GLP-1(7-37)OH or a fragment of GLP-1(7-37)OH. In the nonmenclature used herein to designate GLP-1 compounds, the substituting amino acid and its position is indicated prior to the parent structure. For example, $Glu^{22}$-GLP-1(7-37)OH designates a GLP-1 compound in which the glycine normally found at position 22 of GLP-1(7-37)OH has been replaced with glutamic acid; $Val^{8}$-$Glu^{22}$-GLP-1(7-37)OH designates a GLP-1 compound in which alanine normally found at position 8 and glycine normally found at position 22 of GLP-1(7-37)OH have been replaced with valine and glutamic acid, respectively.

GLP-1 compounds of the present invention also include "GLP-1 derivatives." A GLP-1 derivative is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ϵ-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$-$C_4$ alkyl. Furthermore, one or more side groups, or terminal groups, may be protected by protective groups known to the ordinarily-skilled protein chemist. The α-carbon of an amino acid may be mono- or dimethylated.

Any GLP-1 compound can be part of the heterologous fusion proteins of the present invention as long as the GLP-1 compound itself is able to bind and induce signaling through the GLP-1 receptor. GLP-1 receptor binding and signal transduction can be assessed using in vitro assays such as those described in EP 619,322 and U.S. Pat. No. 5,120,712, respectively.

Numerous active GLP-1 fragments, analogs and derivatives are known in the art and any of these analogs and derivatives can also be part of the heterologous fusion proteins of the present invention. Some examples of novel GLP-1 analogs as well as GLP-1 analogs and derivatives known in the art are provided herein.

Some GLP-1 analogs and GLP-1 fragments known in the art include, for example, GLP-1(7-34) and GLP-1(7-35), GLP-1(7-36), $Gln^{9}$-GLP-1(7-37), D-$Gln^{9}$-GLP-1(7-37), $Thr^{16}$-$Lys^{18}$-GLP-1(7-37), and $Lys^{18}$-GLP-1(7-37). GLP-1 analogs such as GLP-1(7-34) and GLP-1(7-35) are disclosed in U.S. Pat. No. 5,118,666. Biologically processed forms of GLP-1 which have insulinotropic properties, such as GLP-1(7-36) are also known. Other known biologically active GLP-1 compounds are disclosed in U.S. Pat. No 5,977,071 to Hoffmann, et al., U.S. Pat. No. 5,545,618 to Buckley, et al., and Adelhorst, et al., *J. Biol. Chem.* 269:6275 (1994).

A preferred group of GLP-1 analogs is composed of GLP-1 analogs of formula I (SEQ ID NO: 2)

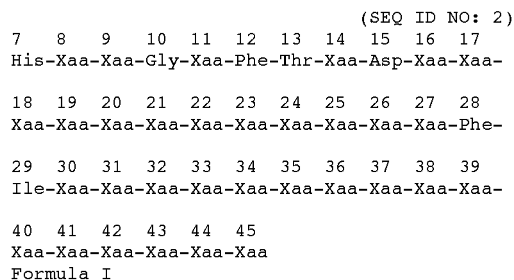

```
                                        (SEQ ID NO: 2)
7   8   9   10  11  12  13  14  15  16  17
His-Xaa-Xaa-Gly-Xaa-Phe-Thr-Xaa-Asp-Xaa-Xaa-

18  19  20  21  22  23  24  25  26  27  28
Xaa-Xaa-Xaa-Xaa-Xaa-Xaa-Xaa-Xaa-Xaa-Xaa-Phe-

29  30  31  32  33  34  35  36  37  38  39
Ile-Xaa-Xaa-Xaa-Xaa-Xaa-Xaa-Xaa-Xaa-Xaa-Xaa-

40  41  42  43  44  45
Xaa-Xaa-Xaa-Xaa-Xaa-Xaa
Formula I
```

wherein:

Xaa at position 8 is Ala, Gly, Ser, Thr, Leu, Ile, Val, Glu, Asp, or Lys;

Xaa at position 9 is Glu, Asp, or Lys;

Xaa at position 11 is Thr, Ala, Gly, Ser, Leu, Ile, Val, Glu, Asp, or Lys;

Xaa at position 14 is Ser, Ala, Gly, Thr, Leu, Ile, Val, Glu, Asp, or Lys;

Xaa at position 16 is Val, Ala, Gly, Ser, Thr, Leu, Ile, Tyr, Glu, Asp, Trp, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, Trp, Tyr, or Lys;

Xaa at position 19 is Tyr, Phe, Trp, Glu, Asp, Gln, or Lys;

Xaa at position 20 is Leu, Ala, Gly, Ser, Thr, Ile, Val, Glu, Asp, Met, Trp, Tyr, or Lys;

Xaa at position 21 is Glu, Asp, or Lys;

Xaa at position 22 is Gly, Ala, Ser, Thr, Leu, Ile, Val, Glu, Asp, or Lys;

Xaa at position 23 is Gln, Asn, Arg, Glu, Asp, or Lys;

Xaa at position 24 is Ala, Gly, Ser, Thr, Leu, Ile, Val, Arg, Glu, Asp, or Lys;

Xaa at position 25 is Ala, Gly, Ser, Thr, Leu, Ile, Val, Glu, Asp, or Lys;

Xaa at position 26 is Lys, Arg, Gln, Glu, Asp, or His;

Xaa at position 27 is Leu, Glu, Asp, or Lys;

Xaa at position 30 is Ala, Gly, Ser, Thr, Leu, Ile, Val, Glu, Asp, or Lys;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 37 is Pro, Gly, Ala, Ser, Thr, Leu, Ile, Val, Glu, Asp, or Lys, or is deleted;

Xaa at position 38 is Ser, Arg, Lys, Glu, Asp, or His, or is deleted;

Xaa at position 39 is Ser, Arg, Lys, Glu, Asp, or His, or is deleted;

Xaa at position 40 is Gly, Asp, Glu, or Lys, or is deleted;

Xaa at position 41 is Ala, Phe, Trp, Tyr, Glu, Asp, or Lys, or is deleted;

Xaa at position 42 is Ser, Pro, Lys, Glu, or Asp, or is deleted;

Xaa at position 43 is Ser, Pro, Glu, Asp, or Lys, or is deleted;

Xaa at position 44 is Gly, Pro, Glu, Asp, or Lys, or is deleted; and

Xaa at position 45 is Ala, Ser, Val, Glu, Asp, or Lys, or is deleted;

provided that when the amino acid at position 37, 38, 39, 40, 41, 42, 43, or 44 is deleted, then each amino acid downstream of that amino acid is also deleted.

It is preferred that the GLP-1 compound of formula I contain less than six amino acids that differ from the corresponding amino acid in GLP-1(7-37)OH or Exendin-4. It is more preferred that less than five amino acids differ from the corresponding amino acid in GLP-1(7-37)OH or Exendin-4. It is even more preferred that less than four amino acids differ from the corresponding amino acid in GLP-1(7-37)OH or Exendin-4.

GLP-1 compounds of the present invention include derivatives of formula I such as a C-1-6-ester, or amide, or C-1-6-alkylamide, or C-1-6-dialkylamide thereof. WO99/43706 describes derivatives of GLP-1 compounds of formula I and is incorporated by reference herein in its entirety. The compounds of formula I derivatized as described in WO99/43706 and underivatized are encompassed by the present invention.

Another preferred group of GLP-1 compounds is composed of GLP-1 analogs of formula II (SEQ ID NO: 3):

```
                                    (SEQ ID NO: 3)
7   8   9   10  11  12  13  14  15  16  17
Xaa-Xaa-Xaa-Gly-Xaa-Xaa-Thr-Ser-Asp-Xaa-Ser-

 18  19  20  21  22  23  24  25  26  27  28
Xaa-Xaa-Leu-Glu-Gly-Xaa-Xaa-Ala-Xaa-Xaa-Phe-

 29  30  31  32  33  34  35  36 37
Ile-Xaa-Xaa-Leu-Xaa-Xaa-Xaa-Xaa-R
Formula II
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, or Thr;

Xaa at position 9 is: Thr, Ser, Arg, Lys, Trp, Phe, Tyr, Glu, or His;

Xaa at position 11 is: Asp, Glu, Arg, Thr, Ala, Lys, or His;

Xaa at position 12 is: His, Trp, Phe, or Tyr;

Xaa at position 16 is: Leu, Ser, Thr, Trp, His, Phe, Asp, Val, Tyr, Glu, or Ala;

Xaa at position 18 is: His, Pro, Asp, Glu, Arg, Ser, Ala, or Lys;

Xaa at position 22 is: Gly, Asp, Glu, Gln, Asn, Lys, Arg, or Cys;

Xaa at position 23 is: His, Asp, Lys, Glu, Gln, or Arg;

Xaa at position 24 is: Glu, Arg, Ala, or Lys;

Xaa at position 26 is: Trp, Tyr, Phe, Asp, Lys, Glu, or His;

Xaa at position 27 is: Ala, Glu, His, Phe, Tyr, Trp, Arg, or Lys;

Xaa at position 30 is: Ala, Glu, Asp, Ser, or His;

Xaa at position 31 is: Asp, Glu, Ser, Thr, Arg, Trp, or Lys;

Xaa at position 33 is: Asp, Arg, Val, Lys, Ala, Gly, or Glu;

Xaa at position 34 is: Glu, Lys, or Asp;

Xaa at position 35 is: Thr, Ser, Lys, Arg, Trp, Tyr, Phe, Asp, Gly, Pro, His, or Glu;

Xaa at position 36 is: Thr, Ser, Asp, Trp, Tyr, Phe, Arg, Glu, or His;

R at position 37 is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of formula III (SEQ ID NO: 4):

```
                                    (SEQ ID NO: 4)
7   8   9   10  11  12  13  14  15  16  17
Xaa-Xaa-Glu-Gly-Xaa-Xaa-Thr-Ser-Asp-Xaa-Ser-

18  19  20  21  22  23  24  25  26  27  28
Ser-Tyr-Leu-Glu-Xaa-Xaa-Xaa-Xaa-Lys-Xaa-Phe-

29  30  31  32  33  34  35  36  37
Ile-Xaa-Trp-Leu-Xaa-Xaa-Xaa-Xaa-R
formula III
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, or Thr;

Xaa at position 11 is: Asp, Glu, Arg, Thr, Ala, Lys, or His;

Xaa at position 12 is: His, Trp, Phe, or Tyr;

Xaa at position 16 is: Leu, Ser, Thr, Trp, His, Phe, Asp, Val, Glu, or Ala;

Xaa at position 22: Gly, Asp, Glu, Gln, Asn, Lys, Arg, or Cys;

Xaa at position 23 is: His, Asp, Lys, Glu, or Gln;

Xaa at position 24 is: Glu, His, Ala, or Lys;

Xaa at position 25 is: Asp, Lys, Glu, or His;

Xaa at position 27 is: Ala, Glu, His, Phe, Tyr, Trp, Arg, or Lys;

Xaa at position 30 is: Ala, Glu, Asp, Ser, or His;

Xaa at position 33 is: Asp, Arg, Val, Lys, Ala, Gly, or Glu;

Xaa at position 34 is: Glu, Lys, or Asp;

Xaa at position 35 is: Thr, Ser, Lys, Arg, Trp, Tyr, Phe, Asp, Gly, Pro, His, or Glu;

Xaa at position 36 is: Arg, Glu, or His;

R at position 37 is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of formula IV (SEQ ID NO: 5):

```
                                    (SEQ ID NO: 5)
7   8   9   10  11  12  13  14  15  16  17
Xaa-Xaa-Glu-Gly-Thr-Xaa-Thr-Ser-Asp-Xaa-Ser-

18  19  20  21  22  23  24  25  26  27  28
Ser-Tyr-Leu-Glu-Xaa-Xaa-Ala-Ala-Xaa-Glu-Phe-

29  30  31  32  33  34  35  36  37
Ile-Xaa-Trp-Leu-Val-Lys-Xaa-Arg-R
formula IV
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, Met, or Thr;

Xaa at position 12 is: His, Trp, Phe, or Tyr.;

Xaa at position 16 is: Leu, Ser, Thr, Trp, His, Phe, Asp, Val, Glu, or Ala;

Xaa at position 22 is: Gly, Asp, Glu, Gln, Asn, Lys, Arg, or Cys;

Xaa at position 23 is: His, Asp, Lys, Glu, or Gln;

Xaa at position 26 is: Asp, Lys, Glu, or His;

Xaa at position 30 is: Ala, Glu, Asp, Ser, or His;

Xaa at position 35 is: Thr, Ser, Lys, Arg, Trp, Tyr, Phe, Asp, Gly, Pro, His, or Glu;

R at position 37 is: Lys, Arg, Thr, Ser, Glu, Asp, Trp, Tyr, Phe, His, Gly, Gly-Pro, or is deleted.

Another preferred group of GLP-1 compounds is composed of GLP-1 analogs of formula V (SEQ ID NO: 6):

```
                                      (SEQ ID NO: 6)
7   8   9   10  11  12  13  14  15  16  17
Xaa-Xaa-Glu-Gly-Thr-Phe-Thr-Ser-Asp-Val-Ser-

18  19  20  21  22  23  24  25  26  27  28
Ser-Tyr-Leu-Glu-Xaa-Xaa-Xaa-Ala-Lys-Glu-Phe

29  30  31  32  33  34  35  36  37
Ile-Xaa-Trp-Leu-Val-Lys-Gly-Arg-R
formula V
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, or Thr;

Xaa at position 22 is: Gly, Asp, Glu, Gln, Asn, Lys, Arg, or Cys;

Xaa at position 23 is: His, Asp, Lys, Glu, or Gln;

Xaa at position 24 is: Ala, Glu, His, Phe, Tyr, Trp, Arg, or Lys;

Xaa at position 30 is: Ala, Glu, Asp, Ser, or His;

R at position 37 is: Lys, Arg, Thr, Ser, Glu, Asp, Trp, Tyr, Phe, His, Gly, Gly-Pro, or is deleted.

Preferred GLP-1 compounds of formula I, II, III, IV, and V comprise GLP-1 analogs or fragments of GLP-1 analogs wherein the analogs or fragments contain an amino acid other than alanine at position 8 (position 8 analogs). It is preferable that these position 8 analogs contain one or more additional changes at positions 9, 11, 12, 16, 18, 22, 23, 24, 26, 27, 30, 31, 33, 34, 35, 36, and 37 compared to the corresponding amino acid of native GLP-1(7-37)OH. It is also preferable that these analogs have 6 or fewer changes compared to the corresponding amino acids in native GLP-1(7-37)OH or GLP-1(7-36)OH. More preferred analogs have 5 or fewer changes compared to the corresponding amino acids in native GLP-1(7-37)OH or GLP-1(7-36)OH or have 4 or fewer changes compared to the corresponding amino acids in native GLP-1(7-37)OH or GLP-1(7-36)OH. It is even more preferable that these analogs have 3 or fewer changes compared to the corresponding amino acids in native GLP-1(7-37)OH or GLP-1(7-36)OH. It is most preferable that these analogs have 2 or fewer changes compared to the corresponding amino acids in native GLP-1(7-37)OH.

It has been found that the compounds of formula II, III, IV, and V have a reduced propensity to aggregate and generate insoluble forms. This is also important in the context of a fusion protein wherein the relatively small GLP-1 peptide must maintain an active conformation despite being fused to a much larger protein. Preferred GLP-1 compounds of formula II, III, IV, and V encompassed by the fusion proteins of the present invention comprise GLP-1 analogs or fragments of GLP-1 analogs in which glycine at position 22 and preferably alanine at position 8 have been replaced with another amino acid.

When position 22 is aspartic acid, glutamic acid, arginine or lysine, position 8 is preferably glycine, valine, leucine, isolecine, serine, threonine or methionine and more preferably valine or glycine. When position 22 is a sulfonic acid such as cysteic acid, position 8 is preferably glycine, valine, leucine, isolecine, serine, threonine or methionine and more preferably valine or glycine.

Other preferred GLP-1 compounds include GLP-1 analogs of formula IV (SEQ ID NO: 5) wherein the analogs have the sequence of GLP-1(7-37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamatic acid.

Other preferred GLP-1 compounds include GLP-1 analogs of formula IV (SEQ ID NO: 5) wherein the analogs have the sequence of GLP-1(7-37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

Other preferred GLP-1 compounds include GLP-1 analogs of formula IV (SEQ ID NO: 5) wherein the analogs have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 23 is lysine, arginine, glutamic acid, aspartic acid, and histidine and more preferably lysine or glutamic acid.

Other preferred GLP-1 compounds include GLP-1 analogs of formula V (SEQ ID NO: 6) wherein the analogs have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamine acid or lysine and position 27 is alanine, lysine, arginine, tryptophan, tyrosine, phenylalanine, or histidine and more preferably alanine.

Other preferred GLP-1 compounds include GLP-1 analogs of formula II wherein the analogs have the sequence of GLP-1(7-37)OH except that the amino acid at position 8 and one, two, or three amino acids selected from the group consisting of position 9, position 11, position 12, position 16, position 18, position 22, position 23, position 24, position 26, position 27, position 30, position 31, position 33, position 34, position 35, position 36, and position 37, differ from the amino acid at the corresponding position of native GLP-1(7-37)OH.

Other preferred GLP-1 compounds of formula II include: $Val^{8}$-GLP-1(7-37)OH, $Gly^{8}$-GLP-1(7-37)OH, $Glu^{22}$-GLP-1(7-37)OH, $Asp^{22}$-GLP-1(7-37)OH, $Arg^{22}$-GLP-1(7-37)OH, $Lys^{22}$-GLP-1(7-37)OH, $Cys^{22}$-GLP-1(7-37)OH, $Val^{8}$-$Glu^{22}$-GLP-1(7-37)OH, $Val^{8}$-$Asp^{22}$-GLP-1(7-37)OH, $Val^{8}$-$Arg^{22}$-GLP-1(7-37)OH, $Val^{8}$-$Lys^{22}$-GLP-1(7-37)OH, $Val^{8}$-$Cys^{22}$-GLP-1(7-37)OH, $Gly^{8}$-$Glu^{22}$-GLP-1(7-37)OH, $Gly^{8}$-$Asp^{22}$-GLP-1(7-37)OH, $Gly^{8}$-$Arg^{22}$-GLP-1(7-37)OH, $Gly^{8}$-$Lys^{22}$-GLP-1(7-37)OH, $Gly^{8}$-$Cys^{22}$-GLP-1(7-37)OH, $Glu^{22}$-GLP-1(7-36)OH, $Asp^{22}$-GLP-1(7-36)OH, $Arg^{22}$-GLP-1(7-36)OH, $Lys^{22}$-GLP-1(7-36)OH, $Cys^{22}$-GLP-1(7-36)OH, $Val^{8}$-$Glu^{22}$-GLP-1(7-36)OH, $Val^{8}$-$Asp^{22}$-GLP-1(7-36)OH, $Val^{8}$-$Arg^{22}$-GLP-1(7-36)OH, $Val^{8}$-$Lys^{22}$-GLP-1(7-

36)OH, Val$^{8}$-Cys$^{22}$-GLP-1(7-36)OH, Gly$^{8}$-Glu$^{22}$-GLP-1(7-36)OH, Gly$^{8}$-Asp$^{22}$-GLP-1(7-36)OH, Gly$^{8}$-Arg$^{22}$-GLP-1(7-36)OH, Gly$^{8}$-Lys$^{22}$-GLP-1(7-36)OH, Gly$^{8}$-Cys$^{22}$-GLP-1(7-36)OH, Lys$^{23}$-GLP-1(7-37)OH, Val$^{8}$-Lys$^{23}$-GLP-1(7-37)OH, Gly$^{8}$-Lys$^{23}$-GLP-1(7-37)OH, His$^{24}$-GLP-1(7-37)OH, Val$^{8}$-His$^{24}$-GLP-1(7-37)OH, Gly$^{8}$-His$^{24}$-GLP-1(7-37)OH, Lys$^{24}$-GLP-1(7-37)OH, Val$^{8}$-Lys$^{24}$-GLP-1(7-37)OH, Gly$^{8}$-Lys$^{23}$-GLP-1(7-37)OH, Glu$^{30}$-GLP-1(7-37)OH, Val$^{8}$-Glu$^{30}$-GLP-1(7-37)OH, Gly$^{8}$-Glu$^{30}$-GLP-1(7-37)OH, Asp$^{30}$-GLP-1(7-37)OH, Val$^{8}$-Asp$^{30}$-GLP-1(7-37)OH, Gly$^{8}$-Asp$^{30}$-GLP-1(7-37)OH, Gln$^{30}$-GLP-1(7-37)OH, Val$^{8}$-Gln$^{30}$-GLP-1(7-37)OH, Gly$^{8}$-Gln$^{30}$-GLP-1(7-37)OH, Tyr$^{30}$-GLP-1(7-37)OH, Val$^{8}$-Tyr$^{30}$-GLP-1(7-37)OH, Gly$^{8}$-Tyr$^{30}$-GLP-1(7-37)OH, Ser$^{30}$-GLP-1(7-37)OH, Val$^{8}$-Ser$^{30}$-GLP-1(7-37)OH, Gly$^{8}$-Ser$^{30}$-GLP-1(7-37)OH, His$^{30}$-GLP-1(7-37)OH, Val$^{8}$-His$^{30}$-GLP-1(7-37)OH, Gly$^{8}$-His$^{30}$-GLP-1(7-37)OH, Glu$^{34}$-GLP-1(7-37)OH, Val$^{8}$-Glu$^{34}$-GLP-1(7-37)OH, Gly$^{8}$-Glu$^{34}$-GLP-1(7-37)OH, Ala$^{34}$-GLP-1(7-37)OH, Val$^{8}$-Ala$^{34}$-GLP-1(7-37)OH, Gly$^{8}$-Ala$^{34}$-GLP-1(7-37)OH, Gly$^{34}$-GLP-1(7-37)OH, Val$^{8}$-Gly$^{34}$-GLP-1(7-37)OH, Gly$^{8}$-Gly$^{34}$-GLP-1(7-37)OH, Ala$^{35}$-GLP-1(7-37)OH, Val$^{8}$-Ala$^{35}$-GLP-1(7-37)OH, Gly$^{8}$-Ala$^{35}$-GLP-1(7-37)OH, Lys$^{35}$-GLP-1(7-37)OH, Val$^{8}$-Lys$^{35}$-GLP-1(7-37)OH, Gly$^{8}$-Lys$^{35}$-GLP-1(7-37)OH, His$^{35}$-GLP-1(7-37)OH, Val$^{8}$-His$^{35}$-GLP-1(7-37)OH, Gly$^{8}$-His$^{35}$-GLP-1(7-37)OH, Pro$^{35}$-GLP-1(7-37)OH, Val$^{8}$-Pro$^{35}$-GLP-1(7-37)OH, Gly$^{8}$-Pro$^{35}$-GLP-1(7-37)OH, Glu$^{35}$-GLP-1(7-37)OH Val$^{8}$-Glu$^{35}$-GLP-1(7-37)OH, Gly$^{8}$-Glu$^{35}$-GLP-1(7-37)OH, Val$^{8}$-Ala$^{27}$-GLP-1(7-37)OH, Val$^{8}$-His$^{37}$-GLP-1(7-37)OH, Val$^{8}$-Glu$^{22}$-Lys$^{23}$-GLP-1(7-37)OH, Val$^{8}$-Glu$^{22}$-Glu$^{23}$-GLP-1(7-37)OH, Val$^{8}$-Glu$^{22}$-Ala$^{27}$-GLP-1(7-37)OH, Val$^{8}$-Gly$^{34}$-Lys$^{35}$-GLP-1(7-37)OH, Val$^{8}$-His$^{37}$-GLP-1(7-37)OH, Gly$^{8}$-His$^{37}$-GLP-1(7-37)OH, Val$^{8}$-Glu$^{22}$-Ala$^{27}$-GLP-1(7-37)OH, Gly$^{8}$-Glu$^{22}$-Ala$^{27}$-GLP-1(7-37)OH, Val$^{8}$-Lys$^{22}$-Glu$^{23}$-GLP-1(7-37)OH, and Gly$^{8}$-Lys$^{22}$-Glu$^{23}$-GLP-1(7-37)OH.

Another preferred group of GLP-1 analogs and derivatives for use in the present invention is composed of molecules of formula VI (SEQ ID NO: 7)

(SEQ ID NO:7)

R$_1$-X-Glu-Gly$^{10}$-Thr-Phe-Thr-Ser-Asp$^{15}$-Val-Ser-

Ser-Tyr-Leu$^{20}$-Y -Gly-Gln-Ala-Ala$^{25}$-Lys-Z-

Phe-Ile-Ala$^{30}$-Trp-Leu-Val-Lys-Gly$^{35}$-Arg-R$_2$ formula VI wherein: $R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is Gly-OH.

Another preferred group of GLP-1 compounds for use in the present invention is disclosed in WO 91/11457, and consists essentially of GLP-1(7-34), GLP-1(7-35), GLP-1(7-36), or GLP-1(7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, [see, e.g., Mentlein, R., et al., *Eur. J. Biochem*., 214:829-835 (1993)], GLP-1 analogs and derivatives that are protected from the activity of DPP IV in the context of a fusion protein are preferred, and fusion proteins wherein the GLP-1 compound is Gly$^{8}$-GLP-1(7-37)OH, Val$^{8}$-GLP-1(7-37)OH, α-methyl-Ala$^{8}$-GLP-1(7-37)OH, or Gly$^{8}$-Gln$^{21}$-GLP-1(7-37)OH are more preferred.

Another preferred group of GLP-1 compounds for use in the present invention consists of the compounds of formula VII (SEQ ID NO: 8) claimed in U.S. Pat. No. 5,512,549, which is expressly incorporated herein by reference.

(SEQ ID NO: 8)

R$^1$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Xaa-Glu-Phe-Ile-Ala$^{30}$-

Trp-Leu-Val-Lys-Gly$^{35}$-Arg-R$^3$

|

R$^2$ formula VII wherein $R^1$ is selected from the group consisting of 4-imidazopropionyl, 4-imidazoacetyl, or 4-imidazo-α, α dimethyl-acetyl; $R^2$ is selected from the group consisting of $C_6$-$C_{10}$ unbranched acyl, or is absent; $R^3$ is selected from the group consisting of Gly-OH or $NH_2$; and, Xaa is Lys or Arg.

More preferred compounds of formula IV for use in the present invention are those in which Xaa is Arg and $R^2$ is $C_6$-$C_{10}$ unbranched acyl. Even more preferred compounds of formula IV for use in the present invention are those in which Xaa is Arg, $R^2$ is $C_6$-$C_{10}$ unbranched acyl, and $R^3$ is Gly-OH. Other highly-preferred compounds of formula IV for use in the present invention are those in which Xaa is Arg, $R^2$ is $C_6$-$C_{10}$ unbranched acyl, $R^3$ is Gly-OH, and $R^1$ is 4-imidazopropionyl. An especially preferred compound of formula IV for use in the present invention is that in which Xaa is Arg, $R^2$ is $C_8$ unbranched acyl, $R^3$ is Gly-OH, and $R^1$ is 4-imidazopropionyl.

Preferably, the GLP-1 compounds comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 12, 16, 18, 19, 20, 22, 25, 27, 30, 33, and 37 compared to the corresponding amino acid of native GLP-1(7-37)OH. It is more preferable that these position 8 analogs contain one or more additional changes at positions 16, 18, 22, 25 and 33 compared to the corresponding amino acid of native GLP-1(7-37)OH.

In a preferred embodiment, the GLP-1 analog is GLP-1 (7-37)OH wherein the amino acid at position 12 is selected from the group consisting of tryptophan or tyrosine. It is more preferred that in addition to the substitution at position 12, the amino acid at position 8 is substituted with glycine, valine, leucine, isoleucine, serine, threonine, or methionine and more preferably valine or glycine. It is even more preferred that in addition to the substitutions at position 12 and 8, the amino acid at position 22 is substituted with glutamic acid.

In another preferred embodiment, the GLP-1 analog is GLP-1(7-37)OH wherein the amino acid at position 16 is selected from the group consisting of tryptophan, isoleucine, leucine, phenylalanine, or tyrosine. It is more preferred that in addition to the substitution at position 16, the amino acid at position 8 is substituted with glycine, valine, leucine, isoleucine, serine, threonine, or methionine and more preferably valine or glycine. It is even more preferred that in addition to the substitutions at position 16 and 8, the amino acid at position 22 is substituted with glutamic acid. It is also preferred that in addition to the substitutions at positions 16 and 8, the amino acid at position 30 is substituted with glutamic acid. It is also preferred that in addition to the substitutions at positions 16 and 8, the amino acid at position 37 is substituted with histidine.

In another preferred embodiment, the GLP-1 analog is GLP-1(7-37)OH wherein the amino acid at position 18 is selected from the group consisting of tryptophan, tyrosine, phenylalanine, lysine, leucine, or isoleucine, preferably tryptophan, tyrosine, and isoleucine. It is more preferred that in addition to the substitution at position 18, the amino acid at position 8 is substituted with glycine, valine, leucine, isoleucine, serine, threonine, or methionine and more preferably valine or glycine. It is even more preferred that in addition to the substitutions at position 18 and 8, the amino acid at position 22 is substituted with glutamic acid. It is also preferred that in addition to the substitutions at positions 18 and 8, the amino acid at position 30 is substituted with glutamic acid. It is also preferred that in addition to the substitutions at positions 18 and 8, the amino acid at position 37 is substituted with histidine In another preferred embodiment, the GLP-1 analog is GLP-1(7-37)OH wherein the amino acid at position 19 is selected from the group consisting of tryptophan or phenylalanine, preferably tryptophan. It is more preferred that in addition to the substitution at position 19, the amino acid at position 8 is substituted with glycine, valine, leucine, isoleucine, serine, threonine, or methionine and more preferably valine or glycine. It is even more preferred that in addition to the substitutions at position 19 and 8, the amino acid at position 22 is substituted with glutamic acid. It is also preferred that in addition to the substitutions at positions 19 and 8, the amino acid at position 30 is substituted with glutamic acid. It is also preferred that in addition to the substitutions at positions 19 and 8, the amino acid at position 37 is substituted with histidine In another preferred embodiment, the GLP-1 analog is GLP-1(7-37)OH wherein the amino acid at position 20 is phenylalanine, tyrosine, or tryptophan. It is more preferred that in addition to the substitution at position 20, the amino acid at position 8 is substituted with glycine, valine, leucine, isoleucine, serine, threonine, or methionine and more preferably valine or glycine. It is even more preferred that in addition to the substitutions at position 20 and 8, the amino acid at position 22 is substituted with glutamic acid. It is also preferred that in addition to the substitutions at positions 20 and 8, the amino acid at position 30 is substituted with glutamic acid. It is also preferred that in addition to the substitutions at positions 20 and 8, the amino acid at position 37 is substituted with histidine In another preferred embodiment, the GLP-1 analog is GLP-1(7-37)OH wherein the amino acid at position 25 is selected from the group consisting of valine, isoleucine, and leucine, preferably valine. It is more preferred that in addition to the substitution at position 25, the amino acid at position 8 is substituted with glycine, valine, leucine, isoleucine, serine, threonine, or methionine and more preferably valine or glycine. It is even more preferred that in addition to the substitutions at position 25 and 8, the amino acid at position 22 is substituted with glutamic acid. It is also preferred that in addition to the substitutions at positions 25 and 8, the amino acid at position 30 is substituted with glutamic acid. It is also preferred that in addition to the substitutions at positions 25 and 8, the amino acid at position 37 is substituted with histidine.

In another preferred embodiment, the GLP-1 analog is GLP-1(7-37)OH wherein the amino acid at position 27 is selected from the group consisting of isoleucine or alanine. It is more preferred that in addition to the substitution at position 27, the amino acid at position 8 is substituted with glycine, valine, leucine, isoleucine, serine, threonine, or methionine and more preferably valine or glycine. It is even more preferred that in addition to the substitutions at position 27 and 8, the amino acid at position 22 is substituted with glutamic acid. It is also preferred that in addition to the substitutions at positions 27 and 8, the amino acid at position 30 is substituted with glutamic acid. It is also preferred that in addition to the substitutions at positions 27 and 8, the amino acid at position 37 is substituted with histidine In another preferred embodiment, the GLP-1 analog is GLP-1(7-37)OH wherein the amino acid at position 33 is isoleucine. It is more preferred that in addition to the substitution at position 33, the amino acid at position 8 is substituted with glycine, valine, leucine, isoleucine, serine, threonine, or methionine and more preferably valine or glycine. It is even more preferred that in addition to the substitutions at position 33 and 8, the amino acid at position 22 is substituted with glutamic acid. It is also preferred that in addition to the substitutions at positions 33 and 8, the amino acid at position 30 is substituted with glutamic acid. It is also preferred that in addition to the substitutions at positions 33 and 8, the amino acid at position 37 is substituted with histidine The GLP-1 compounds have modifications at one or more of the following positions: 8, 12, 16, 18, 19, 20, 22, 25, 27, 30, 33, and 37. These GLP-1 compounds show increased potency compared with GLP-1(7-37)OH and comprise the amino acid sequence of formula IX (SEQ ID NO: 12)

```
                                    (SEQ ID NO: 12)
Xaa7-Xaa8-Glu-Gly-Thr-Xaa12-Thr-Ser-Asp-Xaa16-
Ser-

Xaa18-Xaa19-Xaa20-Glu-Xaa22-Gln-Ala-Xaa25-Lys-

Xaa27-Phe-Ile-Xaa30-Trp-Leu-Xaa33-Lys-Gly-Arg-
Xaa37
Formula IX
```

wherein:

$Xaa_7$ is: L-histidine, D-histidine, desamino-histidine, 2-amino-histidine, β-hydroxy-histidine, homohistidine, α-fluoromethyl-histidine, or α-methyl-histidine;

$Xaa_8$ is: Ala, Gly, Val, Leu, Ile, Ser, or Thr;

$Xaa_{12}$ is: Phe, Trp, or Tyr;

$Xaa_{16}$ is: Val, Trp, Ile, Leu, Phe, or Tyr;

$Xaa_{18}$ is: Ser, Trp, Tyr, Phe, Lys, Ile, Leu, Val;

$Xaa_{19}$ is: Tyr, Trp, or Phe;

$Xaa_{20}$ is: Leu, Phe, Tyr, or Trp;

$Xaa_{22}$ is: Gly, Glu, Asp, or Lys;

$Xaa_{25}$ is: Ala, Val, Ile, or Leu;

$Xaa_{27}$ is: Glu, Ile, or Ala;

$Xaa_{30}$ is: Ala or Glu $Xaa_{33}$ is: Val, or Ile; and $Xaa_{37}$ is: Gly, His, $NH_2$, or is absent.

Some preferred GLP-1 compounds of formula IX include GLP-1(7-37)OH, GLP-(7-36)-$NH_2$, $Gly^8$-GLP-1(7-37)OH, $Gly^8$-GLP-1(7-36)$NH_2$, $Val^8$-GLP-1(7-37)OH, $Val^8$-GLP-1(7-36)$NH_2$, $Leu^8$-GLP-1(7-37)OH, $Leu^8$-GLP-1(7-36)$NH_2$, $Ile^8$-GLP-1(7-37)OH, $Ile^8$-GLP-1(7-36)$NH_2$, Ser8-GLP-1(7-37)OH, Ser8-GLP-1(7-36)$NH_2$, $Thr^8$-GLP-1(7-37)OH, $Thr^8$-GLP-1(7-36)$NH_2$, $Val^8$-Tyr 2-GLP-1(7-37)OH, $Val^8$-$Tyr^{12}$-GLP-1(7-36)$NH_2$, $Val^8$-$Tyr^{16}$-GLP-1(7-37)OH, $Val^8$-$Tyr^{16}$-GLP-1(7-36)$NH_2$, Val-$Glu^{22}$-GLP-1(7-37)OH, $Val^8$-$Glu^{22}$-GLP-1(7-36)$NH_2$, $Gly^8$-$Glu^{22}$-GLP-1(7-37) OH, $Gly^8$-$Glu^{22}$-GLP-1(7-36)$NH_2$, $Val^8$-$Asp^{22}$-GLP-1(7-37) OH, $Val^8$-$Asp^{22}$-GLP-1(7-36)$NH_2$, $Gly^8$-$Asp^{22}$-GLP-1(7-37)OH, $Gly^8$-$Asp^{22}$-GLP-1(7-36)$NH_2$, $Val^8$-Lys -GLP-1(7-37)OH, $Val^8$-$Lys^{22}$-GLP-1(7-36)$NH_2$, $Gly^8$-$Lys^{22}$-GLP-1(7-37)OH, $Gly^8$-$Lys^{22}$-GLP-1(7-36)$NH_2$, $Leu^8$-$Glu^{22}$-GLP-1(7-37)OH, $Leu^8$-$Glu^{22}$-GLP-1(7-36)$NH_2$, $Ile^8$-$Glu^{22}$-GLP-1(7-37)OH, $Ile^8$-$Glu^{22}$-GLP-1(7-36)$NH_2$, Leu -Asp22-GLP-1(7-37)OH, $Leu^8$-$Asp^{22}$-GLP-1(7-36)$NH_2$, $Ile^8$-$Asp^{22}$-GLP-1(7-37)OH, $Ile^8$-$Asp^{22}$-GLP-1(7-36)$NH_2$, $Leu^8$-$Lys^{22}$-GLP-1(7-37)OH, Leu8-Lys22-GLP-1(7-36)$NH_2$, $Ile^8$-$Lys^{22}$-GLP-1(7-37)OH, $Ile^8$-$Lys^{22}$-GLP-1(7-36)$NH_2$, $Ser^8$-$Glu^{22}$-GLP-1(7-37)OH, $Ser^8$-$Glu^{22}$-GLP-1(7-36)$NH_2$, $Thr^8$-$Glu^{22}$-GLP-1(7-37)OH, $Thr^8$-$Glu^{22}$-GLP-1(7-36)$NH_2$, $Ser^8$-$Asp^{22}$-GLP-1(7-37)OH, $Ser^8$-$Asp^{22}$-GLP-1(7-36)$NH_2$, $Thr^8$-Asp22-GLP-1(7-37)OH, $Ser^8$-$Glu^{22}$-GLP-1(7-37)OH, $Ser^8$-$Glu^{22}$-GLP-1(7-36)$NH_2$, $Ser^8$-$Lys^{22}$-GLP-1(7-36)$NH_2$, $Thr^8$-$Lys^{22}$-GLP-1(7-37)OH, $Thr^8$-$Lys^{22}$-GLP-1(7-36)$NH_2$, $Glu^{22}$-GLP-1(7-37)OH, $Glu^{22}$-GLP-1(7-36)$NH_2$, $Asp^{22}$-GLP-1(7-37)OH, Asp22-GLP-1(7-36)$NH_2$, $Lys^{22}$-GLP-1(7-37)OH, $Lys^{22}$-GLP-1(7-36)$NH_2$, $Val^2$-$Ala^{27}$-GLP-1(7-37)OH, $Val^8$-$Glu^{22}$-$Ala^{27}$-GLP-1(7-37)OH, $Val^8$-$Glu^{30}$-GLP-1(7-37)OH, $Val^8$-$Glu^{30}$-GLP-1(7-36)$NH_2$, $Gly^8$-$Glu^{30}$-GLP-1(7-37)OH, $Gly^8$-$Glu^{30}$-GLP-1(7-36)$NH_2$, $Leu^8$-$Glu^{30}$-GLP-1(7-37)OH, $Leu^8$-$Glu^{30}$-GLP-1(7-36)$NH_2$, $Ile^8$-$Glu^{30}$-GLP-1(7-37)OH, $Ile^8$-$Glu^{30}$-GLP-1(7-36)$NH_2$, $Ser^8$-$Glu^{30}$-GLP-1(7-37)OH, $Ser^8$-$Glu^{30}$-GLP-1(7-36)$NH_2$, $Thr^8$-$Glu^{30}$-GLP-1(7-37)OH, $Thr^8$-$Glu^{30}$-GLP-1(7-36)$NH_2$, $Val^8$-$His^{37}$-GLP-1(7-37)OH, $Val^8$-$His^{37}$-GLP-1(7-36)$NH_2$, $Gly^8$-$His^{37}$-GLP-1(7-37)OH, $Gly^8$-$His^{37}$-GLP-1(7-36)$NH_2$, $Leu^8$-$His^{37}$-GLP-1(7-37)OH, $Leu^8$-$His^{37}$-GLP-1(7-36)$NH_2$, $Ile^8$-$His^{37}$-GLP-1(7-37)OH, $Ile^8$-$His^{37}$-GLP-1(7-36)$NH_2$, $Ser^8$-$His^{37}$-GLP-1(7-37)OH, $Ser^8$-$His^{37}$-GLP-1(7-36)$NH_2$, $Thr^8$-$His^{37}$-GLP-1(7-37)OH, $Thr^8$-$His^{37}$-GLP-1(7-36)$NH_2$.

Some preferred GLP-1 compounds of formula IX having multiple substitutions include GLP-1(7-37)OH wherein position 8 is valine or glycine, position 22 is glutamic acid, position 16 is tyrosine, leucine or tryptophan, position 18 is tyrosine, tryptophan, or isoleucine, position 25 is valine and position 33 is isoleucine. Other preferred GLP-1 compounds include the following: $Val^8$-$Tyr^{16}$-GLP-1(7-37)OH, $Val^8$-$Tyr^{12}$-$Glu^{22}$-GLP-1(7-37)OH, $Val^8$-$Tyr^{16}$-$Phe^{19}$-GLP-1(7-37)OH, $Val^8$-$Tyr^{16}$-$Glu^{22}$-GLP-1(7-37)OH, $Val^8$-$Trp^{16}$-$Glu^{22}$-GLP-1(7-37)OH, $Val^8$-$Leu^{16}$-$Glu^{22}$-GLP-1(7-37)OH, $Val^8$-$Ile^{16}$-$Glu^{22}$-GLP-1(7-37)OH, $Val^8$-$Phe^{16}$-$Glu^{22}$-GLP-1(7-37)OH; $Val^8$-$Trp^8$-$Glu^{22}$-GLP-1(7-37)OH, $Val^8$-$Tyr^8$-$Glu^{22}$-GLP-1(7-37)OH, $Val^8$-$Phe^{18}$-$Glu^{22}$-GLP-1(7-37)OH, and $Val^8$-$Ile^{18}$-$Glu^{22}$-GLP-1(7-37)OH.

The GLP-1 compounds of the present invention also encompass Exendin compounds. Exendin-3 and Exendin-4 are biologically active peptides first isolated from Helodermatidae lizard venoms and have been shown to bind the GLP-1 receptor and stimulate cAMP-dependent $H^+$ production in mammalian parietal cells. Exendin-3 and Exendin-4 are both 39 amino acid peptides which are approximately 53% homologous to GLP-1. They act as potent agonists of GLP-1 activity. Notably, an N-terminally truncated derivative of Exendin, known as Exendin(9-39 amino acids), is an inhibitor of Exendin-3, Exendin-4 and GLP-1.

An Exendin compound typically comprises a polypeptide having the amino acid sequence of Exendin-3, Exendin-4, or an analog or fragment thereof. Exendin-3 and Exendin-4 are disclosed in U.S. Pat. No. 5,424,286.

Exendin-3 has the amino acid sequence of SEQ ID NO: 9:

```
                                  (SEQ ID NO: 9)
 7   8   9  10  11  12  13  14  15  16  17
His-Ser-Asp-Gly-Thr-Phe-Thr-Ser-Asp-Leu-Ser-

18  19  20  21  22  23  24  25  26  27  28
Lys-Gln-Met-Glu-Glu-Glu-Ala-Val-Arg-Leu-Phe-

29  30  31  32  33  34  35  36  37  38  39
Ile-Glu-Trp-Leu-Lys-Asn-Gly-Gly-Pro-Ser-Ser-

40  41  42  43  44  45
Gly-Ala-Pro-Pro-Pro-Ser
```

Exendin-4 has the amino acid sequence of SEQ ID NO: 10:

```
                                 (SEQ ID NO: 10)
 7   8   9  10  11  12  13  14  15  16  17
His-Gly-Glu-Gly-Thr-Phe-Thr-Ser-Asp-Leu-Ser-

18  19  20  21  22  23  24  25  26  27  28
Lys-Gln-Met-Glu-Glu-Glu-Ala-Val-Arg-Leu-Phe-

29  30  31  32  33  34  35  36  37  38  39
Ile-Glu-Trp-Leu-Lys-Asn-Gly-Gly-Pro-Ser-Ser-

40  41  42  43  44  45
Gly-Ala-Pro-Pro-Pro-Ser
```

GLP-1 compounds also include Exendin fragments which are polypeptides obtained after truncation of one or more amino acids from the N-terminus and/or C-terminus of Exendin or an Exendin analog. Furthermore, GLP-1 compounds include Exendin polypeptides in which one or more amino acids have been added to the N-terminus and/or C-terminus of Exendin or fragments thereof. Exendin compounds of this type have up to about forty-five amino acids.

GLP-1 compounds also include "Exendin analogs." An Exendin analog has sufficient homology to Exendin-4, Exendin-3, or a fragment thereof such that the analog has insulinotropic activity. The activity of Exendin fragments and/or analogs can be assessed using in vitro assays such as those described in EP 619,322 and U.S. Pat. No. 5,120,712.

Preferably, an Exendin analog has the amino acid sequence of Exendin-4 or a fragment thereof, modified so that from one, two, three, four or five amino acids differ from the amino acid in corresponding position of Exendin-4 or the fragment of Exendin-4. In the nonmenclature used herein to designate Exendin compounds, the substituting amino acid and its position is indicated prior to the parent structure. For example, $Val^8$-Exendin-4 designates an Exendin compound in which the glycine normally found at position 8 of Exendin-4 has been replaced with valine.

Another preferred group of GLP-1 compounds is composed of GLP-1/Exendin-4 analogs of formula VIII (SEQ ID NO: 11).

```
                                (SEQ ID NO: 11)
7   8   9   10  11  12  13  14  15  16  17
Xaa-Xaa-Glu-Gly-Thr-Phe-Thr-Ser-Asp-Xaa-Ser-

18  19  20  21  22  23  24  25  26  27  28
Xaa-Xaa-Xaa-Glu-Xaa-Xaa-Ala-Xaa-Xaa-Xaa-Phe

29  30  31  32  33  34  35  36  37
Ile-Xaa-Trp-Leu-Xaa-Xaa-Gly-Xaa-R
formula VIII
```

wherein:

Xaa at position 7 is: L-histidine, D-histidine, desamino-histidine, 2-amino-histidine, β-hydroxy-histidine, homo-histidine, α-fluoromethyl-histidine or α-methyl-histidine;
Xaa at position 8 is: Gly, Ala, or Val;
Xaa at position 16 is: Leu or Val;
Xaa at position 18 is Lys or Ser;
Xaa at position 19 is: Gln or Tyr;
Xaa at position 20 is: Met or Leu;
Xaa at position 22 is: Glu or Gln;
Xaa at position 23 is: Glu, or Gln;
Xaa at position 25 is: Val or Ala;
Xaa at position 26 is: Arg or Lys;
Xaa at position 27 is Leu or Glu;
Xaa at position 30 is: Glu or Ala;
Xaa at position 33 is: Val or Lys;
Xaa at position 34 is: Asn or Lys;
Xaa at position 36 is: Gly or Arg; and
R at position 37 is: Gly, Pro, Pro-Ser-Ser-Gly-Ala-Pro-Pro-Pro-Ser, or is absent. The activity of 18 different species that fall within this genus is provided in Table 6.

Further Exendin-analogs that are useful for the present invention are described in PCT patent publications WO 99/25728 (Beeley et al.), WO 99/25727 Beeley et al.), WO 98/05351 (Young et al.), WO 99/40788 (Young et al.), WO 99/07404 (Beeley et al), and WO 99/43708 (Knudsen et al).

The GLP-1 fusion proteins of the present invention can comprise glycosylation sites. Glycosylation is a chemical modification wherein sugar moieties are added to the protein at specific sites. Glycosylation of proteins play a role in ensuring the correct charge, confirmation, and stability of maturing protein and can target the protein to the cell surface and eventual secretion of the protein. Most importantly, glycosylation effects the in vivo clearance rate for many proteins. Sugars can be O-linked or N-linked. Generally, O-linked sugars are added to the hydroxyl-group oxygen of serine and threonine, while N-linked sugars are added to the amide nitrogen of asparagine. The consensus site for N-glycosylation is Asn X1 X2 wherein X1 is any amino acid except Pro and X2 is Ser or Thr.

GLP-1 compounds are generally not glycosylated in vivo; however, interestingly the GLP-1 fusion proteins of the present invention that comprise a GLP-1 compound with a C terminal extension fused to an Fc sequence is glycosylated at the last serine in the C terminal extension (SSGAPPPS*) and at threonine at position 11 in the N terminal region of Fc (AEPKSCDKTHT*CPPC . . . ).

Heterologous Fc Fusion Proteins

The GLP-1 compounds described above can be fused directly or via a peptide linker to the Fc portion of an immunoglobulin.

Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W. H. Freeman and Co., 1992, the teachings of which are herein incorporated by reference. The Fc portion can further include one or more glycosylation sites. The amino acid sequence of a representative Fc protein containing a hinge region, CH2 and CH3 domains, and one N-glycosylation site at position 82 is shown in FIG. 1.

There are five types of human immunoglobulin Fc regions with different effect or and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which have different effect or functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

IgA can exist both in a monomeric and dimeric form held together by a J-chain. IgA is the second most abundant Ig in serum, but it has a half-life of only 6 days. IgA has three effect or functions. It binds to an IgA specific receptor on macrophages and eosinophils, which drives phagocytosis and degranulation, respectively. It can also fix complement via an unknown alternative pathway.

IgM is expressed as either a pentamer or a hexamer, both of which are held together by a J-chain. IgM has a serum half-life of 5 days. It binds weakly to C1q via a binding site located in its CH3 domain. IgD has a half-life of 3 days in serum. It is unclear what effect or functions are attributable to this Ig. IgE is a monomeric Ig and has a serum half-life of 2.5 days. IgE binds to two Fc receptors which drives degranulation and results in the release of proinflammatory agents.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to a GLP-1 compound.

The fusion proteins of the present invention can consist of single chain proteins or as multi-chain polypeptides. Two or more Fc fusion proteins can be produced such that they interact through disulfide bonds that naturally form between Fc regions. These multimers can be homogeneous with respect to the GLP-1 compound or they may contain different GLP-1 compounds fused at the N-terminus of the Fc portion of the fusion protein.

Regardless of the final structure of the fusion protein, the Fc or Fc-like region must serve to prolong the in vivo plasma half-life of the GLP-1 compound fused at the N-terminus. Furthermore, the fused, GLP-1 compound must retain some biological activity. An increase in half-life can be demonstrated using the method described in Example 7 wherein the half-life of the fusion protein is compared to the half-life of the GLP-1 compound alone. Biological activity can be determined by in vitro and in vivo methods known in the art. Representative biological assays are described in Examples 6, 8, and 9.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or C1q are indistinguishable from the rate of clearance of the parent wild-type antibody, indicating that the catabolic site is distinct from the sites involved in Fc receptor or C1q binding. [Wawrzynczak et al., (1992) *Molecular Immunology* 29:221]. Site-directed mutagenesis studies using a murine IgG1 Fc region suggested that the site of the IgG1 Fc region that controls the catabolic rate is located at the CH2-CH3 domain interface.

Based on these studies, Fc regions can be modified at the catabolic site to optimize the half-life of the fusion proteins. It is preferable that the Fc region used for the heterologous fusion proteins of the present invention be derived from an IgG1 or an IgG4 Fc region. It is even more preferable that the Fc region be IgG4 or derived from IgG4. Preferably the IgG Fc region contains both the CH2 and CH3 regions including the hinge region.

Heterologous Albumin Fusion Proteins

The GLP-1 compounds described above can be fused directly or via a peptide linker to albumin or an analog, fragment, or derivative thereof.

Generally the albumin proteins making up part of the fusion proteins of the present invention can be derived from albumin cloned from any species. However, human albumin and fragments and analogs thereof are preferred to reduce the risk of the fusion protein being immunogenic in humans. Human serum albumin (HSA) consists of a single non-glycosylated polypeptide chain of 585 amino acids with a formula molecular weight of 66,500. The amino acid sequence of human HSA is shown in FIG. 2. [See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747]. A variety of polymorphic variants as well as analogs and fragments of albumin have been described. [See Weitkamp, et al., (1973) Ann. Hum. Genet. 37:219]. For example, in EP 322,094, the inventors disclose various shorter forms of HSA. Some of these fragments include HSA(1-373), HSA(1-388), HSA(1-389), HSA(1-369), and HSA(1-419) and fragments between 1-369 and 1-419. EP 399,666 discloses albumin fragments that include HSA(1-177) and HSA(1-200) and fragments between HSA(1-177) and HSA(1-200).

It is understood that the heterologous fusion proteins of the present invention include GLP-1 compounds that are coupled to any albumin protein including fragments, analogs, and derivatives wherein such fusion protein is biologically active and has a longer plasma half-life than the GLP-1 compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the GLP-1 compound of interest.

The heterologous fusion proteins of the present invention encompass proteins having conservative amino acid substitutions in the GLP-1 compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

However, the term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, β-alanine, ornithine, GABA, etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

The incorporation of non-natural amino acids, including synthetic non-native amino acids, substituted amino acids, or one or more D-amino acids into the heterologous fusion proteins of the present invention can be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

In addition to structure/function analyses of the various polypeptides encompassed by the present invention, there are numerous factors that can be considered when selecting amino acids for substitution. One factor that can be considered in making such changes is the hydropathic index of amino acids. The importance of the hydropathic amino acid index in conferring interactive biological function on a protein has been discussed by Kyte and Doolittle (1982, *J. Mol. Biol*., 157: 105-132). It is accepted that the relative hydropathic character of amino acids contributes to the secondary structure of the resultant protein. This, in turn, affects the interaction of the protein with molecules such as enzymes, substrates, receptors, ligands, DNA, antibodies, antigens, etc. Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide, polypeptide, or protein can be substituted for other amino acids having a similar hydropathic index or score and produce a resultant peptide, etc., having similar or even improved biological activity. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant peptide, etc., having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the fusion proteins of the present invention can be based on the relative similarity of the amino acid side-chain substituents, for example, their hydrophobicity, hydrophilicity, charge, size, etc. Furthermore, substitutions can be made based on secondary structure propensity. For example, a helical amino acid can be replaced with an amino acid that would preserve the helical structure. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids.

General Methods for Making the Heterologous Fusion Proteins of the Present Invention Although the heterologous fusion proteins of the present invention can be made by a variety of different methods, recombinant methods are preferred. For purposes of the present invention, as disclosed and claimed herein, the following general molecular biology terms and abbreviations are defined below. The terms and abbreviations used in this document have their normal meanings unless otherwise designated. For example, "° C" refers to degrees Celsius; "mmol" refers to millimole or millimoles; "mg" refers to milligrams; "μg" refers to micrograms; "ml or mL" refers to milliliters; and "μl or μL" refers to microliters. Amino acids abbreviations are as set forth in 37 C.F.R. § 1.822 (b)(2) (1994).

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and thymidine, respectively, when they occur in DNA molecules. The abbreviations U,C,G, and A correspond to the 5'-monophosphate forms of the ribonucleosides uridine, cytidine, guanosine, and adenosine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

"Digestion" or "Restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

"Plasmid" refers to an extrachromosomal (usually) self-replicating genetic element. Plasmids are generally designated by a lower case "p" followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

"Recombinant DNA expression vector" as used herein refers to any recombinant DNA cloning vector in which a promoter to control transcription of the inserted DNA has been incorporated.

"Transcription" refers to the process whereby information contained in a nucleotide sequence of DNA is transferred to a complementary RNA sequence.

"Transfection" refers to the uptake of an expression vector by a host cell whether or not any coding sequences are, in fact, expressed. Numerous methods of transfection are known to the ordinarily skilled artisan, for example, calcium phosphate co-precipitation, liposome transfection, and electroporation. Successful transfection is generally recognized when any indication of the operation of this vector occurs within the host cell.

"Transformation" refers to the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., Molecular Cloning: A Laboratory Manual, (1989). Generally, when introducing DNA into Yeast the term transformation is used as opposed to the term transfection.

"Translation" as used herein refers to the process whereby the genetic information of messenger RNA (mRNA) is used to specify and direct the synthesis of a polypeptide chain.

"Vector" refers to a nucleic acid compound used for the transfection and/or transformation of cells in gene manipulation bearing polynucleotide sequences corresponding to appropriate protein molecules which, when combined with appropriate control sequences, confers specific properties on the host cell to be transfected and/or transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

"Complementary" or "Complementarity", as used herein, refers to pairs of bases (purines and pyrimidines) that associate through hydrogen bonding in a double stranded nucleic acid. The following base pairs are complementary: guanine and cytosine; adenine and thymine; and adenine and uracil.

"Hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however, constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

"Primer" refers to a nucleic acid fragment which functions as an initiating substrate for enzymatic or synthetic elongation.

"Promoter" refers to a DNA sequence which directs transcription of DNA to RNA.

"Probe" refers to a nucleic acid compound or a fragment, thereof, which hybridizes with another nucleic acid compound.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while short probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reactions more stringent, while lower temperatures less so. For additional details and explanation of stringency of hybridization reactions, see Ausubel et al., *Current Protocols in Molecular Biology*, Wiley Interscience Publishers, 1995.

"Stringent conditions" or "high stringency conditions", as defined herein, may be identified by those that (1) employ low ionic strength and high temperature for washing, for example, 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% ficoll/0.1% polyvinylpyrrolidone/50 mM sodium phosphate buffer at pH 6.5 with 750 mM sodium chloride/75 mm sodium citrate at 42° C.; or (3) employ 50% formamide, 5×SSC (750 mM sodium chloride, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C. with washes at 42° C. in 0.2×SSC (30 mM sodium chloride/3 mM sodium citrate) and 50% formamide at 55° C., followed by a high-stringency wash consisting of 0.1×SSC containing EDTA at 55° C.

"Moderately stringent conditions" may be identified as described by Sambrook et al. [Molecular Cloning: A Laboratory Manual, New York: Cold Spring Harbor Press, (1989)], and include the use of washing solution and hybridization conditions (e.g., temperature, ionic strength, and % SDS) less stringent than those described above. An example of moderately stringent conditions is overnight incubation at 37° C. in a solution comprising: 20% formamide, 5×SSC (750 mM sodium chloride, 75 mM sodium citrate), 50 mM sodium phosphate at pH 7.6, 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

"PCR" refers to the widely-known polymerase chain reaction employing a thermally-stable DNA polymerase.

"Leader sequence" refers to a sequence-of amino acids which can be enzymatically or chemically removed to produce the desired polypeptide of interest.

"Secretion signal sequence" refers to a sequence of amino acids generally present at the N-terminal region of a larger polypeptide functioning to initiate association of that polypeptide with the cell membrane compartments like endoplasmic reticulum and secretion of that polypeptide through the plasma membrane.

Construction of DNA Encoding the Heterologous Fusion Proteins of the Present Invention Wild-type albumin and Immunoglobulin proteins can be obtained from a variety of sources. For example, these proteins can be obtained from a cDNA library prepared from tissue or cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256. Some references disclosing albumin protein and DNA sequences include Meloun, et al. (1975) FEBS Letters 58:136; Behrens, et al. (1975) Fed. Proc. 34:591; Lawn, et al. (1981) Nucleic Acids Research 9:6102-6114; and Minghetti, et al. (1986) J. Biol. Chem. 261:6747

Screening a cDNA or genomic library with the selected probe may be conducted using standard procedures, such as described in Sambrook et al., *Molecular Cloning: A Laboratory Manual*, Cold Spring Harbor Laboratory Press, NY (1989). An alternative means to isolate a gene encoding an albumin or immunoglobulin protein is to use PCR methodology [Sambrook et al., supra; Dieffenbach et al., *PCR Primer: A Laboratory Manual*, Cold Spring Harbor Laboratory Press, NY (1995)]. PCR primers can be designed based on published sequences.

Generally the full-length wild-type sequences cloned from a particular species can serve as a template to create analogs, fragments, and derivatives that retain the ability to confer a longer plasma half-life on the GLP-1 compound that is part of the fusion protein. It is preferred that the Fc and albumin portions of the heterologous fusion proteins of the present invention be derived from the native human sequence in order to reduce the risk of potential immunogenicity of the fusion protein in humans.

In particular, it is preferred that the immunoglobulin portion of a fusion protein encompassed by the present invention contain only an Fc fragment of the immunoglobulin. Depending on whether particular effect or functions are desired and the structural characteristics of the fusion protein, an Fc fragment may contain the hinge region along with the CH2 and CH3 domains or some other combination thereof. These Fc fragments can be generated using PCR techniques with primers designed to hybridize to sequences corresponding to the desired ends of the fragment. Similarly, if fragments of albumin are desired, PCR primers can be designed which are complementary to internal albumin sequences. PCR primers can also be designed to create restriction enzyme sites to facilitate cloning into expression vectors.

DNA encoding the GLP-1 compounds of the present invention can be made by a variety of different methods including cloning methods like those described above as well as chemically synthesized DNA. Chemical synthesis may be attractive given the short length of the encoded peptide. The amino acid sequence for GLP-1 has been published as well as the sequence of the preproglucagon gene. [Lopez, et al. (1983) Proc. Natl. Acad. Sci., USA 80:5485-5489; Bell, et al. (1983) Nature, 302:716-718; Heinrich, G., et al. (1984) Endocrinol, 115:2176-2181; Ghiglione, M., et al. 91984) Diabetologia 27:599-600]. Thus, primers can be designed to PCR native GLP-1 compounds and fragments thereof.

The gene encoding a fusion protein can then be constructed by ligating DNA encoding a GLP-1 compound in-frame to DNA encoding an albumin or Fc protein. The gene encoding the GLP-1 compound and the gene encoding the albumin or Fc protein can also be joined in-frame via DNA encoding a linker peptide.

The in vivo function and stability of the heterologous fusion proteins of the present invention can be optimized by adding small peptide linkers to prevent potentially unwanted domain interactions. Although these linkers can potentially be any length and consist of any combination of amino acids, it is preferred that the length be no longer than necessary to prevent unwanted domain interactions and/or optimize biological activity and/or stability. Generally, the linkers should not contain amino acids with extremely bulky side chains or amino acids likely to introduce significant secondary structure. It is preferred that the linker be serine-glycine rich and be less than 30 amino acids in length. It is more preferred that the linker be no more than 20 amino acids in length. It is even more preferred that the linker be no more than 15 amino acids in length. A preferred linker contains repeats of the sequence Gly-Gly-Gly-Gly-Ser. It is preferred that there be between 2 and 6 repeats of this sequence. It is even more preferred that there be between 3 and 4 repeats of this sequence.

The DNA encoding wild-type GLP-1, albumin, and Fc polypeptides and fragments thereof can be mutated either before ligation or in the context of a cDNA encoding an entire fusion protein. A variety of mutagenesis techniques are well known in the art. For example, a mutagenic PCR method utilizes strand overlap extension to create specific base mutations for the purposes of changing a specific amino acid sequence in the corresponding protein. This PCR mutagenesis requires the use of four primers, two in the forward orientation (primers A and C and two in the reverse orientation (primers B and D). A mutated gene is amplified from the wild-type template in two different stages. The first reaction amplifies the gene in halves by performing an A to B reaction and a separate C to D reaction wherein the B and C primers target the area of the gene to be mutated. When aligning these primers with the target area, they contain mismatches for the bases that are targeted to be changed. Once the A to B and C to D reactions are complete, the reaction products are isolated and mixed for use as the template for the A to D reaction. This reaction then yields the full, mutated product.

Once a gene encoding an entire fusion protein is produced it can be cloned into an appropriate expression vector.

Specific strategies that can be employed to make the GLP-1 fusion proteins of the present invention are described in example 1.

General Methods to Recombinantly Express the Heterologous Fusion Proteins of the Present Invention Host cells are transfected or transformed with expression or cloning vectors described herein for heterologous fusion protein production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook, et al., supra. Methods of transfection are known to the ordinarily skilled artisan, for example, $CaPO_4$ and electroporation. General aspects of mammalian cell host system transformations have been described in U.S. Pat. No. 4,399,216. Transformations into yeast are typically carried out according to the method of van Solingen et al., *J Bact*. 130(2): 946-7 (1977) and Hsiao et al., *Proc. Natl. Acad. Sci. USA* 76(8): 3829-33 (1979). However, other methods for introducing DNA into cells, such as by nuclear microinjection, electroporation, bacterial protoplast fusion with intact cells, or polycations, e.g., polybrene or polyomithine, may also be used. For various techniques for transforming mammalian cells, see Keown, et al., *Methods in Enzymology* 185: 527-37 (1990) and Mansour, et al., *Nature* 336(6197): 348-52 (1988).

Suitable host cells for cloning or expressing the nucleic acid (e.g., DNA) in the vectors herein include prokaryote, yeast, or higher eukaryote cells. Suitable prokaryotes include but are not limited to eubacteria, such as Gram-negative or Gram-positive organisms, for example, Enterobacteriacea such as *E. coli*. Various *E. coli* strains are publicly available, such as *E. coli* K12 strain MM294 (ATCC 3 1.446); *E. coli* X1776 (ATCC 3 1.537); *E. coli* strain W3 110 (ATCC 27.325) and K5 772 (ATCC 53.635). Other suitable prokaryotic host cells include Enterobacteriaceae such as *Escherichia*, e.g., *E. coli, Enterobacter, Erwinia, Klebisella, Proteus, Salmonella*, e.g., *Salmonella typhimurium, Serratia*, e.g., *Serratia marcescans*, and *Shigeila*, as well as *Bacilli* such as *B. subtilis* and *B. lichentformis* (e.g., *B. licheniformis* 4 1 P disclosed in DD266,7 10, published 12 Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3 110 may be modified to effect a genetic mutation in the genes encoding proteins endogenous to the host, with examples of such hosts including *E. coli* W3110 strain 1A2, which has the complete genotype ronA; *E. coli* W3110 strain 9E4, which has the complete genotype ton4 ptr3; *E. coli* W3110 strain 27C7 (ATCC 55,244), which has the complete genotype tonA, ptr3 phoA El5 (argF-lac) I69 degp ompT/can'; *E. coli* W3110 strain 40B4, which is strain 37D6 with a non-kanamycin resistant degp deletion mutation; and an *E. coli* strain having mutant periplasmic protease disclosed in U.S. Pat. No. 4,946,783 issued Aug. 7, 1990. Alternatively, in vivo methods of cloning, e.g., PCR or other nucleic acid polymerase reactions, are suitable.

In addition to prokaryotes, eukaryotic microbes such as filamentous fungi or yeast are suitable cloning or expression hosts for fusion protein vectors. *Saccharomyces cerevisiae* is a commonly used lower eukaryotic host microorganism. Others include *Schizosaccharomyces pombe* [Beach and Nurse, *Nature* 290: 140-3 (1981); EP 139,383 published May 2, 1995]; Muyveromyces hosts [U.S. Pat. No. 4,943,529; Fleer, et al., *Bio/Technology* 9(10): 968-75 (1991)] such as, e.g., *K lactis* (MW98-8C, CBS683, CBS4574) [de Louvencourt et al., *J. Bacteriol.* 154(2): 737-42 (1983)]; *K. fiagilis* (ATCC 12,424), *K. bulgaricus* (ATCC 16,045), *K wickeramii* (ATCC 24,178), *K. waltii* (ATCC 56,500), *K. drosophilarum* (ATCC 36.906) [Van den Berg et al., *Bio/Technology* 8(2): 135-9 (1990)]; *K. thermotoierans*, and *K. marxianus*; yarrowia (EP 402,226); *Pichia pastoris* (EP 183,070) [Sreekrishna et al., *J. Basic Microbiol.* 28(4): 265-78 (1988)]; Candid; *Trichoderma reesia* (EP 244,234); *Neurospora crassa* [Case, et al., *Proc. Natl. Acad Sci. USA* 76(10): 5259-63 (1979)]; Schwanniomyces such as *Schwanniomyces occidentulis* (EP 394,538 published Oct. 31, 1990); and filamentous fungi such as, e.g., *Neurospora, Penicillium, Tolypocladium* (WO 91/00357 published Jan. 10, 1991), and Aspergillus hosts such as *A. nidulans* [Ballance et al., *Biochem. Biophys. Res. Comm.* 112(1): 284-9 (1983)]; Tilburn, et al., *Gene* 26(2-3): 205-21 (1983); Yelton, et al., *Proc. Natl. Acad. Sci. USA* 81(5): 1470-4 (1984)] and A. niger [Kelly and Hynes, EMBO J. 4(2): 475-9 (1985)]. Methylotropic yeasts are selected from the genera consisting of *Hansenula, Candida, Kloeckera, Pichia, Saccharomyces, Torulopsis*, and *Rhodotoruia*. A list of specific species that are exemplary of this class of yeast may be found in C. Antony, *The Biochemistry of Methylotrophs* 269 (1982).

Suitable host cells for the expression of the fusion proteins of the present invention are derived from multicellular organisms. Examples of invertebrate cells include insect cells such as Drosophila S2 and Spodoptera Sp, Spodoptera high5 as well as plant cells. Examples of useful mammalian host cell lines include Chinese hamster ovary (CHO) and COS cells. More specific examples include monkey kidney CVl line transformed by SV40 (COS-7, ATCC CRL 1651); human embryonic kidney line [293 or 293 cells subcloned for growth in suspension culture, Graham, et al., *J. Gen Virol*., 36(1): 59-74 (1977)]; Chinese hamster ovary cells/-DHFR [CHO, Urlaub and Chasin, *Proc. Natl. Acad. Sci. USA*, 77(7): 4216-20 (1980)]; mouse sertoli cells [TM4, Mather, *Biol. Reprod*. 23(1):243-52 (1980)]; human lung cells (W138. ATCC CCL 75); human liver cells (Hep G2, HB 8065); and mouse mammary tumor (MMT 060562, ATCC CCL51). The selection of the appropriate host cell is deemed to be within the skill in the art.

The fusion proteins of the present invention may be recombinantly produced directly, or as a protein having a signal sequence or other additional sequences which create a specific cleavage site at the N-terminus of the mature fusion protein. In general, the signal sequence may be a component of the vector, or it may be a part of the fusion protein-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* cc-factor leaders, the latter described in U.S. Pat. No. 5,010,182), or acid phosphatase leader, the *C. albicans* glucoamylase leader (EP 362,179), or the signal described in WO 90/13646. In mammalian cell expression, mammalian signal sequences may be used to direct secretion of the protein, such as signal sequences from secreted polypeptides of the same or related species as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2u plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement autotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the fusion protein-encoding nucleic acid, such as DHFR or thymidine kinase. An appropriate host cell when wild-type DHFR is employed is the CHO cell line deficient in DHFR activity, prepared and propagated as described [Urlaub and Chasin, *Proc. Natl. Acad. Sci. USA*, 77(7): 4216-20 (1980)]. A suitable selection gene for use in yeast is the trpl gene present in the yeast plasmid YRp7 [Stinchcomb, et al., *Nature* 282(5734): 39-43 (1979); Kingsman, et al., Gene 7 (2): 141-52 (1979); Tschumper, et al., *Gene* 10 (2): 157-66 (1980)]. The trpl gene provides a selection marker for a mutant strain of yeast lacking the ability to grow in tryptophan, for example, ATCC No. 44076 or PEPC1 [Jones, *Genetics* 85: 23-33 (1977)].

Expression and cloning vectors usually contain a promoter operably linked to the fusion protein-encoding nucleic acid sequence to direct mRNA synthesis. Promoters recognized by a variety of potential host cells are well known. Promoters suitable for use with prokaryotic hosts include the β-lactamase and lactose promoter systems [Chang, et al., *Nature* 275 (5681): 617-24 (1978); Goeddel, et al., *Nature* 281 (5732): 544-8 (1979)], alkaline phosphatase, a tryptophan (up) promoter system [Goeddel, *Nucleic Acids Res.* 8(18): 4057-74 (1980); EP 36,776 published Sep. 30, 1981], and hybrid promoters such as the tat promoter [deBoer, et al., *Proc. Natl. Acad. Sci. USA* 80(1): 21-5 (1983)]. Promoters for use in bacterial systems also will contain a Shine-Dalgarno (S.D.) sequence operably linked to the DNA encoding the fusion protein.

Examples of suitable promoting sequences for use with yeast hosts include the promoters for 3-phosphoglycerate kinase [Hitzeman, et al., *J. Biol. Chem.* 255(24): 12073-80 (1980)] or other glycolytic enzymes [Hess et al., *J. Adv. Enzyme Reg.* 7: 149 (1968); Holland, *Biochemistry* 17(23): 4900-7 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Transcription of fusion protein-encoding mRNA from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a polynucleotide encoding a fusion protein by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-ketoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the fusion protein coding sequence but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and occasionally 3' untranslated regions of eukaryotic or viral DNAs or cDNAs. These regions contain nucleotide segments transcribed as polyadenylated fragments in the untranslated portion of the mRNA encoding the fusion protein.

Various forms of a fusion protein may be recovered from culture medium or from host cell lysates. If membrane-bound, it can be released from the membrane using a suitable detergent solution (e.g., Triton-X 100) or by enzymatic cleavage. Cells employed in expression of a fusion protein can be disrupted by various physical or chemical means, such as freeze-thaw cycling, sonication, mechanical disruption, or cell lysing agents.

Purification of the Heterologous Fusion Proteins of the Present Invention

Once the heterologous fusion proteins of the present invention are expressed in the appropriate host cell, the analogs can be isolated and purified. The following procedures are exemplary of suitable purification procedures: fractionation on carboxymethyl cellulose; gel filtration such as Sephadex G-75; anion exchange resin such as DEAE or Mono-Q; cation exchange such as CM or Mono-S; protein A sepharose to remove contaminants such as IgG; metal chelating columns to bind epitope-tagged forms of the polypeptide; reversed-phase HPLC; chromatofocusing; silica gel; ethanol precipitation; and ammonium sulfate precipitation.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, N.Y. (1982). The purification step(s) selected will depend on the nature of the production process used and the particular fusion protein produced. For example, fusion proteins comprising an Fc fragment can be effectively purified using a Protein A or Protein G affinity matix. Low or high pH buffers can be used to elute the fusion protein from the affinity matrix. Mild elution conditions will aid in preventing irreversible denaturation of the fusion protein. Imidazole-containing buffers can also be used. Example 3 describes some successful purification protocols for the fusion proteins of the present invention.

Characterization of the Heterologous Fusion Proteins of the Present Invention

Numerous methods exist to characterize the fusion proteins of the present invention. Some of these methods include: SDS-PAGE coupled with protein staining methods or immunoblotting using anti-IgG or anti-HSA antibodies. Other methods include matrix assisted laser desporption/ionization-mass spectrometry (MALDI-MS), liquid chromatography/mass spectrometry, isoelectric focusing, analytical anion exchange, chromatofocussing, and circular dichroism to name a few. A representative number of heterologous fusion proteins were characterized using SDS-PAGE coupled with immunoblotting as well as mass spectrometry (See examples 4 and 5 and FIGS. 3 and 4).

For example table 3 (see example 5) illustrates the calculated molecular mass for a representative number of fusion proteins as well as the mass as determined by mass spectrometry. In addition, FIGS. 3 and 4 illustrate molecular weights of a representative number of fusion proteins as determined by SDS PAGE. All heterologous fusion proteins tested were expressed and secreted transiently. In addition, the Igκ signal sequence was cleaved to yield proteins with the correct N-terminus.

Further, table 3 illustrates that in some instances the mass determined by mass spectrometry is greater than expected. This is the result of glycosylation of the Fc portion and the C terminal extension. Enzymatic digestion of the fusion proteins followed by reversed-phase HPLC and mass spectrometry can identify peptide fractions that contain sugar moieties. These fractions can then be N-terminal amino acid sequenced to identify the potential glycosylation site. For example, characterization of Exendin-4-Fc (SEQ ID NO: 29) shows that the serine at position 39 and threonine at position 50 are O-linked glycosylated and the asaparagine at position 122 is N-linked glycosylated.

A representative number of GLP-1 fusion proteins were also tested for activity. Numerous methods exist to detect GLP-1 activity in vitro and in vivo (see examples 6, 7, 8, and 9). Table 4 (example 6) illustrates GLP-1 receptor activity associated with several GLP-1 fusions. The numbers are relative to the activity associated with Val$^{8}$-GLP-1(7-37)OH. All fusion proteins tested had GLP-1 receptor activity. A low level of in vitro activity is not necessarily indicative of a weak effect in vivo. Because of the substantial increase in the half-life of these fusion proteins, weak in vitro activity is not generally a predictor of weak in vivo activity. FIG. 7 and example 7 illustrate the prolonged half-life associated with the fusion proteins of the present invention. For example, Val$^{8}$-GLP-1-Fc had a half-life of approximately 45 hours in monkeys, Val$^{8}$-GLP-1-HSA had a half-life of about 87 hours in monkeys, Gly$^{8}$-Glu$^{22}$-GLP-1-CEx-Linker-IgG1 had a half-life after IV administration of approximately 55 hours in dogs, and Gly$^{8}$-Glu$^{22}$-GLP-1-CEx-Linker-IgG1 had a half-life after SC administration of approximately 38 hours in dogs.

Compositions of the Invention:

Physical stability is also an essential feature for therapeutic protein formulations. GLP-1 compounds have been especially difficult to manufacture and formulate due to structural changes that occur during processing. For example, some GLP-1 compounds have a general tendency to aggregate. In addition, it has been shown that some GLP-1 compounds convert from a soluble and active α-helix form to an insoluble and potentially inactive β-sheet form. The fusion of GLP-1 compounds to large proteins such as the Fc region of an IgG or albumin not only acts to increase the half-life of the GLP-1 compound, but also contributes to the physical and conformational stability of the GLP-1 compound. For example, Val$^{8}$-GLP-1-Linker-HSA in PBS is stable at 37° C. out to about 30 days.

The heterologous fusion proteins of the present invention may be formulated with one or more excipients. The active fusion proteins of the present invention may be combined with a pharmaceutically acceptable buffer, and the pH adjusted to provide acceptable stability, and a pH acceptable for administration such as parenteral administration.

Optionally, one or more pharmaceutically-acceptable anti-microbial agents may be added. Meta-cresol and phenol are preferred pharmaceutically-acceptable microbial agents. One or more pharmaceutically-acceptable salts may be added to adjust the ionic strength or tonicity. One or more excipients may be added to further adjust the isotonicity of the formulation. Glycerin is an example of an isotonicity-adjusting excipient. Pharmaceutically acceptable means suitable for administration to a human or other animal and thus, does not contain toxic elements or undesirable contaminants and does not interfere with the activity of the active compounds therein.

A pharmaceutically-acceptable salt form of the heterologous fusion proteins of the present invention may be used in the present invention. Acids commonly employed to form acid addition salts are inorganic acids such as hydrochloric acid, hydrobromic acid, hydriodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Preferred acid addition salts are those formed with mineral acids such as hydrochloric acid and hydrobromic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Administration of Compositions:

Administration may be via any route known to be effective by the physician of ordinary skill. Peripheral, parenteral is one such method. Parenteral administration is commonly understood in the medical literature as the injection of a dosage form into the body by a sterile syringe or some other mechanical device such as an infusion pump. Peripheral parenteral routes can include intravenous, intramuscular, subcutaneous, and intraperitoneal routes of administration.

The heterologous fusion proteins of the present invention may also be amenable to administration by oral, rectal, nasal, or lower respiratory routes, which are non-parenteral routes. Of these non-parenteral routes, the lower respiratory route and the oral route are preferred.

The fusion proteins of the present invention can be used to treat a wide variety of diseases and conditions. The fusion proteins of the present invention primarily exert their biological effects by acting at a receptor referred to as the "GLP-1 receptor." Subjects with diseases and/or conditions that respond favorably to GLP-1 receptor stimulation or to the administration of GLP-1 compounds can-therefore be treated with the GLP-1 fusion proteins of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

An "effective amount" of a GLP-1 compound is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a GLP-1 compound for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

The dose of fusion protein effective to normalize a patient's blood glucose will depend on a number of factors, among which are included, without limitation, the subject's sex, weight and age, the severity of inability to regulate blood glucose, the route of administration and bioavailability, the pharmacokinetic profile of the fusion protein, the potency, and the formulation.

The present invention comprises GLP-1 compounds that have improved biochemical and biophysical properties by virtue of being fused to an albumin protein, an albumin fragment, an albumin analog, a Fc protein, a Fc fragment, or a Fc analog. These heterologous proteins can be successfully expressed in host cells, retain signaling activities associated with activation of the GLP-1 receptor, and have prolonged half-lives.

The following examples are presented to further describe the present invention. The scope of the present invention is not to be construed as merely consisting of the following examples. Those skilled in the art will recognize that the particular reagents, equipment, and procedures described are merely illustrative and are not intended to limit the present invention in any manner.

EXAMPLE 1

Construction of DNA Encoding Heterologous Fusion Proteins

EXAMPLE 1a

Construction of DNA Encoding Val$^8$-GLP-1(7-37)-Fc

A Fc portion of human IgG1 was isolated from a cDNA library and contains the full hinge region and the CH2 and CH3 domains. A fragment containing 696 base pairs of this Fc portion of human IgG1 was subcloned into the NheI and Eco47III sites of mammalian expression vector pJB02 to create pJB02/Fc (see FIG. 5). DNA encoding the Igκ secretion signal sequence fused to Val$^8$-GLP-1(7-37) was generated by in vitro hybridization of four overlapping and complementary oligonucleotides:

5'-CTAGCCACCATGGAGACAGACACACTCCTGCTATGGGTACTGCTGCTCTGGGTT [SEQ ID NO:12]
CCAGGTTCCACTGGTGACCAGTG-3'

5'-GAGGGCACCTTCACCTCCGACGTGTCCTCCTATCTGGAGGGCCAGGCCGCCAAG [SEQ ID NO:13]
GAGTTCATCGCCTGGCTGGTGAAGGGAAGAGGC-3'

5'-TGAAGGTGCCCTCCACGTGGTCACCAGTGGAACCTGGAACCCAGAGCAGCAGTA [SEQ ID NO:14]
CCCATAGCAGGAGTGTGTCTGTCTCCATGGTGG-3'

5'-GCCTCTTCCCTTCACCAGCCAGGCGATGAACTCCTTGGCGGCCTGGCCCTCCAG [SEQ ID NO:15]
ATAGGAGGACACGTCGGAGG-3'

The hybridization reaction was carried out using equivalent amounts of each oligonucleotide (1 pm/μl final concentration for each oligo). The mixture of oligonucleotides was heated for 5 min at 100° C. in ligation buffer (50 mM Tris-HCl, pH 7.5, 10 mM $MgCl_2$, 10 mM DTT, 1 mM ATP, 25 μg/ml bovine serum albumin) and then cooled over at least 2 hours to 30° C.

The resulting hybridization product was ligated for 2 hours at room temperature or overnight at 16° C. to the pJB02/Fc vector backbone which had been digested with NheI and Eco47III. The ligation products were used to transform competent XL-1 Blue cells (Stratagene). Recombinant plasmids were screened for the presence of peptide coding inserts by digesting clones with NcoI (encoding the Kozak sequence and first Met of the signal peptide) and sequenced. The resulting expression plasmid used for transfection assays was denoted pJB02-V8-GLP-1-Fc (FIG. 5).

EXAMPLE 1b

Construction of DNA Encoding Val$^{8}$-GLP-1(7-37)-HSA

EXAMPLE 1d

Construction of DNA Encoding Exendin-4-Fc

The plasmid pJB02/Fc was prepared as described in Example 1a. DNA encoding the Igκ signal sequence fused to Exending-4 was generated by in vitro hybridization of the following overlapping and complementary oligonucleotides:

```
5'-CTAGCCACCATGGAGACAGACACACTCCTGCTATGGGTACTGCTGCTCTG      [SEQ ID NO:16]
GGTTCCAGGTTCCACCGGTCAC-3'

5'-GGAGAGGGAACCTTCACCAGCGACCTGAGCAAGCAGATGGAGGAGGAGGCCGT   [SEQ ID NO:17]
GAGACTG-3'

5'-TTCATCGAGTGGCTGAAGAACGGAGGACCAAGCAGCGGAGCCCCTCCTCCT     [SEQ ID NO:18]
AGC-3'

5'-GAACCTGGAACCCAGAGCAGCAGTACCCATAGCAGGAGTGTGTCTGTCTCCA    [SEQ ID NO:19]
TGGTGG-3'

5'-CTCCTCCTCCATCTGCTTGCTCAGGTCGCTGGTGAAGGTTCCCTCTCCGTGA    [SEQ ID NO:20]
CCGGTG-3'

5'-GCTAGGAGGAGGGGCTCCGCTGCTTGGTCCTCCGTTCTTCAGCCACTCGAT     [SEQ ID NO:21]
GAACAGTCTCACGGC-3'
```

The plasmid HSA/pcDNA3.1GS was purchased from Invitrogen (Catalog # H-M12523M-pcDNA3.1/GS) and used as a template to isolate the cDNA encoding human serum albumin (HSA). The HSA cDNA was prepared using PCR wherein the DNA encoding the leader sequence as well as the six amino acid pro-peptide was removed from the 5' end. In addition, stop codons were added directly at the 3' end of the HSA coding sequence. Finally, restriction enzyme sites were engineered at the 5' and 3' end to facilitate cloning. The HSA DNA sequence present in the original vector purchased from Invitrogen contained a single base change in the 3' region of the gene (position 667) compared to the native human sequence. This change would result in a codon for Asn instead of Asp. Thus, using the strand overlapping PCR mutagenesis method discussed above, the codon was changed to code for Asp at this position. The resulting HSA encoding DNA was cloned into the NheI and HindIII sites of pJB02 to create pJB02-HSA (FIG. 6).

The Igκ leader sequence fused to the Val$^{8}$-GLP-1(7-37) sequence was generated as discussed in Example 1a. This DNA was ligated into the NheI and FspI sites of pJB02-HSA to create pJB02-Val$^{8}$-GLP-1-HSA.

EXAMPLE 1c

Construction of DNA Encoding Val$^{8}$-GLP-1(7-37)-Linker-HSA

The vector pJB02-HSA was prepared as discussed in Example 1b. DNA encoding the linker sequence [GGGGS]$_{3}$ was ligated in frame to the 5' end of the HSA encoding DNA to create pJB02-linker-HSA (FIG. 7). DNA encoding the Igκ leader sequence and fused to the Val$^{8}$-GLP-1(7-37) sequence and the 5' part of the linker sequence was generated as discussed in Example 1a. This DNA was ligated into the NheI and BspEI sites of pJB02 to create pJB02- Val$^{8}$-GLP-1-linker-HSA.

The hybridization reaction was carried out as described in Example 1a. The hybridized product was ligated to the pJB02 vector which had been digested with NheI and Eco47III as described in Example 1a to create pJB02-Exendin-4-Fc.

EXAMPLE 1e

Construction of DNA Encoding Exendin-4-HSA

The plasmid pJB02-HSA was prepared as described in Example 1b. DNA encoding the Igκ signal sequence fused to Exending-4 was generated by in vitro hybridization of the same overlapping and complementary oligonucleotides described in Example 1d. Hybridization reactions were also carried out as described above. DNA was cloned into unique NheI and FspI sites in pJB02-HSA to create pJB02-Exendin-4-HSA.

EXAMPLE 1f

Construction of DNA Encoding Exendin-4-linker-HSA

The plasmid pJB02-linker-HSA was constructed as described in Example 1c. DNA encoding the Igκ signal sequence fused to Exendin-4 and the 5' part of the linker sequence was generated as in Example 1d. This DNA was cloned into unique NheI and BspEI sites in pJB02-linker-HSA to create pJB02-Exendin-4-linker-HSA.

EXAMPLE 1g

Construction of DNA Encoding Val$^{8}$-GLP-1/C-Ex-Fc

The plasmid pJB02-Exendin-4-Fc was prepared as described in Example 1d. The Exendin-4 encoding DNA was excised from the vector with AgeI and Eco47III. The Val$^{8}$-GLP-1/C-Ex encoding DNA was generated by in vitro hybridization of the following overlapping and complementary oligonucleotides:

```
5'-CCGGTCACGTGGAGGGCACCTTCACCTCCGACGTGTCCTCCTATCTGGA   [SEQ ID NO:22]
GGGCCAGGCCGCCA-3'

5'-AGGAATTCATCGCCTGGCTGGTGAAGGGCCGGGGCAGCAGCGG         [SEQ ID NO:23]
AGCCCCTCCTCCTAGC-3'

5'-CTCCAGATAGGAGGACACGTCGGAGGTGAAGGTGCCCTCCAC          [SEQ ID NO:24]
GTGA-3'

5'-GCTAGGAGGAGGGGCTCCGCTGCTGCCCCGGCCCTTCACCAGCCAGGCGA  [SEQ ID NO:25]
TGAATTCCTTGGCGGCCTGGCC-3'
```

The hybridization reaction was carried out as described in Example 1a. The hybridized product was ligated in place of Exendin-4 in the pJB02-Exendin-4-Fc expression vector to create pJB02-Val$^{8}$-GLP-1/C-Ex-Fc.

EXAMPLE 1h

Construction of DNA Encoding Val$^{8}$-Glu -GLP-1-Fc

The plasmid pJB02-Exendin-4-Fc was prepared as described in Example 1d. The Exendin-4 encoding DNA was excised from the vector with AgeI and Eco47III. The Val$^{8}$-Glu$^{22}$-GLP-1 encoding DNA was generated by in vitro hybridization of the following overlapping and complementary oligonucleotides:

```
5'-CCGGTCACGTGGAGGGCACCTTCACCTCCGACGTGTCCTCCTATCTCGA [SEQ ID NO:26]
GGAGCAGGCCGCCA-3'

5'-AGGAGTTCATCGCCTGGCTGGTGAAGGGCCGGGGC-3'            [SEQ ID NO:27]

5'-GCCCCGGCCCTTCACCAGCCAGGCGATGAACTCCTTGGCGGCC       [SEQ ID NO:28]
TGCTC-3'

5'-CTCGAGATAGGAGGACACGTCGGAGGTGAAGGTGCCCT            [SEQ ID NO:29]
CCACGTGA-3'
```

The hybridization reaction was carried out as described in Example 1a. The hybridized product was ligated in place of Exendin-4 in the pJB02-Exendin-4-Fc expression vector to create pJB02-Val$^{8}$-Glu$^{22}$-GLP-1-Fc.

EXAMPLE 1i

Construction of DNA Encoding Val$^{8}$-Glu GLP-1/C-Ex-Fc

The plasmid pJB02-Exendin-4-Fc was prepared as described in Example 1d. The Exendin-4 encoding DNA was excised from the vector with AgeI and Eco47III. The Val$^{8}$-Glu$^{22}$GLP-1/C-Ex encoding DNA was generated by in vitro hybridization of the following overlapping and complementary oligonucleotides:

```
5'-CCGGTCACGTGGAGGGCACCTTCACCTCCGACGTGTCCTCCTATCTCGA   [SEQ ID NO:30]
GGAGCAGGCCGCCA-3'

5'-AGGAATTCATCGCCTGGCTGGTGAAGGGCCGGGGCAGCAGCGGA        [SEQ ID NO:31]
GCCCCTCCTCCTAGC-3'

5'-CTCGAGATAGGAGGACACGTCGGAGGTGAAGGTGCCC               [SEQ ID NO:32]
TCCACGTGA-3'

5'-GCTAGGAGGAGGGGCTCCGCTGCTGCCCCGGCCCTTCACCAGCCAGGCGA  [SEQ ID NO:33]
TGAATTCCTTGGCGGCCTGCTC-3'
```

The hybridization reaction was carried out as described in Example 1a. The hybridized product was ligated in place of Exendin-4 in the pJB02-Exendin-4-Fc expression vector to create pJB02-Val$^8$-Glu$^{22}$-GLP-1/C-Ex-Fc.

EXAMPLE 1j

Construction of DNA Encoding Gly$^8$-GLP-1-Fc

The plasmid pJB02-Exendin-4-Fc was prepared as described in Example 1d. The Exendin-4 encoding DNA was excised from the vector with AgeI and Eco47III. The Gly$^8$-GLP-1 encoding DNA was generated by in vitro hybridization of the following overlapping and complementary oligonucleotides:

```
5'-CCGGTCACGGCGAGGGCACCTTCACTAGTGACGTGTCCTCCTATCTGGA [SEQ ID NO:34]
GGGCCAGGCCGCCA-3'

5'-AGGAGTTCATCGCCTGGCTGGTGAAGGGCCGGGGC-3'           [SEQ ID NO:35]

5'-CTCCAGATAGGAGGACACGTCACTAGTGAAGGTGCCCTC           [SEQ ID NO:36]
GCCGTGA-3'

5'-GCCCCGGCCCTTCACCAGCCAGGCGATGAACTCCTTGGCGGC        [SEQ ID NO:37]
CTGGCC-3'
```

The hybridization reaction was carried out as described in Example 1a. The hybridized product was ligated in place of Exendin-4 in the pJB02-Exendin-4-Fc expression vector to create pJB02-Gly$^8$-GLP-1-Fc.

EXAMPLE 2

Expression of Heterologous Fusion Proteins

Expression of the fusion proteins encoded by the DNA constructs of Example 1 was carried out by transiently transfecting HEK 293EBNA cells (both adherent and suspension). Cells were counted and seeded 24 hours prior to transfection. The transfection cocktail was prepared by mixing FuGene™ 6 transfection reagent (Roche Molecular Biochemicals, catalog # 1814443) with OptiMEM (Gibco/BRL) and incubating at room temperature for 5 min at which point DNA was added and the cocktail was incubated for an additional 15 min. Immediately before transfection, fresh growth media was added to the plate. Tables 1 and 2 provide further transfection details.

TABLE 1

Reagents used in transient transfections of 293EBNA cells.

| Tissue culture vessel | Number of cells seeded | DNA (μg) | FuGene (μl) | OptiMEM media (ml) | Vol. of growth medium (ml) |
|---|---|---|---|---|---|
| 35 mm | $5 \times 10^5$ | 1.5 | 9 | 0.102 | 2 |
| 100 mm | $2 \times 10^6$ | 12 | 73 | 0.820 | 10 |
| 700 $cm^2$ (RB) | $2 \times 10^7$ | 65 | 400 | 4.0 | 100 |

TABLE 2

Media composition

| Growth and transfection medium | Harvesting medium |
|---|---|
| DMEM F12 3:1 | Hybritech base |
| 5% FBS | 1 mM $Ca^{2+}$ |
| 20 mM HEPES | 20 mM HEPES |
| 2 mM L-glutamine | 1 μg/ml Nuselin (human insulin) |
| 50 μg/ml geneticin (G418 NEO) | 1 μg/ml human transferrin |
| 50 μg/ml tobromycin | 50 μg/ml tobromycin |

For small-scale transfections (35 mm-10 mm vessels), cells were rinsed with PBS and switched to harvesting media 24 hours post-transfection and media was collected and replaced every 24 hours for several days. In the case of large-scale transfections (700 $cm^2$ roller bottles), the roller bottles were rinsed with PBS 48 hours post-transfection and changed to harvesting media. Media was collected and changed every 24 hours for at least 10 consecutive days. Routinely, only 10 harvests were used for subsequent protein purification.

EXAMPLE 3

Purification of Heterologous Fusion Proteins

EXAMPLE 3a

Purification of Val$^8$-GLP-1-Fc

Approximately 4.5 liters of conditioned medium (fusion protein expression level approximately 20 μg/ml) from large-scale transfections was filtered using a CUNO filter system and concentrated to 250 ml using a ProFlux tangential flow filtration system with a 10 K filter membrane. Val$^8$-GLP-1-Fc was captured with a 5 ml HiTrap protein A column in 1×PBS, pH 7.4 at a flow rate of 2 ml/min and eluted with 50 mM citric acid pH 3.3. Fractions (1 ml) were collected in tubes containing 4 ml 1×PBS and 100 μl 1 M Tris pH 8.

Fractions containing the fusion protein, as determined by SDS-PAGE and reverse phase-HPLC on Zorbax C8, were pooled and applied to a Superdex 75 60/60 column in 1×PBS pH 7.4 at a flow rate of 10 ml/min. Positive fractions (20 mls/tube) were collected and pooled. Pooled fractions were then subjected to C4 Reverse Phase Chromatography in 0.1% TFA water at a flow rate of 3 ml/min. Val$^8$-GLP-1-Fc was eluted using a gradient from 5% B (0.1% TFA in acetonitrile) to 100% B in 70 min. Eluant fractions (3 mls/tube) were collected. Acetonitrile was removed by vacuum drying and 1 ml of $H_2O$ was added. The purified sample (approximately 32 mls) was dialyzed twice against 4 liters of 1×PBS pH 7.4.

The dialyzed sample was then filtered using a MILLEX-GV 0.22 um Filter Unit and concentration was determined using absorption at 280 nm.

EXAMPLE 3b

Purification of $Val^8$-GLP-1-HSA or $Val^8$-GLP-1-Linker-HSA

Approximately 6.5 liters of conditioned medium (fusion protein expression level approximately 10 μg/ml) was filtered using a CUNO filter system and concentrated to 380 mls using a ProFlux tangential flow filtration system with a 10 K filter membrane.

The fusion protein was captured using a 50 ml Fast Flow Q column (Pharmacia) in 20 mM Tris pH 7.4 at a flow rate of 5 ml/min. Protein was eluted using a gradient: from 0% to 50% 20 mM Tris pH 7.4, 1M NaCl in 10 CV, then to 100% B in 2 CV.

Fractions containing the fusion protein were pooled and subjected to C4 Reverse Phase Chromatography in 0.1% TFA water at a flow rate of 5 ml/min. The fusion protein was eluted using a gradient from 20% B (0.1% TFA in acetonitrile) to 90% B in 120 min. Fractions (3.5 ml/tube) were collected. Acetonitrile was removed by vacuum drying.

Approximately 9 mls of pooled sample was diluted with 1×PBS pH 7.4 to 40 ml and dialyzed against 4 liters of 1×PBS pH 7.4 overnight. The sample was filtered and concentration was determined by absorption at 280 nm.

EXAMPLE 3c

Purification of Exendin-4-Fc

Approximately 4 liters of conditioned medium (fusion protein expression level approximately 8 μg/ml) was filtered using a CUNO filter system and concentrated to 250 mls using a ProFlux tangential flow filtration system with a 30K filter membrane.

Exendin-4-Fc was captured with a 5 ml HiTrap protein A column in 1×PBS, pH 7.4 at a flow rate of 2 ml/min and eluted with 50 mM citric acid pH 3.3. Fractions containing the fusion protein were pooled, filtered, and dialyzed against 4 liters of 1×PBS over night. The dialyzed sample was then applied to a Superdex 75 60/60 column in 1×PBS pH 7.4, 0.5M NaCl at a flow rate of 10 ml/min. Fractions (20 ml/tube) containing the fusion protein were collected, pooled, and concentrated to about 1 mg/ml. Concentrated samples were then filtered using a MILLEX-GV 0.22 um Filter Unit.

EXAMPLE 3d

Purification of Exendin-4-HSA and Exendin-4-Linker-HSA

Approximately 1.1 liters of conditioned medium (fusion protein expression level approximately 6 μg/ml) was filtered using a CUNO filter system and concentrated to 175 mls using a ProFlux tangential flow filtration system with a 30K filter membrane.

The fusion protein was captured using a 5 ml HiTrap Q-sepharose column (Pharmacia) in 20 mM Tris pH 7.4 at a flow rate of 2 ml/min. Protein was eluted using a gradient from 0% to 50% 20 mM Tris pH 7.4, 1M NaCl in 12 CV and then to 100% B in 4 CV.

Fractions containing the fusion protein were pooled and subjected to C4 Reverse Phase Chromatography in 0.1% TFA water at a flow rate of 5 ml/min. The fusion protein was eluted using a gradient from 10% B (0.1% TFA in acetonitrile) to 100% B in 70 min. Fractions (10 ml/tube) containing the fusion protein were collected. Acetonitrile was removed using a vacuum dryer.

Approximately 8 mls of pooled sample was dialyzed against 4 liters of 1×PBS pH 7.4 overnight. The sample was filtered and concentration was determined by absorption at 280 nm. The dialyzed sample was then applied to a Superdex 200 26/60 column in 1×PBS pH 7.4, 0.5 M NaCl at a flow rate of 2 ml/min. Fractions (3 ml/tube) containing the fusion protein were collected, pooled, concentrated, and filtered.

EXAMPLE 4

Characterization of Fusion Proteins by SDS PAGE

SDS-PAGE followed by immunoblotting was used to analyze both purified fusion protein as well as conditioned medium from cells transfected with various fusion protein expression vectors. SDS-PAGE was performed on a Novex Powerease 500 system using Novex 16% Tris-Glycine Precast gels (EC6498), running buffer (10×, LC2675) and sample buffer (L2676). Samples were reduced with 50 mM DTT and heated 3-5 min at 95° C. prior to loading.

After running the SDS-PAGE gel, water and transfer buffer (1×Tris-Glycine Seprabuff (Owl Scientific Cat. No. ER26-S) with 20% methanol) were used to rinse SDS from the gels. A Novex transfer apparatus was used with PVDF (BioRad, Cat. No. 162-0174) and nitrocellulose membranes (BioRad, Cat. No. 1703965 or 1703932). Transfer was carried out at room temperature for 90 min at 30-35 V. Membranes were blocked in 1×PBS with 0.1% Tween-20 (Sigma, Cat. No. P-7949) and 5% Milk (BioRad, Cat. No. 170-6404) for 1-12 hours at 4° C. Antibodies are diluted into 1×PBS +5% Milk and the blots are incubated in these solutions for 1-2 h at 4° C. Between incubations, the blots are washed four times for 5 min each with 1×PBS and 0.2% Tween-20 at room temperature. PBS was made from either GIBCO 10×PBS (Cat No. 70011), to give a final composition of 1 mM monobasic potassium phosphate, 3 mM dibasic sodium phosphate, 153 mM sodium chloride, pH 7.4, or PBS pouches from Sigma (Cat. No. 1000-3), to give 120 mM NaCl, 2.7 mM KCl and 10 mM phosphate, pH 7.4 at 25° C.

The primary antibodies were either a polycolonal goat anti-IgG1 or rabbit anti-HSA. The secondary antibody was either an anti-goat IgG HRP or an anti-rabbit IgG HRP. The secondary antibody was diluted 1:5000. An ECL system (Amersham Pharmacia Biotech, Cat. No. RN2108 and Cat. No. RPN1674H) was used for developing blots.

FIG. 3A compares purified Fc protein to conditioned media from pJB02-$Val^8$-GLP-1-Fc and pJB02-Exendin-4-Fc transfected cells. The decrease in mobility is consistent with the increased size due to the GLP-1 portion of the fusion protein. FIG. 3B similarly compares purified HSA with conditioned media from cells transfected with pJB02-$Val^8$-GLP-2-HSA, pJB02- $Val^8$-GLP-1-Linker-HSA, pJB02-Exendin-4-HSA, or pJB02-Exendin-4-Linker-HSA. FIG. 4 identifies purified fusion protein preparations.

EXAMPLE 5

Characterization of Fusion Proteins Using Mass Spectrometry

All experiments were performed on a Micromass Tof-Spec-2E mass spectrometer equipped with Time Lag Focusing electronics, a Reflectron (used in analysis of the 0-8000 Da peptide range), a Linear detector (used during high mass/good signal analysis), and Post Acceleration Detector (or P.A.D., used for high mass/extremely low signal analysis) The effective path length of the instrument in Linear mode is 1.2 meters, in Reflectron mode it is 2.3 meters. Two dual micro-channel plate detectors are fitted for linear and reflectron mode detection. The laser used is a Laser Science Inc. VSL-337i nitrogen laser operating at 337 nm at 5 laser shots per second. All data were acquired using a 2 GHz, 8 bit internal digitizer and up to 50 laser shots were averaged per spectrum.

The instrument was operated in linear mode for the analysis of the GLP-1 fusion proteins in question. The linear detector is a device that detects ions that travel down the flight tube of the MALDI-ToF-MS instrument. It measures the ion abundance over time and sends a signal to the digitizer for conversion. The digitizer is an analog-to-digital converter that allows the signal from the mass spectrometer to be transferred to the computer, where it is reconstructed into a usable m/z spectrum.

A recrystallized saturated sinapinic acid solution (diluted in 50/50 Acn/$H_2O$ and 0.1% TFA) was utilized as the ionization matrix. Sinapinic acid is a proper matrix for proteins above 10 kDa. Mass appropriate reference proteins were used for internal and external calibration files in order to obtain accurate mass determinations for the samples analyzed. Samples were all analyzed using a 1:2 sample to matrix dilution. The instrument was initially set up under the following linear detector conditions:

| | | | |
|---|---|---|---|
| Source Voltage: | 20.0 keV | Pulse Voltage: | 3.0 keV |
| Extraction Voltage: | 20.0 keV | Laser Coarse: | 50 |
| Focus Voltage: | 16.0 keV | Laser Fine: | 50 |
| Linear detector: | 3.7 keV | | |
| P.A.D.: | (off 1ine) | | |

These settings were modified (as needed) to give the best signal/noise ratio and highest resolution. Table 3 provides a characterization of different GLP-1 fusion proteins.

TABLE 3

| Fusion Protein | Expected Mass (KDa) | Mass determined by Mass Spec (kDa) |
|---|---|---|
| Val$^8$-GLP-1-IgG1 | 59.08 | 61.94 |
| Val$^8$-Glu$^{22}$-GLP-1-IgG1 | 59.23 | 63.61 |
| Gly$^8$-GLP-1-IgG1 | 59.00 | 62.93 |
| Val$^8$-GLP-1-CEx-IgG1 | 60.45 | 65.1-65.6 |
| Val$^8$-Glu$^{22}$-GLP-1-CEx-IgG1 | 60.69 | 65.86 |
| Exendin-4-IgG1 | 60.69 | 65.86 |
| Val$^8$-GLP-1-Linker-HSA | 70.70 | 69.89, 70.74 |

TABLE 3-continued

| Fusion Protein | Expected Mass (KDa) | Mass determined by Mass Spec (kDa) |
|---|---|---|
| Exendin-4-HSA | 70.56 | 70.62 |
| Exendin-4-Linker-HSA | 71.56 | 71.62 |

CEx refers to a C-terminal extension and comprises the sequence of Ser-Ser-Gly-Ala-Pro-Pro-Pro-Ser.

Linker is Gly-Gly-Gly-Gly-Ser-Gly-Gly-Gly-Gly-Ser-Gly- Gly-Gly-Gly-Ser.

EXAMPLE 6

Activity of Heterologous Fusion Proteins

The ability of the fusion proteins of the present invention to activate the GLP-1 receptor was assessed using in vitro assays such as those described in EP 619,322 to Gelfand, et al., and U.S. Pat. No. 5,120,712, respectively. The activity of these compounds relative to the activity of Val$^8$-GLP-1(7-37)OH is reported in Table 4. FIG. 8 represents in vitro dose response curves for Val$^8$-GLP-1 and Exendin-4 fusion proteins. In addition, Table 5a and 5b provide the in vitro activity of a large group of GLP-1 analogs that can be fused to an Fc or an albumin protein to make biologically active fusion proteins. These activities are compared to GLP-1(7-37)OH.

TABLE 4

In vitro activity of GLP-1 fusion proteins

| Fusion Protein | In Vitro Activity (% of Val$^8$-GLP-1) |
|---|---|
| Val$^8$-GLP-1-IgG1 | 1 |
| Exendin-4-IgG1 | 240 |
| Val$^8$-GLP-1-Linker-HSA | 0.2 |
| Exendin-4-HSA | 20 |
| Exendin-4-Linker-HSA | 90 |
| Exendin-4 | 500 |
| Val$^8$-Glu$^{22}$-GLP-1-IgG1 | 3.7 |
| Gly$^8$-GLP-1-IgG1 | 3.3 |
| Val$^8$-GLP-1-CEx-IgG1 | 3.3 |
| Val$^8$-Glu$^{22}$-GLP-1-CEx-IgG1 | 29 |
| Gly$^8$-Glu$^{22}$-GLP-1-C2-IgG1 | 75 |
| Gly$^8$-Glu$^{22}$-GLP-1-CEx-Linker-IgG1 | 150 |
| Exendin-4-C2-IgG1 | 250 |
| Exendin-4-Linker-IgG1 | 330 |
| Gly$^8$-Glu$^{22}$-GLP-1-CEx-Linker-HSA | 4 |
| Gly$^8$-Glu$^{22}$-GLP-1-CEx-Linker-IgG4 | 80 |

CEx refers to a C-terminal extension and comprises the sequence of Ser-Ser-Gly-Ala-Pro-Pro-Pro-Ser.

Linker is Gly-Gly-Gly-Gly-Ser-Gly-Gly-Gly-Gly-Ser-Gly-Gly-Gly-Gly-Ser

C2 is Ser-Ser-Gly-Ala-Ser-Ser-Gly-Ala.

The amino acid sequences of the fusion proteins described in Tables 3 and 4 are represented in SEQ ID NO: 13 to SEQ ID NO: 31.

Val$^8$-GLP-1-Human serum albumin amino acid sequence is represented by SEQ ID NO: 13.

```
                                              [SEQ ID NO: 13]
  1 HVEGTFTSDV SSYLEGQAAK EFIAWLVKGR GDAHKSEVAH RFKDLGEENF KALVLIAFAQ

 61 YLQQCPFEDH VKLVNEVTEF AKTCVADESA ENCDKSLHTL FGDKLCTVAT LRETYGEMAD

121 CCAKQEPERN ECFLQHKDDN PNLPRLVRPE VDVMCTAFHD NEETFLKKYL YEIARRHPYF

181 YAPELLFFAK RYKAAFTECC QAADKAACLL PKLDELRDEG KASSAKQRLK CASLQKFGER

241 AFKAWAVARL SQRFPKAEFA EVSKLVTDLT KVHTECCHGD LLECADDRAD LAKYICENQD

301 SISSKLKECC EKPLLEKSHC IAEVENDEMP ADLPSLAADF VESKDVCKNY AEAKDVFLGM

361 FLYEYARRHP DYSVVLLLRL AKTYETTLEK CCAAADPHEC YAKVFDEFKP LVEEPQNLIK

421 QNCELFEQLG EYKFQNALLV RYTKKVPQVS TPTLVEVSRN LGKVGSKCCK HPEAKRMPCA

481 EDYLSVVLNQ LCVLHEKTPV SDRVTKCCTE SLVNRRPCFS ALEVDETYVP KEFNAETFTF

541 HADICTLSEK ERQIKKQTAL VELVKHKPKA TKEQLKAVMD DFAAFVEKCC KADDKETCFA

601 EEGKKLVAAS QAALGL
```

Val$^8$-GLP-1-Linker-Human serum albumin amino acid sequence is represented by SEQ ID NO: 14.

```
                                              [SEQ ID NO: 14]
  1 HVEGTFTSDV SSYLEGQAAK EFIAWLVKGR GGGGGSGGGG SGGGGSDAHK SEVAHRFKDL

 61 GEENFKALVL IAFAQYLQQC PFEDHVKLVN EVTEFAKTCV ADESAENCDK SLHTLFGDKL

121 CTVATLRETY GEMADCCAKQ EPERNECFLQ HKDDNPNLPR LVRPEVDVMC TAFHDNEETF

181 LKKYLYEIAR RHPYFYAPEL LFFAKRYKAA FTECCQAADK AACLLPKLDE LRDEGKASSA

241 KQRLKCASLQ KFGERAFKAW AVARLSQRFP KAEFAEVSKL VTDLTKVHTE CCHGDLLECA

301 DDRADLAKYI CENQDSISSK LKECCEKPLL EKSHCIAEVE NDEMPADLPS LAADFVESKD

361 VCKNYAEAKD VFLGMFLYEY ARRHPDYSVV LLLRLAKTYE TTLEKCCAAA DPHECYAKVF

421 DEFKPLVEEP QNLIKQNCEL FEQLGEYKFQ NALLVRYTKK VPQVSTPTLV EVSRNLGKVG

481 SKCCKHPEAK RMPCAEDYLS VVLNQLCVLH EKTPVSDRVT KCCTESLVNR RPCFSALEVD

541 ETYVPKEFNA ETFTFHADIC TLSEKERQIK KQTALVELVK HKPKATKEQL KAVMDDFAAF

601 VEKCCKADDK ETCFAEEGKK LVAASQAALG L
```

Gly$^8$-Glu$^{22}$-GLP-1-CEx-Linker-Human serum albumin amino acid sequence is represented by SEQ ID NO: 15.

```
                                              [SEQ ID NO: 15]
  1 HGEGTFTSDV SSYLEEQAAK EFIAWLVKGR GSSGAPPPSG GGGGSGGGGS GGGGSDAHKS

 61 EVAHRFKDLG EENFKALVLI AFAQYLQQCP FEDHVKLVNE VTEFAKTCVA DESAENCDKS

121 LHTLFGDKLC TVATLRETYG EMADCCAKQE PERNECFLQH KDDNPNLPRL VRPEVDVMCT

181 AFHDNEETFL KKYLYEIARR HPYFYAPELL FFAKRYKAAF TECCQAADKA ACLLPKLDEL

241 RDEGKASSAK QRLKCASLQK FGERAFKAWA VARLSQRFPK AEFAEVSKLV TDLTKVHTEC

301 CHGDLLECAD DRADLAKYIC ENQDSISSKL KECCEKPLLE KSHCIAEVEN DEMPADLPSL

361 AADFVESKDV CKNYAEAKDV FLGMFLYEYA RRHPDYSVVL LLRLAKTYET TLEKCCAAAD

421 PHECYAKVFD EFKPLVEEPQ NLIKQNCELF EQLGEYKFQN ALLVRYTKKV PQVSTPTLVE

481 VSRNLGKVGS KCCKHPEAKR MPCAEDYLSV VLNQLCVLHE KTPVSDRVTK CCTESLVNRR
```

-continued

```
541 PCFSALEVDE TYVPKEFNAE TFTFHADICT LSEKERQIKK QTALVELVKH KPKATKEQLK

601 AVMDDFAAFV EKCCKADDKE TCFAEEGKKL VAASQAALGL
```

Exendin-4-Human serum albumin amino acid sequence is represented by SEQ ID NO: 16.

```
                                                      [SEQ ID NO: 16]
  1 HGEGTFTSDL SKQMEEEAVR LFIEWLKNGG PSSGAPPPSD AHKSEVAHRF KDLGEENFKA

 61 LVLIAFAQYL QQCPFEDHVK LVNEVTEFAK TCVADESAEN CDKSLHTLFG DKLCTVATLR

121 ETYGEMADCC AKQEPERNEC FLQHKDDNPN LPRLVRPEVD VMCTAFHDNE ETFLKKYLYE

181 IARRHPYFYA PELLFFAKRY KAAFTECCQA ADKAACLLPK LDELRDEGKA SSAKQRLKCA

241 SLQKFGERAF KAWAVARLSQ RFPKAEFAEV SKLVTDLTKV HTECCHGDLL ECADDRADLA

301 KYICENQDSI SSKLKECCEK PLLEKSHCIA EVENDEMPAD LPSLAADFVE SKDVCKNYAE

361 AKDVFLGMFL YEYARRHPDY SVVLLLRLAK TYETTLEKCC AAADPHECYA KVFDEFKPLV

421 EEPQNLIKQN CELFEQLGEY KFQNALLVRY TKKVPQVSTP TLVEVSRNLG KVGSKCCKHP

481 EAKRMPCAED YLSVVLNQLC VLHEKTPVSD RVTKCCTESL VNRRPCFSAL EVDETYVPKE

541 FNAETFTFHA DICTLSEKER QIKKQTALVE LVKHKPKATK EQLKAVMDDF AAFVEKCCKA

601 DDKETCFAEE GKKLVAASQA ALGL
```

Exendin-4-Linker-Human serum albumin amino acid sequence is represented by SEQ ID NO: 17.

```
                                                      [SEQ ID NO: 17]
  1 HGEGTFTSDL SKQMEEEAVR LFIEWLKNGG PSSGAPPPSG GGGGSGGGGS GGGGSDAHKS

 61 EVAHRFKDLG EENFKALVLI AFAQYLQQCP FEDHVKLVNE VTEFAKTCVA DESAENCDKS

121 LHTLFGDKLC TVATLRETYG EMADCCAKQE PERNECFLQH KDDNPNLPRL VRPEVDVMCT

181 AFHDNEETFL KKYLYEIARR HPYFYAPELL FFAKRYKAAF TECCQAADKA ACLLPKLDEL

241 RDEGKASSAK QRLKCASLQK FGERAFKAWA VARLSQRFPK AEFAEVSKLV TDLTKVHTEC

301 CHGDLLECAD DRADLAKYIC ENQDSISSKL KECCEKPLLE KSHCIAEVEN DEMPADLPSL

361 AADFVESKDV CKNYAEAKDV FLGMFLYEYA RRHPDYSVVL LLRLAKTYET TLEKCCAAAD

421 PHECYAKVFD EFKPLVEEPQ NLIKQNCELF EQLGEYKFQN ALLVRYTKKV PQVSTPTLVE

481 VSRNLGKVGS KCCKHPEAKR MPCAEDYLSV VLNQLCVLHE KTPVSDRVTK CCTESLVNRR

541 PCFSALEVDE TYVPKEFNAE TFTFHADICT LSEKERQIKK QTALVELVKH KPKATKEQLK

601 AVMDDFAAFV EKCCKADDKE TCFAEEGKKL VAASQAALGL
```

Val[8]-GLP-1-IgG1 amino acid sequences represented by SEQ ID NO: 18.

```
                                                      [SEQ ID NO: 18]
  1 HVEGTFTSDV SSYLEGQAAK EFIAWLVKGR GAEPKSCDKT HTCPPCPAPE LLGGPSVFLF

 61 PPKPKDTLMI SRTPEVTCVV VDVSHEDPEV KFNWYVDGVE VHNAKTKPRE EQYNSTYRVV

121 SVLTVLHQDW LNGKEYKCKV SNKALPAPIE KTISKAKGQP REPQVYTLPP SREEMTKNQV

181 SLTCLVKGFY PSDIAVEWES NGQPENNYKT TPPVLDSDGS FFLYSKLTVD KSRWQQGNVF

241 SCSVMHEALH NHYTQKSLSL SPGK
```

Val$^{8}$-GLP-1-Cex-IgG1 amino acid sequence is represented by SEQ ID NO: 19.

```
                                                              [SEQ ID NO: 19]
  1 HVEGTFTSDV SSYLEGQAAK EFIAWLVKGR GSSGAPPPSA EPKSCDKTHT CPPCPAPELL

 61 GGPSVFLFPP KPKDTLMISR TPEVTCVVVD VSHEDPEVKF NWYVDGVEVH NAKTKPREEQ

121 YNSTYRVVSV LTVLHQDWLN GKEYKCKVSN KALPAPIEKT ISKAKGQPRE PQVYTLPPSR

181 EEMTKNQVSL TCLVKGFYPS DIAVEWESNG QPENNYKTTP PVLDSDGSFF LYSKLTVDKS

241 RWQQGNVFSC SVMHEALHNH YTQKSLSLSP GK
```

Val$^{8}$-Glu$^{22}$GLP-1-IgG1 amino acid sequence is represented by SEQ ID NO: 20.

```
                                                              [SEQ ID NO: 20]
  1 HVEGTFTSDV SSYLEEQAAK EFIAWLVKGR GAEPKSCDKT HTCPPCPAPE LLGGPSVFLF

 61 PPKPKDTLMI SRTPEVTCVV VDVSHEDPEV KFNWYVDGVE VHNAKTKPRE EQYNSTYRVV

121 SVLTVLHQDW LNGKEYKCKV SNKALPAPIE KTISKAKGQP REPQVYTLPP SREEMTKNQV

181 SLTCLVKGFY PSDIAVEWES NGQPENNYKT TPPVLDSDGS FFLYSKLTVD KSRWQQGNVF

241 SCSVMHEALH NHYTQKSLSL SPGK
```

Val$^{8}$-Glu$^{22}$GLP-1-CEx-IgG1 amino acid sequence is represented by SEQ ID NO: 21.

```
                                                              [SEQ ID NO: 21]
  1 HVEGTFTSDV SSYLEEQAAK EFIAWLVKGR GSSGAPPPSA EPKSCDKTHT CPPCPAPELL

 61 GGPSVFLFPP KPKDTLMISR TPEVTCVVVD VSHEDPEVKF NWYVDGVEVH NAKTKPREEQ

121 YNSTYRVVSV LTVLHQDWLN GKEYKCKVSN KALPAPIEKT ISKAKGQPRE PQVYTLPPSR

181 EEMTKNQVSL TCLVKGFYPS DIAVEWESNG QPENNYKTTP PVLDSDGSFF LYSKLTVDKS

241 RWQQGNVFSC SVMHEALHNH YTQKSLSLSP GK
```

Gly$^{8}$-Glu$^{22}$GLP-1-C2-IgG1 amino acid sequence is represented by SEQ ID NO: 22.

```
                                                              [SEQ ID NO: 22]
  1 HGEGTFTSDV SSYLEEQAAK EFIAWLVKGR GSSGASSGAA EPKSCDKTHT CPPCPAPELL

 61 GGPSVFLFPP KPKDTLMISR TPEVTCVVVD VSHEDPEVKF NWYVDGVEVH NAKTKPREEQ

121 YNSTYRVVSV LTVLHQDWLN GKEYKCKVSN KALPAPIEKT ISKAKGQPRE PQVYTLPPSR

181 EEMTKNQVSL TCLVKGFYPS DIAVEWESNG QPENNYKTTP PVLDSDGSFF LYSKLTVDKS

241 RWQQGNVFSC SVMHEALHNH YTQKSLSLSP GK
```

Gly$^{8}$-Glu$^{22}$GLP-1-CEx-Linker-IgG1 amino acid sequence is represented by SEQ ID NO: 23.

```
                                                              [SEQ ID NO: 23]
  1 HGEGTFTSDV SSYLEEQAAK EFIAWLVKGR GSSGAPPPSG GGGSGGGGSG GGGSAEPKSC

 61 DKTHTCPPCP APELLGGPSV FLFPPKPKDT LMISRTPEVT CVVVDVSHED PEVKFNWYVD

121 GVEVHNAKTK PREEQYNSTY RVVSVLTVLH QDWLNGKEYK CKVSNKALPA PIEKTISKAK
```

-continued

```
181 GQPREPQVYT LPPSREEMTK NQVSLTCLVK GFYPSDIAVE WESNGQPENN YKTTPPVLDS

241 DGSFFLYSKL TVDKSRWQQG NVFSCSVMHE ALHNHYTQKS LSLSPGK
```

Gly[8]-Glu[22]GLP-1-CEx-Linker-IgG4 amino acid sequence is represented by SEQ ID NO: 24.

```
                                                     [SEQ ID NO: 24]
  1 HGEGTFTSDV SSYLEEQAAK EFIAWLVKGR GSSGAPPPSG GGGSGGGGSG GGGSAESKYG

 61 PPCPSCPAPE FLGGPSVFLF PPKPKDTLMI SRTPEVTCVV VDVSQEDPEV QFNWYVDGVE

121 VHNAKTKPRE EQFNSTYRVV SVLTVLHQDW LNGKEYKCKV SNKGLPSSIE KTISKAKGQP

181 REPQVYTLPP SQEEMTKNQV SLTCLVKGFY PSDIAVEWES NGQPENNYKT TPPVLDSDGS

241 FFLYSRLTVD KSRWQEGNVF SCSVMHEALH NHYTQKSLSL SLGK
```

Gly[8]-Glu[22]GLP-1-CEx-2Linker-IgG1 amino acid sequence is represented by SEQ ID NO: 25.

```
                                                     [SEQ ID NO: 25]
  1 HGEGTFTSDV SSYLEEQAAK EFIAWLVKGR GSSGAPPPSG GGGSGGGGSG GGGSGGGGSG

 61 GGGSGGGGSA EPKSCDKTHT CPPCPAPELL GGPSVFLFPP KPKDTLMISR TPEVTCVVVD

121 VSHEDPEVKF NWYVDGVEVH NAKTKPREEQ YNSTYRVVSV LTVLHQDWLN GKEYKCKVSN

181 KALPAPIEKT ISKAKGQPRE PQVYTLPPSR EEMTKNQVSL TCLVKGFYPS DIAVEWESNG

241 QPENNYKTTP PVLDSDGSFF LYSKLTVDKS RWQQGNVFSC SVMHEALHNH YTQKSLSLSP

301 GK
```

Gly[8]-Glu[22]GLP-1-2Linker-IgG1 amino acid sequence is represented by SEQ ID NO: 26.

```
                                                     [SEQ ID NO: 26]
  1 HGEGTFTSDV SSYLEEQAAK EFIAWLVKGR GGGGGSGGGG SGGGGSGGGG SGGGGSGGGG

 61 SAEPKSCDKT HTCPPCPAPE LLGGPSVFLF PPKPKDTLMI SRTPEVTCVV VDVSHEDPEV

121 KFNWYVDGVE VHNAKTKPRE EQYNSTYRVV SVLTVLHQDW LNGKEYKCKV SNKALPAPIE

181 KTISKAKGQP REPQVYTLPP SREEMTKNQV SLTCLVKGFY PSDIAVEWES NGQPENNYKT

241 TPPVLDSDGS FFLYSKLTVD KSRWQQGNVF SCSVMHEALH NHYTQKSLSL SPGK
```

Gly[8]-Glu[22]GLP-1-2CEx-IgG1 amino acid sequence is represented by SEQ ID NO: 27.

```
                                                     [SEQ ID NO: 27]
  1 HGEGTFTSDV SSYLEEQAAK EFIAWLVKGR GSSGAPPPSS SGAPPPSAEP KSCDKTHTCP

 61 PCPAPELLGG PSVFLFPPKP KDTLMISRTP EVTCVVVDVS HEDPEVKFNW YVDGVEVHNA

121 KTKPREEQYN STYRVVSVLT VLHQDWLNGK EYKCKVSNKA LPAPIEKTIS KAKGQPREPQ

181 VYTLPPSREE MTKNQVSLTC LVKGFYPSDI AVEWESNGQP ENNYKTTPPV LDSDGSFFLY

241 SKLTVDKSRW QQGNVFSCSV MHEALHNHYT QKSLSLSPGK
```

$Gly^8$-$Glu^{22}$-$Val^{25}$-$Ile^{33}$GLP-1-CEx-Linker-IgG1 amino acid sequence is represented by SEQ ID NO: 28.

```
                                                    [SEQ ID NO: 28]
  1 HGEGTFTSDV SSYLEEQAVK EFIAWLIKGR GSSGAPPPSG GGGSGGGGSG GGGSAEPKSC

 61 DKTHTCPPCP APELLGGPSV FLFPPKPKDT LMISRTPEVT CVVVDVSHED PEVKFNWYVD

121 GVEVHNAKTK PREEQYNSTY RVVSVLTVLH QDWLNGKEYK CKVSNKALPA PIEKTISKAK

181 GQPREPQVYT LPPSREEMTK NQVSLTCLVK GFYPSDIAVE WESNGQPENN YKTTPPVLDS

241 DGSFFLYSKL TVDKSRWQQG NVFSCSVMHE ALHNHYTQKS LSLSPGK
```

Exendin-4-IgG1 amino acid sequence is represented by SEQ ID NO: 29.

```
                                                    [SEQ ID NO: 29]
  1 HGEGTFTSDL SKQMEEEAVR LFIEWLKNGG PSSGAPPPSA EPKSCDKTHT CPPCPAPELL

 61 GGPSVFLFPP KPKDTLMISR TPEVTCVVVD VSHEDPEVKF NWYVDGVEVH NAKTKPREEQ

121 YNSTYRVVSV LTVLHQDWLN GKEYKCKVSN KALPAPIEKT ISKAKGQPRE PQVYTLPPSR

181 EEMTKNQVSL TCLVKGFYPS DIAVEWESNG QPENNYKTTP PVLDSDGSFF LYSKLTVDKS

241 RWQQGNVFSC SVMHEALHNH YTQKSLSLSP GK
```

Exendin-4-C2-IgG1 amino acid sequence is represented by SEQ ID NO: 30.

```
                                                    [SEQ ID NO: 30]
  1 HGEGTFTSDL SKQMEEEAVR LFIEWLKNGG PSSGASSGAA EPKSCDKTHT CPPCPAPELL

 61 GGPSVFLFPP KPKDTLMISR TPEVTCVVVD VSHEDPEVKF NWYVDGVEVH NAKTKPREEQ

121 YNSTYRVVSV LTVLHQDWLN GKEYKCKVSN KALPAPIEKT ISKAKGQPRE PQVYTLPPSR

181 EEMTKNQVSL TCLVKGFYPS DIAVEWESNG QPENNYKTTP PVLDSDGSFF LYSKLTVDKS

241 RWQQGNVFSC SVMHEALHNH YTQKSLSLSP GK
```

Exendin-4-Linker-IgG1 amino acid sequence is represent by SEQ ID NO: 31.

```
                                                    [SEQ ID NO: 31]
  1 HGEGTFTSDL SKQMEEEAVR LFIEWLKNGG PSSGAPPPSG GGGSGGGGSG GGGSAEPKSC

 61 DKTHTCPPCP APELLGGPSV FLFPPKPKDT LMISRTPEVT CVVVDVSHED PEVKFNWYVD

121 GVEVHNAKTK PREEQYNSTY RVVSVLTVLH QDWLNGKEYK CKVSNKALPA PIEKTISKAK

181 GQPREPQVYT LPPSREEMTK NQVSLTCLVK GFYPSDIAVE WESNGQPENN YKTTPPVLDS

241 DGSFFLYSKL TVDKSRWQQG NVFSCSVMHE ALHNHYTQKS LSLSPGK
```

TABLE 5a

In vitro GLP 1 analog activity

| GLP-1 Compound | GLP-1 Receptor Activation |
|---|---|
| GLP-1(7-37)OH | 1.0 |
| $Val^8$-GLP-1(7-37)OH | 0.47 (n = 6) |
| $Gly^8$-$His^{11}$-GLP-1(7-37)OH | 0.282 |
| $Val^8$-$Ala^{11}$-GLP-1(7-37)OH | 0.021 |

TABLE 5a-continued

In vitro GLP 1 analog activity

| GLP-1 Compound | GLP-1 Receptor Activation |
|---|---|
| $Val^8$-$Lys^{11}$-GLP-1(7-37)OH | 0.001 |
| $Val^8$-$Tyr^{12}$-GLP-1(7-37)OH | 0.81 |
| $Val^8$-$Glu^{16}$-GLP-1(7-37)OH | 0.047 |
| $Val^8$-$Ala^{16}$-GLP-1(7-37)OH | 0.112 |
| $Val^8$-$Tyr^{16}$-GLP-1(7-37)OH | 1.175 |
| $Val^8$-$Lys^{20}$-GLP-1(7-37)OH | 0.33 |
| $Gln^{22}$-GLP-1(7-37)OH | 0.42 |
| $Val^8$-$Ala^{22}$-GLP-1(7-37)OH | 0.56 |
| $Val^8$-$Ser^{22}$-GLP-1(7-37)OH | 0.50 |
| $Val^8$-$Asp^{22}$-GLP-1(7-37)OH | 0.40 |
| $Val^8$-$Glu^{22}$-GLP-1(7-37)OH | 1.29 |
| $Val^8$-$Lys^{22}$-GLP-1(7-37)OH | 0.58 |
| $Val^8$-$Pro^{22}$-GLP-1(7-37)OH | 0.01 |
| $Val^8$-$His^{22}$-GLP-1(7-37)OH | 0.14 |
| $Val^8$-$Lys^{22}$-GLP-1(7-36)$NH_2$ | 0.53 |
| $Val^8$-$Glu^{22}$-GLP-1(7-36)$NH_2$ | 1.0 |
| $Gly^8$-$Glu^{22}$-GLP-1(7-37)OH | 1.07 |
| $Val^8$-$Lys^{23}$-GLP-1(7-37)OH | 0.18 |
| $Val^8$-$His^{24}$-GLP-1(7-37)OH | 0.007 |
| $Val^8$-$Lys^{24}$-GLP-1(7-37)OH | 0.02 |
| $Val^8$-$His^{26}$-GLP-1(7-37)OH | 1.6 |
| $Val^8$-$Glu^{26}$-GLP-1(7-37)OH | 1.5 |
| $Val^8$-$His^{27}$-GLP-1(7-37)OH | 0.37 |
| $Val^8$-$Ala^{27}$-GLP-1(7-37)OH | 0.47 |
| $Gly^8$-$Glu^{30}$-GLP-1(7-37)OH | 0.29 |
| $Val^8$-$Glu^{30}$-GLP-1(7-37)OH | 0.29 |
| $Val^8$-$Asp^{30}$-GLP-1(7-37)OH | 0.15 |
| $Val^8$-$Ser^{30}$-GLP-1(7-37)OH | 0.19 |
| $Val^8$-$His^{30}$-GLP-1(7-37)OH | 0.19 |
| $Val^8$-$Glu^{33}$-GLP-1(7-37)OH | 0.039 |
| $Val^8$-$Ala^{33}$-GLP-1(7-37)OH | 0.1 |
| $Val^8$-$Gly^{33}$-GLP-1(7-37)OH | 0.01 |
| $Val^8$-$Glu^{34}$-GLP-1(7-37)OH | 0.17 |
| $Val^8$-$Pro^{35}$-GLP-1(7-37)OH | 0.094 |
| $Val^8$-$His^{35}$-GLP-1(7-37)OH | 0.41 |
| $Val^8$-$Glu^{35}$-GLP-1(7-37)OH | 0.15 |
| $Val^8$-$Glu^{36}$-GLP-1(7-37)OH | 0.11 |
| $Val^8$-$His^{36}$-GLP-1(7-37)OH | 0.22 |
| $Val^8$-$His^{37}$-GLP-1(7-37)OH | 0.33 |
| $Val^8$-$Leu^{16}$-$Glu^{26}$-GLP-1(7-37)OH | 0.23 |
| $Val^8$-$Lys^{22}$-$Glu^{30}$-GLP-1(7-37)OH | 0.37 |
| $Val^8$-$Lys^{22}$-$Glu^{23}$-GLP-1(7-37)OH | 0.35 |
| $Val^8$-$Glu^{22}$-$Ala^{27}$-GLP-1(7-37)OH | 1.02 |
| $Val^8$-$Glu^{22}$-$Lys^{23}$-GLP-1(7-37)OH | 1.43 |
| $Val^8$-$Lys^{33}$-$Val^{34}$-GLP-1(7-37)OH | 0.08 |
| $Val^8$-$Lys^{33}$-$Asn^{34}$-GLP-1(7-37)OH | 0.09 |
| $Val^8$-$Gly^{34}$-$Lys^{35}$-GLP-1(7-37)OH | 0.34 |
| $Val^8$-$Gly^{36}$-$Pro^{37}$-GLP-1(7-37)$NH_2$ | 0.53 |

TABLE 5b

In vitro GLP-1 analog activity

| GLP-1 Compound | GLP-1 Receptor Activation |
|---|---|
| GLP-1(7-37)OH | 1.0 |
| $Val^8$-GLP-1(7-37)OH | 0.47 |
| $Gly^8$-GLP-1(7-37)OH | 0.80 |
| $Val^8$-$Tyr^{12}$-GLP-1(7-37)OH | 0.80 |
| $Val^8$-$Tyr^{12}$-GLP-1(7-36)$NH_2$ | 0.52 |
| $Val^8$-$Trp^{12}$-GLP-1(7-37)OH | 0.52 |
| $Val^8$-$Leu^{16}$-GLP-1(7-37)OH | 0.52 |
| $Val^8$-$Val^{16}$-GLP-1(7-37)OH | 0.52 |
| $Val^8$-$Tyr^{16}$-GLP-1(7-37)OH | 1.18 |
| $Gly^8$-$Glu^{22}$-GLP-1(7-37)OH | 1.03 |
| $Val^8$-$Leu^{25}$-GLP-1(7-37)OH | 0.24 |
| $Val^8$-$Tyr^{12}$-$Tyr^{16}$-GLP-1(7-37)OH | 0.70 |
| $Val^8$-$Trp^{12}$-$Glu^{22}$-GLP-1(7-37)OH | 0.80 |
| $Val^8$-$Tyr^{12}$-$Glu^{22}$-GLP-1(7-37)OH | 1.27 |
| $Val^8$-$Tyr^{16}$-$Phe^{19}$-GLP-1(7-37)OH | 1.32 |
| $Val^8$-$Tyr^{16}$-$Glu^{22}$-GLP-1(7-37)OH | 1.69, 1.79 |
| $Val^8$-$Trp^{16}$-$Glu^{22}$-GLP-1(7-37)OH | 2.30, 2.16 |
| $Val^8$-$Leu^{16}$-$Glu^{22}$-GLP-1(7-37)OH | 2.02 |
| $Val^8$-$Ile^{16}$-$Glu^{22}$-GLP-1(7-37)OH | 1.55 |
| $Val^8$-$Phe^{16}$-$Glu^{22}$-GLP-1(7-37)OH | 1.08 |
| $Val^8$-$Trp^{18}$-$Glu^{22}$-GLP-1(7-37)OH | 1.50, 3.10 |

TABLE 5b-continued

In vitro GLP-1 analog activity

| GLP-1 Compound | GLP-1 Receptor Activation |
|---|---|
| $Val^8$-$Tyr^{18}$-$Glu^{22}$-GLP-1(7-37)OH | 2.40, 2.77 |
| $Val^8$-$Phe^{18}$-$Glu^{22}$-GLP-1(7-37)OH | 0.94 |
| $Val^8$-$Ile^{18}$-$Glu^{22}$-GLP-1(7-37)OH | 1.88 |
| $Val^8$-$Lys^{18}$-$Glu^{22}$-GLP-1(7-37)OH | 1.18 |
| $Val^8$-$Trp^{19}$-$Glu^{22}$-GLP-1(7-37)OH | 1.50 |
| $Val^8$-$Phe^{19}$-$Glu^{22}$-GLP-1(7-37)OH | 0.70 |
| $Val^8$-$Phe^{20}$-$Glu^{22}$-GLP-1(7-37)OH | 1.27 |
| $Val^8$-$Glu^{22}$-$Leu^{25}$-GLP-1(7-37)OH | 1.32 |
| $Val^8$-$Glu^{22}$-$Ile^{25}$-GLP-1(7-37)OH | 1.46 |
| $Val^8$-$Glu^{22}$-$Val^{25}$-GLP-1(7-37)OH | 2.21, 1.36 |
| $Val^8$-$Glu^{22}$-$Ile^{27}$-GLP-1(7-37)OH | 0.94 |
| $Val^8$-$Glu^{22}$-$Ala^{27}$-GLP-1(7-37)OH | 1.03 |
| $Val^8$-$Glu^{22}$-$Ile^{33}$-GLP-1(7-37)OH | 2.21, 1.79, 1.60 |
| $Val^8$-$Asp^9$-$Ile^{11}$-$Tyr^{16}$-$Glu^{22}$-GLP-1(7-37)OH | 2.02 |
| $Val^8$-$Tyr^{16}$-$Trp^{19}$-$Glu^{22}$-GLP-1(7-37)OH | 1.64 |
| $Val^8$-$Trp^{16}$-$Glu^{22}$-$Val^{25}$-$Ile^{33}$-GLP-1(7-37)OH | 2.35 |
| $Val^8$-$Trp^{16}$-$Glu^{22}$-$Ile^{33}$-GLP-1(7-37)OH | 1.93 |
| $Val^8$-$Glu^{22}$-$Val^{25}$-$Ile^{33}$-GLP-1(7-37)OH | 2.30, 2.73, 3.15 |
| $Val^8$-$Trp^{16}$-$Glu^{22}$-$Val^{25}$-GLP-1(7-37)OH | 2.07 |
| $Val^8$-$Cys^{16}$-$Lys^{26}$-GLP-1(7-37)OH | 1.97 |
| $Val^8$-$Cys^{16}$-$Lys^{26}$-$Arg^{34}$-GLP-1(7-37)OH | 2.4,1.9 |

TABLE 6

In vitro activity of GLP/Exendin analogs

| Peptide Sequence | In Vitro Activity (% of $Val^8$-GLP-1(7-37)OH) |
|---|---|
| HGEGTFTSDLSKQMEEEAVR-LFIEWLKNGGP-NH2 | 6.21 |
| HGEGTFTSDLSKQMEEEAVR-LFIEWLKNGGPSSGAPPPS-NH2 | 6.75, 3.25 |
| HVEGTFTSDLSKQMEEEAVR-LFIAWLVKGRG | 2.86 |
| HVEGTFTSDVSSYLEEEAVR-LFIAWLVKGRG | 1.47 |

TABLE 6-continued

In vitro activity of GLP/Exendin analogs

| Peptide Sequence | In Vitro Activity (% of $Val^8$-GLP-1(7-37)OH) |
|---|---|
| HVEGTFTSDL-SKQMEGQAAKEFIAWLVKGRG | 0.11 |
| HVEGTFTSD-VSKQMEGQAAKEFI-AWLVKGRG | 0.04 |
| HGEGTFTSDL-SKQMEGQAAKE-FIEWLKNGGP-NH2 | 1.44 |
| HGEGTFTSDLSKQMEEE-AAKEFIEWLKNGGP-NH2 | 2.80 |
| HGEGTFTSDVSSYLEEEAVR-LFIEWLKNGGP-NH2 | 5.40 |
| HGEGTFTSDLSSYLEEEAVR-LFIEWLKNGGP-NH2 | 5.07 |
| HAEGTFTSDVS-SYLEGQAAKEFI-AWLVKGRPSSGAPPPS-NH2 | 3.30 |
| HAEGTFTSDVSKQLEEE-AAKEFIAWLVKGRG | 2.15 |
| HVEGTFTSDVS-SYLEGQAAKEFIEWLKNGGP-NH2 | 2.36 |
| HGEGTFTSDLSKQMEEEAVR-LFIAWLVKGRG | 3.25 |
| HVEGTFTSDVSSYLEEE-AAKEFIAWLVKGRG | 1.00 |
| HVEGTFTSDVS-SYLEGQAAKEFIAWLKNGRG | 0.20 |
| HVEGTFTSDVS-SYLEGQAAKEFIAWLVKGRG | 1.00 |
| HAEGTFTSDVS-SYLEGQAAKEFIAWLVKGRG | 2.12 |

EXAMPLE 7

In vivo Pharmacokinetics of $Val^8$-GLP-1-IgG1 and $Val^8$-GLP-1-HSA

A pharmacokinetic study of $Val^8$-GLP-1-IgG1 and $Val^8$-GLP-1-HSA was performed in cynomologus monkeys. Monkeys were dosed at 5.6 nmoles/kg with either purified $Val^8$-GLP-1-IgG1 or $Val^8$-GLP-1-HSA . The compounds were administered as an intravenous bolus administration. Blood was collected pre-dose and at 0.083, 0.25, 0.5, 1, 4, 8, 12, 24, 48, 72, 96, 120, 144, 168, and 216 hours post-dose into tubes containing EDTA. Plasma concentrations of immunoreactive $Val^8$-GLP-1 were determined using a radioimmunoassay that utilizes a polyclonal antiserum whose primary specificity is for the N-terminal (7-16) region of $Val^8$-GLP-1(7-37). FIG. 9 depicts the plasma concentration of $Val^8$-GLP-1-Fc and $Val^8$-GLP-1-Linker-HSA following a single intravenous dose to two cynomologus monkeys. The Fc fusion protein had a half-life of approximately 45 hours and the albumin fusion had a half-life of approximately 87 hours.

EXAMPLE 8

In vivo Pharmacodynamics of Exendin-4-IgG1

Two chronically cannulated normal male beagle dogs were studied after an overnight fast. Arterial and venous vascular access ports were accessed, and a catheter was inserted percutaneously into a cephalic vein and secured. Animals were placed in cages, and their catheters were attached to a swivel/tether system. A solution containing the fusion protein Exendin-4-IgG1 (11.8 μM) was injected intravenously (1.0 nmol/kg) through the cephalic vein catheter. The catheter was then cleared with 10 ml of saline. Two hours later, a hyperglycemic (150 mg/dl) clamp was initiated and continued for three hours. Arterial blood samples were drawn throughout this 5-hour period for determination of plasma concentrations of the fusion protein, glucose, and insulin.

The results of this study were compared to those from a similar, previous study in which both of the animals had received a bolus of saline, s.c., and three hours later were studied using a 3-hour hyperglycemic (150 mg/dl) clamp.

In both sets of studies, plasma glucose concentrations were determined using a Beckman glucose analyzer. Plasma insulin concentrations were determined by employees of Linco Research, Inc. using an RIA kit developed in their laboratories. The data is illustrated in FIGS. 10 and 11.

EXAMPLE 9

In vivo Pharmacokinetics of Gly$^{8}$-Glu$^{22}$-GLP-1-CEx-Linker-IgG1

Two groups of three normal male beagle dogs received 0.1 mg/kg of Gly$^{8}$-Glu$^{22}$-GLP-1-CEx-Linker-IgG1 by subcutaneous (SC) or intravenous (IV) administration. Plasma concentrations of Gly$^{8}$-Glu$^{22}$-GLP-1-CEx-Linker-IgG1 immunoreactivity were determined by radioimmunoassay in samples collected from 30 minutes predose to 216 hours postdose for both the IV and SC groups. These concentrations were subsequently used to determine the reported pharmacokinetic parameters. The mean elimination half-life of IV administered Gly$^{8}$-Glu$^{22}$-GLP-1-CEx-Linker-IgG1 was approximately 55 hours and the total body clearance was 1.5 mL/h/kg. The mean elimination half-life of SC administered Gly$^{8}$-Glu$^{22}$-GLP-1-CEx-Linker-IgG1 was approximately 38 hours.

We claim:

1. A heterologous fusion protein comprising a first polypeptide with a N-terminus and a C-terminus fused to a second polypeptide with a N-terminus and a C-terminus wherein the first polypeptide is a GLP-1 compound and the second polypeptide is selected from the group consisting of a) human albumin;

b) human albumin analogs; and c) fragments of human albumin, and wherein the C-terminus of the first polypeptide is fused to the N-terminus of the second polypeptide.

2. A heterologous fusion protein comprising a first polypeptide with a N-terminus terminus and a C-terminus fused to a second polypeptide with a N-terminus and a C-terminus wherein the first polypeptide is a GLP-1 compound and the second polypeptide is selected from the group consisting of a) human albumin;

b) human albumin analogs; and c) fragments of human albumin, and wherein the C-terminus of the first polypeptide is fused to the N-terminus of the second polypeptide via a peptide linker.

3. The heterologous fusion protein of the claim 2 wherein the peptide linker is selected from the group consisting of:

a) a glycine rich peptide;

b) a peptide having the sequence [Gly-Gly-Gly-Gly-Ser]$_n$ where n is 1, 2, 3, 4, 5 or 6; and c) a peptide having the sequence [Gly-Gly-Gly-Gly-Ser]$_3$.

4. The heterologous fusion protein of claims 1, 2, or 3 wherein the GLP-1 compound comprises the sequence of formula 1 [SEQ ID NO: 2]

```
                                          (SEQ ID NO: 2)
7   8   9   10  11  12  13  14  15  16  17
His-Xaa-Xaa-Gly-Xaa-Phe-Thr-Xaa-Asp-Xaa-Xaa-

18  19  20  21  22  23  24  25  26  27  28
Xaa-Xaa-Xaa-Xaa-Xaa-Xaa-Xaa-Xaa-Xaa-Xaa-Phe-

29  30  31  32  33  34  35  36  37  38  39
Ile-Xaa-Xaa-Xaa-Xaa-Xaa-Xaa-Xaa-Xaa-Xaa-Xaa-

40  41  42  43  44  45
Xaa-Xaa-Xaa-Xaa-Xaa-Xaa
Formula I
```

wherein:

Xaa at position 8 is Ala, Gly, Ser, Thr, Leu, Ile, Val, Glu, Asp, or Lys;

Xaa at position 9 is Glu, Asp, or Lys;

Xaa at position 11 is Thr, Ala, Gly, Ser, Leu, Ile, Val, Glu, Asp, or Lys;

Xaa at position 14 is Ser, Ala, Gly, Thr, Leu, Ile, Val, Glu, Asp, or Lys;

Xaa at position 16 is Val, Ala, Gly, Ser, Thr, Leu, Ile, Tyr, Glu, Asp, Trp, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, Trp, Tyr, or Lys;

Xaa at position 19 is Tyr, Phe, Trp, Glu, Asp, Gln, or Lys;

Xaa at position 20 is Leu, Ala, Gly, Ser, Thr, Ile, Val, Glu, Asp, Met, Trp, Tyr, or Lys;

Xaa at position 21 is Glu, Asp, or Lys;

Xaa at position 22 is Gly, Ala, Ser, Thr, Leu, Ile, Val, Glu, Asp, or Lys;

Xaa at position 23 is Gln, Asn, Arg, Glu, Asp, or Lys;

Xaa at position 24 is Ala, Gly, Ser, Thr, Leu, Ile, Val, Arg, Glu, Asp, or Lys;

Xaa at position 25 is Ala, Gly, Ser, Thr, Leu, Ile, Val, Glu, Asp, or Lys;

Xaa at position 26 is Lys, Arg, Gln, Glu, Asp, or His;

Xaa at position 27 is Leu, Glu, Asp, or Lys;

Xaa at position 30 is Ala, Gly, Ser, Thr, Leu, Ile, Val, Glu, Asp, or Lys;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 37 is Pro, Gly, Ala, Ser, Thr, Leu, Ile, Val, Glu, Asp, or Lys, or is deleted;

Xaa at position 38 is Ser, Arg, Lys, Glu, Asp, or His, or is deleted;

Xaa at position 39 is Ser, Arg, Lys, Glu, Asp, or His, or is deleted;

Xaa at position 40 is Gly, Asp, Glu, or Lys, or is deleted;

Xaa at position 41 is Ala, Phe, Trp, Tyr, Glu, Asp, or Lys, or is deleted;

Xaa at position 42 is Ser, Pro, Lys, Glu, or Asp, or is deleted;

Xaa at position 43 is Ser, Pro, Glu, Asp, or Lys, or is deleted;

Xaa at position 44 is Gly, Pro, Glu, Asp, or Lys, or is deleted; and

Xaa at position 45 is Ala, Ser, Val, Glu, Asp, or Lys, or is deleted;

provided that when the amino acid at position 37, 38, 39, 40, 41, 42, 43, or 44 is deleted, then each amino acid downstream of that amino acid is also deleted.

5. The heterologous fusion protein of claims 1, 2, or 3 wherein the GLP-1 compound comprises the sequence of formula II (SEQ ID NO: 3):

```
                                              (SEQ ID NO: 3)
7   8   9   10  11  12  13  14  15  16  17
Xaa-Xaa-Xaa-Gly-Xaa-Xaa-Thr-Ser-Asp-Xaa-Ser-

18  19  20  21  22  23  24  25  26  27  28
Xaa-Tyr-Leu-Glu-Xaa-Xaa-Xaa-Ala-Xaa-Xaa-Phe-

29  30  31  32  33  34  35  36  37
Ile-Xaa-Xaa-Leu-Xaa-Xaa-Xaa-Xaa-Xaa
Formula II
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, or Thr;

Xaa at position 9 is: Thr, Ser, Arg, Lys, Trp, Phe, Tyr, Glu, or His;

Xaa at position 11 is: Asp, Glu, Arg, Thr, Ala, Lys, or His;

Xaa at position 12 is: His, Trp, Phe, or Tyr;

Xaa at position 16 is: Leu, Ser, Thr, Trp, His, Phe, Asp, Val, Tyr, Glu, or Ala;

Xaa at position 18 is: His, Pro, Asp, Glu, Arg, Ser, Ala, or Lys;

Xaa at position 22 is: Gly, Asp, Glu, Gln, Asn, Lys, Arg, or Cys;

Xaa at position 23 is: His, Asp, Lys, Glu, Gln, or Arg;

Xaa at position 24 is: Glu, Arg, Ala, or Lys;

Xaa at position 26 is: Trp, Tyr, Phe, Asp, Lys, Glu, or His;

Xaa at position 27 is: Ala, Glu, His, Phe, Tyr, Trp, Arg, or Lys;

Xaa at position 30 is: Ala, Glu, Asp, Ser, or His;

Xaa at position 31 is: Asp, Glu, Ser, Thr, Arg, Trp, or Lys;

Xaa at position 33 is: Asp, Arg, Val, Lys, Ala, Gly, or Glu;

Xaa at position 34 is: Glu, Lys, or Asp;

Xaa at position 35 is: Thr, Ser, Lys, Arg, Trp, Tyr, Phe, Asp, Gly, Pro, His, or Glu;

Xaa at position 36 is: Thr, Ser, Asp, Trp, Tyr, Phe, Arg, Glu, or His;

Xaa at position 37 is: Lys, Arg, Thr, Ser, Glu, Asp, Trp, Tyr, Phe, His, Gly, Gly-Pro, or is deleted.

6. The heterologous fusion protein of claims 1, 2, or 3 wherein the GLP-1 compound comprises the sequence of formula III (SEQ ID NO: 4):

```
                                              (SEQ ID NO: 4)
7   8   9   10  11  12  13  14  15  16  17
Xaa-Xaa-Glu-Gly-Xaa-Xaa-Thr-Ser-Asp-Xaa-Ser-

18  19  20  21  22  23  24  25  26  27  28
Ser-Tyr-Leu-Glu-Xaa-Xaa-Xaa-Xaa-Lys-Xaa-Phe-

29  30  31  32  33  34  35  36  37
Ile-Xaa-Trp-Leu-Xaa-Xaa-Xaa-Xaa-Xaa
formula III
```

wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is: Gly, Ala, Val, Leu, Ile, Ser, or Thr;

Xaa at position 11 is: Asp, Glu, Arg, Thr, Ala, Lys, or His;

Xaa at position 12 is: His, Trp, Phe, or Tyr;

Xaa at position 16 is: Leu, Ser, Thr, Trp, His, Phe, Asp, Val, Glu, or Ala;

Xaa at position 22: Gly, Asp, Glu, Gln, Asn, Lys, Arg, or Cys;
Xaa at position 23 is: His, Asp, Lys, Glu, or Gln;
Xaa at position 24 is: Glu, His, Ala, or Lys;
Xaa at position 25 is: Asp, Lys, Glu, or His;
Xaa at position 27 is: Ala, Glu, His, Phe, Tyr, Trp, Arg, or Lys;
Xaa at position 30 is: Ala, Glu, Asp, Ser, or His;
Xaa at position 33 is: Asp, Arg, Val, Lys, Ala, Gly, or Glu;
Xaa at position 34 is: Glu, Lys, or Asp;
Xaa at position 35 is: Thr, Ser, Lys, Arg, Trp, Tyr, Phe, Asp, Gly, Pro, His, or Glu;
Xaa at position 36 is: Arg, Glu, or His;
Xaa at position 37 is: Lys, Arg, Thr, Ser, Glu, Asp, Trp, Tyr, Phe, His, Gly, Gly-Pro, or is deleted.

7. The heterologous fusion protein of claim 1 wherein the GLP-1 compound has no more than 6 amino acids that are different from the corresponding amino acid in GLP-1(7-37)OH, GLP-1(7-36)OH, or Exendin-4.

8. The heterologous fusion protein of claim 7 wherein the GLP-1 compound has no more than 5 amino acids that differ from the corresponding amino acid in GLP-1(7-37)OH, GLP-1(7-36)OH, or Exendin-4.

9. The heterologous fusion protein of claim 8 wherein the GLP-1 compound has no more than 4 amino acids that differ from the corresponding amino acid in GLP-1(7-37)OH, GLP-1(7-36)OH, or Exendin-4.

10. The heterologous fusion protein of claim 9 wherein the GLP-1 compound has no more than 3 amino acids that differ from the corresponding amino acid in GLP-1(7-37)OH, GLP-1(7-36)OH, or Exendin-4.

11. The heterologous fusion protein of claim 10 wherein the GLP-1 compound has no more than 2 amino acids that differ from the corresponding amino acid in GLP-1(7-37)OH, GLP-1(7-36)OH, or Exendin-4.

12. A method of treating a patient with non-insulin dependent diabetes mellitus comprising the administration of a therapeutically effective amount of the heterologous fusion protein of claim 1.

13. A method of treating obesity comprising the administration of a therapeutically effective amount of the heterologous fusion protein of claim 1.

* * * * *